(12) United States Patent
Tamura et al.

(10) Patent No.: US 9,301,913 B2
(45) Date of Patent: Apr. 5, 2016

(54) ORGANO POLYSILOXANE ELASTOMER AND USE THEREFOR

(75) Inventors: Seiki Tamura, Ichihara (JP); Tatsuo Souda, Ichihara (JP); Seiji Hori, Sabae (JP)

(73) Assignee: DOW CORNING TORAY CO., LTD., Tokyo (JP)

( * ) Notice: Subject to any disclaimer, the term of this patent is extended or adjusted under 35 U.S.C. 154(b) by 165 days.

(21) Appl. No.: 14/122,689

(22) PCT Filed: May 22, 2012

(86) PCT No.: PCT/JP2012/063074
§ 371 (c)(1),
(2), (4) Date: Feb. 13, 2014

(87) PCT Pub. No.: WO2012/165228
PCT Pub. Date: Dec. 6, 2012

(65) Prior Publication Data
US 2014/0161758 A1    Jun. 12, 2014

(30) Foreign Application Priority Data

May 30, 2011 (JP) .................................. 2011-121097

(51) Int. Cl.
| | |
|---|---|
| A61K 8/89 | (2006.01) |
| C08L 83/12 | (2006.01) |
| A61K 8/892 | (2006.01) |
| C08G 77/46 | (2006.01) |
| C08G 77/50 | (2006.01) |
| C08L 83/14 | (2006.01) |
| A61K 9/00 | (2006.01) |
| A61K 47/34 | (2006.01) |
| A61K 9/107 | (2006.01) |
| A61Q 19/00 | (2006.01) |
| A61K 8/895 | (2006.01) |
| A61K 8/02 | (2006.01) |
| A61Q 19/08 | (2006.01) |
| A61Q 5/00 | (2006.01) |
| A61K 8/893 | (2006.01) |
| C08G 77/12 | (2006.01) |

(52) U.S. Cl.
CPC .............. *A61K 8/892* (2013.01); *A61K 8/0241* (2013.01); *A61K 8/893* (2013.01); *A61K 8/895* (2013.01); *A61K 9/0014* (2013.01); *A61K 9/107* (2013.01); *A61K 47/34* (2013.01); *A61Q 5/00* (2013.01); *A61Q 19/00* (2013.01); *A61Q 19/007* (2013.01); *A61Q 19/08* (2013.01); *C08G 77/46* (2013.01); *C08G 77/50* (2013.01); *C08L 83/12* (2013.01); *C08L 83/14* (2013.01); *A61K 2800/10* (2013.01); *C08G 77/12* (2013.01); *Y10T 428/2982* (2015.01)

(58) Field of Classification Search
None
See application file for complete search history.

(56) References Cited

U.S. PATENT DOCUMENTS

| | | | |
|---|---|---|---|
| 4,222,952 | A | 9/1980 | Vick |
| 4,515,979 | A | 5/1985 | Otsuki et al. |
| 4,853,474 | A | 8/1989 | Bahr et al. |
| 4,940,751 | A | 7/1990 | Frances et al. |
| 4,987,169 | A | 1/1991 | Kuwata et al. |
| 5,136,068 | A * | 8/1992 | Bahr et al. ...................... 516/20 |
| 5,225,509 | A | 7/1993 | Heinrich et al. |
| 5,236,986 | A | 8/1993 | Sakuta |
| 5,288,831 | A | 2/1994 | Ichinohe et al. |
| 5,387,417 | A * | 2/1995 | Rentsch ........................ 424/401 |
| 5,654,362 | A | 8/1997 | Schulz, Jr. et al. |
| 5,811,487 | A | 9/1998 | Schulz, Jr. et al. |
| 5,981,680 | A | 11/1999 | Petroff et al. |
| 6,239,244 | B1 | 5/2001 | Stepp et al. |
| 6,677,446 | B2 | 1/2004 | Duval |
| 8,288,498 | B2 | 10/2012 | Hayashi et al. |
| 8,686,174 | B2 | 4/2014 | Okawa |
| 8,784,787 | B2 * | 7/2014 | Tamura et al. ............. 424/70.19 |

(Continued)

FOREIGN PATENT DOCUMENTS

| | | |
|---|---|---|
| AT | 312121 T | 12/2005 |
| AT | 356845 T | 4/2007 |

(Continued)

OTHER PUBLICATIONS

"Silicones", Encyclopedia of Polymer Science and Technology, vol. 11, Wiley, pp. 765-841, Apr. 15, 2003, XP007918236.

(Continued)

*Primary Examiner* — Marc Zimmer
(74) *Attorney, Agent, or Firm* — Howard & Howard Attorneys PLLC

(57) ABSTRACT

The present invention relates to an organopolysiloxane elastomer having a group having a siloxane dendron structure bonded to a silicon atom, and having a crosslinked structure that includes a carbon-silicon bond in the crosslinking portion, and relates to a glycerin derivative-modified organopolysiloxane elastomer having a siloxane dendron structure bonded to a silicon atom and a hydrophilic group bonded to a different silicon atom from the silicon atom, and having a crosslinked structure that includes a carbon-silicon bond in the crosslinking portion. The organopolysiloxane elastomer of the present invention, for example, has affinity with a variety of oil agents, has excellent structuring properties and gelling characteristics, and further retains excellent tactile sensation, particularly a velvety thick smoothness, and moreover imparts an excellent tactile sensation from initial application to after drying without producing any stickiness at all, and furthermore, provides superior cosmetic effects, such as wrinkle concealing effect (masking effect), and the like.

31 Claims, No Drawings

(56) References Cited

U.S. PATENT DOCUMENTS

| | | |
|---|---|---|
| 2002/0035229 A1 | 3/2002 | Kondo et al. |
| 2003/0158363 A1 | 8/2003 | Nakanishi |
| 2004/0068106 A1 | 4/2004 | Duval |
| 2004/0091439 A1 | 5/2004 | Kamei et al. |
| 2004/0146472 A1 | 7/2004 | Nakanishi |
| 2004/0253197 A1 | 12/2004 | Sakuta |
| 2005/0043365 A1 | 2/2005 | Yoshitake et al. |
| 2006/0018935 A1 | 1/2006 | Nishijima et al. |
| 2006/0034875 A1 | 2/2006 | Nakanishi et al. |
| 2006/0165629 A1 | 7/2006 | Kamei et al. |
| 2007/0004858 A1 | 1/2007 | Zech et al. |
| 2008/0138386 A1 | 6/2008 | Joffre et al. |
| 2008/0200608 A1 | 8/2008 | Burger et al. |
| 2008/0273168 A1 | 11/2008 | Rathore et al. |
| 2008/0311060 A1 | 12/2008 | Sakuta et al. |
| 2009/0171057 A1 | 7/2009 | O'Lenick et al. |
| 2009/0203802 A1 | 8/2009 | Kamei et al. |
| 2009/0232856 A1 | 9/2009 | Patel |
| 2009/0232859 A1 | 9/2009 | Sakuta et al. |
| 2010/0113731 A1 | 5/2010 | Hayashi et al. |
| 2010/0158824 A1 | 6/2010 | Lin |
| 2011/0015337 A1 | 1/2011 | Sakuta et al. |
| 2011/0251417 A1 | 10/2011 | Okawa |
| 2012/0269747 A1 | 10/2012 | Iimura et al. |
| 2012/0269748 A1 | 10/2012 | Tamura et al. |
| 2012/0269875 A1 | 10/2012 | Tamura et al. |
| 2013/0102686 A1 | 4/2013 | Tamura et al. |

FOREIGN PATENT DOCUMENTS

| | | |
|---|---|---|
| AT | 526365 T | 10/2011 |
| AU | 4734599 A | 6/2000 |
| AU | 769244 A | 1/2004 |
| CA | 2281973 A1 | 3/2000 |
| CN | 101084275 A | 12/2007 |
| CN | 101641396 A | 2/2010 |
| CN | 102257040 A | 11/2011 |
| DE | 3881647 T2 | 10/1993 |
| DE | 19711314 A1 | 9/1998 |
| DE | 69928733 T2 | 8/2006 |
| DE | 60218891 T2 | 12/2007 |
| DE | 112008000839 T5 | 2/2010 |
| DK | 0985682 T3 | 4/2006 |
| EP | 0317377 A1 | 5/1989 |
| EP | 0381318 A2 | 8/1990 |
| EP | 0985682 A1 | 3/2000 |
| EP | 1148100 A2 | 10/2001 |
| EP | 1416016 A1 | 5/2004 |
| EP | 1512724 A1 | 3/2005 |
| EP | 2014701 A2 | 1/2009 |
| EP | 2716685 A1 | 4/2014 |
| EP | 2716686 A1 | 4/2014 |
| EP | 2716687 A1 | 4/2014 |
| ES | 2252924 T3 | 5/2006 |
| FR | 2622201 A1 | 4/1989 |
| FR | 2784108 A1 | 4/2000 |
| JP | S5541210 B2 | 10/1980 |
| JP | S594446 B2 | 1/1984 |
| JP | S6018525 A | 1/1985 |
| JP | S6268820 A | 3/1987 |
| JP | S63139106 A | 6/1988 |
| JP | S63248410 A | 10/1988 |
| JP | H01152158 A | 6/1989 |
| JP | H01207354 A | 8/1989 |
| JP | H0243263 A | 2/1990 |
| JP | H02302438 A | 12/1990 |
| JP | H04272932 A | 9/1992 |
| JP | H05140320 A | 6/1993 |
| JP | H05186596 A | 7/1993 |
| JP | H06040847 A | 2/1994 |
| JP | H06040848 A | 2/1994 |
| JP | H07041417 A | 2/1995 |
| JP | H07185212 A | 7/1995 |
| JP | H07187945 A | 7/1995 |
| JP | H07292119 A | 11/1995 |
| JP | H07330907 A | 12/1995 |
| JP | H08000908 A | 1/1996 |
| JP | H09071504 A | 3/1997 |
| JP | H09165315 A | 6/1997 |
| JP | H09165318 A | 6/1997 |
| JP | H10316536 A | 12/1998 |
| JP | H11049957 A | 2/1999 |
| JP | 2000038450 A | 2/2000 |
| JP | 2000063225 A | 2/2000 |
| JP | 2000086702 A | 3/2000 |
| JP | 2000509761 A | 8/2000 |
| JP | 2000319515 A | 11/2000 |
| JP | 2001064513 A | 3/2001 |
| JP | 2001115390 A | 4/2001 |
| JP | 2002105318 A | 4/2001 |
| JP | 2001187842 A | 7/2001 |
| JP | 2001192459 A | 7/2001 |
| JP | 2001512164 A | 8/2001 |
| JP | 2001294755 A | 10/2001 |
| JP | 2002119840 A | 4/2002 |
| JP | 2002179798 A | 6/2002 |
| JP | 2003146991 A | 5/2003 |
| JP | 2004169015 A | 6/2004 |
| JP | 2004174495 A | 6/2004 |
| JP | 2005120293 A | 5/2005 |
| JP | 2005523980 A | 8/2005 |
| JP | 2005529989 A | 10/2005 |
| JP | 2006511645 A | 4/2006 |
| JP | 2006511646 A | 4/2006 |
| JP | 2007504312 A | 3/2007 |
| JP | 2007126359 A | 5/2007 |
| JP | 4009382 B2 | 11/2007 |
| JP | 2007532754 A | 11/2007 |
| JP | 2008115358 A | 5/2008 |
| JP | 2008525598 A | 7/2008 |
| JP | 4187198 B2 | 11/2008 |
| JP | 2008274241 A | 11/2008 |
| JP | 2008542010 A | 11/2008 |
| JP | 2009262080 A | 11/2009 |
| JP | 2010120913 A | 6/2010 |
| JP | 2010144156 A | 7/2010 |
| JP | 2011049248 A | 3/2011 |
| JP | 2011121095 A | 6/2011 |
| JP | 2011121097 A | 6/2011 |
| JP | 2011246705 A | 12/2011 |
| JP | 2012246446 A | 12/2012 |
| KR | 20040038865 A | 5/2004 |
| KR | 20080042784 A | 5/2008 |
| KR | 20110087330 A | 8/2011 |
| NO | 994411 A | 3/2000 |
| WO | WO 98/41579 | 9/1998 |
| WO | WO 9906473 A1 | 2/1999 |
| WO | WO 0114458 A1 | 3/2001 |
| WO | WO 02055588 A1 | 7/2002 |
| WO | WO 03020828 A1 | 3/2003 |
| WO | WO 03042284 A1 | 5/2003 |
| WO | WO 03093349 A1 | 11/2003 |
| WO | WO 03093369 A1 | 11/2003 |
| WO | WO 2004024798 A1 | 3/2004 |
| WO | WO 2004046226 A1 | 6/2004 |
| WO | WO 2004058857 A2 | 7/2004 |
| WO | WO 2004058858 A1 | 7/2004 |
| WO | WO 2005023934 A1 | 3/2005 |
| WO | WO 2005100444 A1 | 10/2005 |
| WO | WO 2006071772 A2 | 7/2006 |
| WO | WO 2006090478 A1 | 8/2006 |
| WO | WO 2007061623 A1 | 5/2007 |
| WO | WO 2007109240 A2 | 9/2007 |
| WO | WO 2008123318 A1 | 10/2008 |
| WO | WO 2009006091 A2 | 1/2009 |
| WO | WO 2010074296 A1 | 7/2010 |
| WO | WO 2011028765 A1 | 3/2011 |
| WO | WO 2011028770 A1 | 3/2011 |
| WO | WO 2011/049248 * | 4/2011 |
| WO | WO 2011049246 A1 | 4/2011 |
| WO | WO 2011049247 A1 | 4/2011 |
| WO | WO 2011049248 A1 | 4/2011 |
| WO | WO 2011136397 A1 | 11/2011 |

(56) References Cited

FOREIGN PATENT DOCUMENTS

| WO | WO 2012165233 A1 | 12/2012 |
| WO | WO 2012165235 A1 | 12/2012 |
| WO | WO 2012165237 A1 | 12/2012 |
| WO | WO 2013100207 A1 | 7/2013 |

OTHER PUBLICATIONS

English language abstract for JP S5541210 extracted from JPO database, 3 pages.
English language abstract not found for JP S594446; however, see English language equivalent US 4,222,952. Original document extracted from espacenet.com database on May 19, 2014, 15 pages.
English language abstract for JP S6018525 extracted from espacenet.com database on May 8, 2014, 7 pages.
English language abstract for JP S6268820 extracted from espacenet.com database on May 8, 2014, 4 pages.
English language abstract for JP S63139106 extracted from espacenet.com database on May 8, 2014, 10 pages.
English language abstract for JP S63248410 extracted from espacenet.com database on May 8, 2014, 7 pages.
English language abstract for JP H01152158 extracted from espacenet.com database on May 9, 2014, 13 pages.
English language abstract for JP H01207354 extracted from espacenet.com database on May 12, 2014, 10 pages.
English language abstract for JP H0243263 extracted from espacenet.com database on May 12, 2014, 13 pages.
English language abstract for JP H02302438 extracted from espacenet.com database on May 9, 2014, 7 pages.
English language abstract for JP H04272932 extracted from espacenet.com database on May 12, 2014, 8 pages.
English language abstract for JP H05140320 extracted from PAJ database on May 12, 2014, 1 page. English language machine translation extracted from JPO, 21 pages.
English language abstract for JP H05186596 extracted from PAJ database on May 9, 2014, 1 page. English language machine translation extracted from JPO, 32 pages.
English language abstract for JP H06040847 extracted from PAJ database on May 12, 2014, 1 page. English language machine translation extracted from JPO, 21 pages.
English language abstract for JP H06040848 extracted from PAJ database on May 12, 2014, 1 page. English language machine translation extracted from JPO, 22 pages.
English language abstract for JP H07041417 extracted from PAJ database on May 9, 2014, 1 page. English language machine translation extracted from JPO, 18 pages.
English language abstract for JP H07185212 extracted from PAJ database on May 9, 2014, 1 page. English language machine translation extracted from JPO, 20 pages.
English language abstract and machine translation for JP H07187945 extracted from espacenet.com database on May 14, 2014, 52 pages.
English language abstract for JP H07292119 extracted from PAJ database on May 9, 2014, 2 pages. English language machine translation extracted from JPO, 34 pages.
English language abstract for JP H07330907 extracted from PAJ database on May 9, 2014, 1 page. English language machine translation extracted from JPO, 16 pages.
English language abstract for JP H08000908 extracted from PAJ database on May 9, 2014, 1 page. English language machine from JPO, 16 pages.
English language abstract for JP H09071504 extracted from PAJ database on May 14, 2014, 1 page. English language machine translation extracted from JPO, 15 pages.
English language abstract for JP H09165315 extracted from PAJ database on May 9, 2014, 1 page. English language machine translation extracted from JPO, 25 pages.
English language abstract for JP H09165318 extracted from PAJ database on May 9, 2014, 1 page. English language machine translation extracted from JPO, 25 pages.
English language abstract and machine translation for JP H10316536 extracted from espacenet.com database on May 14, 2014, 21 pages.
English language abstract for JP H11049957 extracted from PAJ database on May 12, 2014, 1 page. English language machine translation extracted from JPO, 16 pages.
English language abstract for JP 400932 extracted from espacenet.com database on May 13, 2014, 2 pages. English language machine translation extracted from JPO, 73 pages.
English language abstract for JP 2000038450 extracted from espacenet.com database on May 9, 2014, 13 pages.
English language abstract and machine translation for JP 2000063225 extracted from PAJ database on May 9, 2014, 36 pages.
English language abstract for JP 2000086702 extracted from PAJ database on May 9, 2014, 26 pages.
English language abstract for JP 2000319515 extracted from PAJ database on May 12, 2014, 1 page. English language machine translation extracted from JPO, 32 pages.
English language abstract not found for JP 2000509761; however, see English language equivalent US 6,239,244. Original document extracted from espacenet.com database on May 9, 2014, 22 pages.
English language abstract for JP 2001064513 extracted from PAJ database on May 12, 2014, 1 page. English language machine translation extracted from JPO, 23 pages.
English language abstract for JP 2001115390 extracted from PAJ database on May 9, 2014, 1 page. English language machine translation extracted from JPO, 20 pages.
English language abstract and machine translation for JP 2001187842 extracted from PAJ database on May 12, 2014, 22 pages.
English language abstract for JP 2001192459 extracted from PAJ database on May 12, 2014, 1 page. English language machine translation extracted from JPO, 17 pages.
English language abstract for JP 2001294755 extracted from espacenet.com database on May 9, 2014, 12 pages.
English language abstract not found for JP 2001512164; however, see English language equivalent WO 99/06473. Original document extracted from espacenet.com database on May 9, 2014, 68 pages.
English language abstract for JP 2002105318 extracted from PAJ database on May 12, 2014, 1 page. English language machine translation extracted from JPO, 69 pages.
English language abstract for JP 2002119840 extracted from PAJ database on May 9, 2014, 1 page. English language machine translation extracted from JPO, 14 pages.
English language abstract for JP 2002179798 extracted from PAJ database on May 9, 2014, 2 pages. English language machine translation extracted from JPO, 55 pages.
English language abstract and translation for JP 2003146991 extracted from PAJ database on May 9, 2014, 23 pages.
English language abstract for JP 2004169015 extracted from espacenet.com database on May 14, 2014, 43 pages.
English language abstract and translation for JP 2004174495 extracted from PAJ database on May 9, 2014, 43 pages.
English language abstract and translation for JP 2005120293 extracted from PAJ database on May 9, 2014, 117 pages.
English language abstract not found for JP 2005523980; however, see English language equivalent WO 03/093349. Original document extracted from espacenet.com database on May 9, 2014, 45 pages.
English language abstract not found for JP 2005529989; however, see English language equivalent WO 03/093369. Original document extracted from espacenet.com database on May 9, 2014, 54 pages.
English language abstract not found for JP 2006511645; however, see English language equivalent WO 2004/058858. Original document extracted from espacenet.com database on May 9, 2014, 34 pages.
English language abstract not found for JP 2006511646; however, see English language equivalent WO 2004/058857. Original document extracted from espacenet.com database on May 9, 2014, 30 pages.
English language abstract and machine translation for JP2007126359 extracted from espacenet.com database on May 14, 2014, 49 pages.
English language abstract not found for JP 2007504312; however, see English language equivalent WO 2005/023934. Original document extracted from espacenet.com database on May 9, 2014, 26 pages.

(56) References Cited

OTHER PUBLICATIONS

English language abstract not found for JP 2007532754; however, see English language equivalent WO 2005/100444. Original document extracted from espacenet.com database on May 9, 2014, 39 pages.
English language abstract for JP 2008115358 extracted from PAJ database on May 12, 2014, 1 page. English language machine translation extracted from JPO database, 146 pages.
English language abstract for JP 2008274241 extracted from PAJ database on May 12, 2014, 1 page. English language machine translation extracted from JPO database, 49 pages.
English language abstract not found for JP 2008525598; however, see English language equivalent WO 2006/071772. Original document extracted from espacenet.com database on May 9, 2014, 35 pages.
English language abstract not found for JP 2008542010; however, see English language equivalent US 2008/0200608. Original document extracted from espacenet.com database on May 9, 2014, 24 pages.
English language abstract for JP2009262080 extracted from PAJ database on May 12, 2014, 1 pages. Machine translation extracted from JPO database, 52 pages.
English language abstract and machine translation for JP2010120913 extracted from espacenet.com database on May 14, 2014, 24 pages.
English language abstract for JP2010144156 extracted from espacenet.com database on May 14, 2014, 43 pages.
English language abstract and machine translation for JP2011049248 extracted from espacenet.com database on May 14, 2014, 25 pages.
English language abstract and machine translation for JP2011121095 extracted from espacenet.com database on May 14, 2014, 27 pages.
English language abstract and machine translation for JP2011121097 extracted from espacenet.com database on May 14, 2014, 18 pages.
English language abstract for JP 2011246705 extracted from espacenet.com database on May 9, 2014, 55 pages.
English language abstract for JP 2012246446 extracted from PAJ database on May 14, 2014, 1 page. English language machine translation extracted from JPO database, 278 pages.
English language abstract for WO 02/055588 extracted from espacenet.com database on May 9, 2014, 67 pages.
English language abstract for WO 03/020828 extracted from espacenet.com database on May 12, 2014, 65 pages.
English language abstract for WO 2004/024798 extracted from espacenet.com database on May 12, 2014, 75 pages.
English language abstract for WO 2004/046226 extracted from espacenet.com database on May 9, 2014, 43 pages.
English language abstract for WO 2006/090478 extracted from espacenet.com database on May 12, 2014, 94 pages.
English language abstract for WO 2008/123318 extracted from espacenet.com database on May 9, 2014, 40 pages. Also see English equivalent US 8288498.
English language abstract for WO 2011/049246 extracted from espacenet.com database on May 14, 2014, 103 pages.
English language abstract for WO 201/1049247 extracted from espacenet.com database on May 12, 2014, 168 pages.
English language abstract for WO 2011/049248 extracted from espacenet.com database on May 14, 2014, 224 pages.
English language abstract for WO 2012/165233 extracted from espacenet.com database on May 14, 2014, 155 pages.
English language abstract for WO 2012/165235 extracted from espacenet.com database on May 14, 2014, 160 pages.
English language abstract for WO 2012/165237 extracted from espacenet.com database on May 14, 2014, 82 pages.
International Search Report for Application No. PCT/JP2012/063086, dated Aug. 28, 2012, 6 pages.
International Search Report for Application No. PCT/JP2012/063089, dated Sep. 4, 2012, 6 pages.
International Search Report for Application No. PCT/JP2012/063074, dated Sep. 11, 2012, 8 pages.
International Search Report for Application No. PCT/JP2012/063093, dated Aug. 28, 2012, 5 pages.
Original document and English language abstract for AT 312121 not found; however see English language equivalent US 6,677,446.
English language translation only for AT 356845 extracted from espacenet.com database on Jun. 9, 2014, 13 pages.
Original document and English language abstract for AT 526365 not found; however see English language equivalent US 2008/0138386.
Original document and English language abstract for AU 4734599 not found; however see English language equivalent US 6,677,446.
English language abstract not found for CA 2281973; however see English language equivalent US 6,677,446. Original document extracted from espacenet.com database one Jun. 9, 2014, 55 pages.
English language abstract for CN 101084275 extracted from espacenet.com database on Jun. 9, 2014, 40 pages.
English language abstract for CN 102257040 extracted from espacenet.com database on Jun. 10, 2014, 43 pages.
English language abstract not found for DE 3881647; however see English language equivalent US 4,940,751. Original document extracted from espacenet.com database one Jun. 9, 2014, 25 pages.
English language abstract for DE 19711314 extracted from espacenet.com database on Jun. 9, 2014, 9 pages.
English language abstract not found for DE 60218891; however see English language equivalent US 2005/0043365. Original document extracted from espacenet.com database one Jun. 9, 2014, 14 pages.
English language abstract not found for DE 69928733; however see English language equivalent US 6,677,446. Original document extracted from espacenet.com database one Jun. 9, 2014, 33 pages.
English language abstract not found for DE 112008000839; however see English language equivalent US 2010/0113731. Original document extracted from espacenet.com database one Jun. 9, 2014, 24 pages.
English language abstract not found for DK 0985682; however see English language equivalent US 6,677,446. Original document extracted from espacenet.com database one Jun. 10, 2014, 52 pages.
English language abstract for EP 0317377 extracted from espacenet.com database on Jun. 10, 2014, 12 pages.
English language abstract for EP 0985682 extracted from espacenet.com database on Jun. 10, 2014, 34 pages.
English language abstract not found for ES 2252924; however see English language equivalent US 6,677,446. Original document extracted from espacenet.com database one Jun. 10, 2014, 30 pages.
English language abstract not found for FR 2622201; however see English language equivalent US 4,940,751. Original document extracted from espacenet.com database one Jun. 10, 2014, 25 pages.
English language abstract not found for FR 2784108; however see English language equivalent US 6,677,446. Original document extracted from espacenet.com database one Jun. 10, 2014, 53 pages.
English language abstract not found for JP 4187198; however see English language equivalent US 2003/158363. Original document extracted from espacenet.com database one Jun. 10, 2014, 33 pages.
English language abstract for KR 20040038865 extracted from espacenet.com database on Jun. 10, 2014, 43 pages.
English language abstract for KR 20080042784 extracted from espacenet.com database on Jun. 10, 2014, 54 pages.
English language abstract not found for KR 20110087330; however see English language equivalent US 2011/0251417. Original document extracted from espacenet.com database one Jun. 10, 2014, 40 pages.
English language abstract not found for No. 994411; however see English language equivalent US 6,677,446. Original document extracted from espacenet.com database one Jun. 9, 2014, 41 pages.
English language abstract for WO 98/41579 extracted from espacenet.com database on Jun. 10, 2014, 25 pages.
English language abstract for CN 101641396 extracted from epsacenet.com database on Jun. 9, 2014, 37 pages.

* cited by examiner

ORGANO POLYSILOXANE ELASTOMER AND USE THEREFOR

RELATED APPLICATIONS

This application is the National Stage of International Patent Application No. PCT/JP2012/063074, filed on May 22, 2012, which claims priority to and all the advantages of Japanese Patent Application No. JP 2011-121097, filed on May 30, 2011, the content of which is incorporated herein by reference.

TECHNICAL FIELD

The present invention relates to a novel organopolysiloxane elastomer having a crosslinked structure and uses thereof. Furthermore, the applications and background technology of the novel organopolysiloxane elastomer of the present invention are shared with another patent application asserting a priority right based on Japanese Patent Application No. 2011-121097 (relating to a sugar alcohol-modified organopolysiloxane elastomer and a mono-/di-glycerin derivative-modified organopolysiloxane elastomer) filed on the same day as the present application, and the entire contents of which are hereby incorporated by reference.

BACKGROUND ART

As an organopolysiloxane elastomer having a hydrophilic group, a silicone polymer that is swellable in silicone oil, and a paste-like silicone composition has been reported that is capable of being produced using such a silicone polymer and that is capable of being uniformly and stably dispersed in water have been reported (e.g. see Patent Document 1 and 2 or the like). However, the emulsification ability and particularly the emulsification ability in non-silicone oils of such paste-like silicone compositions have not been sufficiently satisfactory, and the feel-improving effect of such compositions in cosmetics has been insufficient.

Meanwhile, numerous technologies have been reported as technologies related to organopolysiloxane elastomers not having a hydrophilic group (see Patent Documents 3 to 6 or the like). However, there have been no reports heretofore of organopolysiloxane elastomers that have a branched structure by silylalkyl groups having a siloxane dendron structure, and the effects thereof, as well as application to cosmetics and external use preparations, are unknown.

BACKGROUND DOCUMENTS

Patent Documents

Patent Document 1: Japanese Unexamined Patent Application Publication No. H04-272932A
Patent Document 2: Japanese Unexamined Patent Application Publication No. H05-104320A
Patent Document 3: Japanese Unexamined Patent Application Publication No. H01-207354A
Patent Document 4: Japanese Unexamined Patent Application Publication No. H02-043263A
Patent Document 5: WO/2007/109240
Patent Document 6: WO/2009/006091

SUMMARY OF THE INVENTION

Technical Problem

Consequently, there is a demand in cosmetic applications for organopolysiloxane elastomers not having a hydrophilic group, and particularly for organopolysiloxane elastomers with a branched structure by silylalkyl groups having a siloxane dendron structure.

Requests for "PEG-free formulations" have increased in recent years. For example, in Germany, the demand to replace raw materials having polyether groups with non-polyether raw materials has increased due to a negative perception of the safety of products that contain polyethylene glycol (PEG) due to testing done by a consumer information magazine company. Moreover, in South Korea, increased interest in non-polyether silicone surfactants has emerged due to a concern that products containing PEG may irritate the skin because formalin may be produced as a result of oxidation degradation of PEG.

Assuming, in light of the above, a global trend to revise the formulation of end consumer products, such as cosmetic products and the like, to completely PEG-free formulations, market needs are anticipated in response to this trend that will cause technology, even in the field of silicone-based surfactants, to evolve from the conventional polyether-modified silicone or polyether-modified silicone elastomers to non-polyether hydrophilic silicones or non-polyether hydrophilic silicone elastomers. Also, glycerin-modified silicones or glycerin-modified silicone elastomers are considered to have superior oxidation stability compared to polyether-modified silicones or polyether-modified silicone elastomers, and thus hold promise as such non-polyether hydrophilic silicones or non-polyether hydrophilic silicone elastomers.

However, conventional glycerin-modified silicones or glycerin-modified silicone elastomers have been expensive and have had other major problems. Namely, while there is a demand for use of these silicones and elastomers as emulsions, they are unable to withstand use in actual cosmetic formulations due to their low emulsifying ability. Consequently, there has been no choice but to use the glycerin-modified silicones or glycerin-modified silicone elastomers in combination with the more reliable emulsifiers that are polyether-modified silicones or polyether-modified silicone elastomers, making it difficult to revise cosmetics to completely PEG-free formulations.

The present invention is developed in order to solve the aforementioned problems. The first object of the present invention is to provide a novel organopolysiloxane elastomer and production method thereof, where the organopolysiloxane elastomer has compatibility with various types of oil agents, has excellent structural control properties and gelling properties, has further excellent lasting feel (in particular, a smooth and thick velvety sensation), that further has no stickiness whatsoever from the time of initial application until after drying, and that further has excellent beautifying effects such as wrinkle concealment (masking effect) or the like.

The second object of the present invention is to provide a novel glycerin derivative-modified organopolysiloxane elastomer, and production method thereof, which while providing all the properties, further has an excellent moisturizing effect and emulsification properties, and which is able to form stable emulsions not only with silicone oils (low polarity oils) and ester oils (intermediate-to-high polarity oils), which are readily and stably emulsified using silicone surfactants, but also with hydrocarbon oils (non-polar oils), which had been particularly difficult to emulsify using conventional non-polyether type silicone surfactants, so that it becomes possible to expand the range of formulations according to purposes, e.g. cosmetics, external use preparations, or the like.

A third object of the present invention is to provide a raw material for an external use preparation or cosmetic, such as a gelling agent, structuring agent, thickener, tactile sensation improver, moisturizing agent, masking agent, surfactant, emulsifier, powder dispersion stabilizer, or the like, that contains the organopolysiloxane elastomer and/or glycerin derivative-modified organopolysiloxane elastomer, as well as to provide a cosmetic or external use preparation containing the organopolysiloxane elastomer.

A fourth object of the present invention is to provide an external use preparation or cosmetic that, by using a raw material for an external use preparation or cosmetic that contains the organopolysiloxane elastomer and/or glycerin derivative-modified organopolysiloxane elastomer, conforms to the global trend to revise the formulations of end consumer products, such as cosmetic products and the like, to be completely PEG-free formulations, which do not contain compounds that include a polyoxyethylene region.

A fifth object of the present invention is to provide an organopolysiloxane elastomer and/or glycerin derivative-modified organopolysiloxane elastomer of reduced odor, a raw material for an external use preparation or cosmetic that contains such an organopolysiloxane elastomer and/or glycerin derivative-modified organopolysiloxane elastomer, and an external use preparation or cosmetic that contains such a raw material.

Solution to Problem

The present inventors arrived at the present invention as a result of conducting dedicated research in order to achieve the objective described above. Namely, a first object of the present invention can be achieved by an organopolysiloxane elastomer comprising a group having a siloxane dendron structure represented by $L^1$ that is bonded to a silicon atom, and having a crosslinked structure that includes a carbon-silicon bond in the crosslinking portion. $L^1$ herein is a silylalkyl group having a siloxane dendron structure and represented by the following general formula (2) when i=1:

[Formula 1]

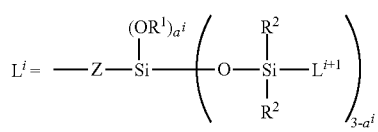

(in the formula, $R^1$ represents a substituted or unsubstituted, straight or branched monovalent hydrocarbon group having from 1 to 30 carbons;

$R^2$ each independently represents an alkyl group or phenyl group having from 1 to 6 carbons;

Z represents a divalent organic group;

i represents a generation of the silylalkyl group represented by $L^i$ and is an integer of 1 to k when k is a number of generations that is a number of repetitions of the silylalkyl group; the number of generations k is an integer from 1 to 10; $L^{i+1}$ is the silylalkyl group when i is less than k, and $R^2$ when i=k, and $a^i$ is a number in a range of 0 to 3.

It is preferred that $L^1$ in the general formula (2) is a functional group represented by the following general formula (2-1) or general formula (2-2):

General Formula (2-1):

[Formula 2]

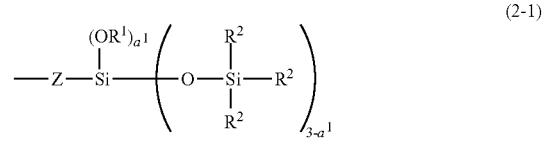

General Formula (2-2):

[Formula 3]

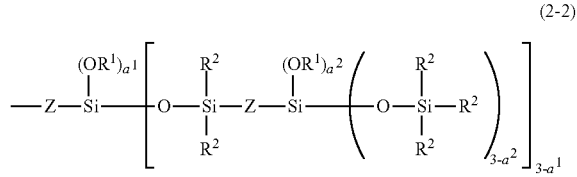

(in the formula, $R^1$, $R^2$, and Z are the same groups described above, and $a^1$ and $a^2$ are each independently numbers in a range of 0 to 3).

A second object of the present invention can be achieved by an organopolysiloxane elastomer having a crosslinked structure comprising a group having a siloxane dendron structure represented by $L^1$ that is bonded to the silicon atom and a hydrophilic group represented by Q that is bonded to a different silicon atom from the silicon atom (for convenience, referred to in some cases hereafter as the "glycerin derivative group"), and has a carbon-silicon bond in the crosslinking portion. Q herein is a hydrophilic group that is bonded to silicon atoms via a linking group that is at least divalent, and that includes at least one hydrophilic unit selected from hydrophilic units represented by the following general formulae (3-1) to (3-4):

$$-C_rH_{2r}-O- \quad (3\text{-}1)$$

(in the formula, r is a number in a range of 1 to 6);

[Formula 4]

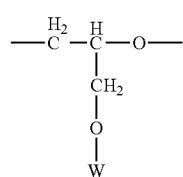

(in the formula, W represents a hydrogen atom or an alkyl group having from 1 to 20 carbons);

[Formula 5]

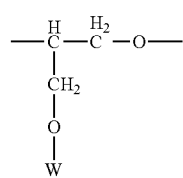

(in the formula, W is synonymous with the groups described above); and

[Formula 6]

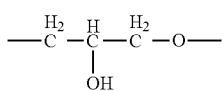 (3-4)

It is preferred that Q has a linear hydrophilic segment formed by linearly bonding a plurality of hydrophilic units, or has a branched hydrophilic segment formed by branched bonding a plurality of the hydrophilic units via at least one type of branch unit selected from groups represented by the following structural formulae (3-5) to (3-7):

[Formula 7]

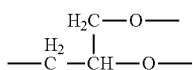 (3-5)

[Formula 8]

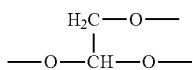 (3-6)

[Formula 9]

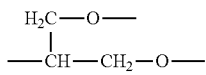 (3-7)

It is more preferable that Q is a hydrophilic group represented by any of the following general formulae (4-1) to (4-4).

General Formula (4-1):

$$-R^3(-O-X^1{}_m-R^4)_p \quad (4-1)$$

(in the formula,
$R^3$ is an organic group having (p+1) valency;
p is a number in a range of 1 to 3;
$X^1$ are each independently at least one hydrophilic unit selected from the hydrophilic units represented by the general formulae (3-1) to (3-4) above;
m is a number in a range of 1 to 100;
$R^4$ is a hydrogen atom or a group selected from the group consisting of glycidyl groups, acyl groups, and alkyl groups having from 1 to 20 carbons)

General Formula (4-2):

$$-R^3(-O-X^2)_p \quad (4-2)$$

(in the formula,
$R^3$ is synonymous with the groups described above;
p is the same number as described above, and
$X^2$ is a hydrophilic group represented by the following structural formula (4-2-1):

[Formula 10]

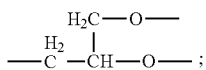 (4-2-1)

(in the formula, at least one hydrophilic unit selected from the hydrophilic units represented by the general formulae (3-1) to (3-4) above is independently bonded to each of the two oxygen atoms))

General Formula (4-3):

$$-R^3(-O-X^3)_p \quad (4-3)$$

(in the formula,
$R^3$ is synonymous with the groups described above;
p is the same number as described above, and
$X^3$ is a hydrophilic group represented by the following structural formula (4-3-1):

[Formula 11]

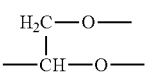 (4-3-1)

(in the formula, at least one hydrophilic unit selected from the hydrophilic units represented by the general formulae (3-1) to (3-4) above is independently bonded to each of the two oxygen atoms)

General Formula (4-4):

$$-R^3(-O-X^4)_p \quad (4-4)$$

(in the formula,
$R^3$ is synonymous with the groups described above;
p is the same number as described above, and
$X^4$ is a hydrophilic group represented by the following structural formula (4-4-1):

[Formula 12]

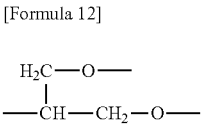 (4-4-1)

(in the formula, at least one hydrophilic unit selected from the hydrophilic units represented by the general formulae (3-1) to (3-4) above is independently bonded to each of the two oxygen atoms)

The organopolysiloxane elastomer of the present invention can be obtained by causing reactions between at least the following:
(A) an organohydrogenpolysiloxane;
(B) a siloxane dendron having one reactive unsaturated group in a molecule; and
(C) at least one organic compound selected from the group consisting of (C1) organic compounds having an average of more than one reactive unsaturated groups in a molecule, and (C2) organic compounds having at least one reactive unsaturated group and at least one epoxy group in a molecule.

Additionally, a preferred organopolysiloxane elastomer of the present invention can be obtained by causing reactions between at least the following:
(A) an organohydrogenpolysiloxane;
(B) a siloxane dendron having one reactive unsaturated group in a molecule;
(C) at least one organic compound selected from the group consisting of (C1) organic compounds having an average of more than one reactive unsaturated groups in a molecule, and (C2) organic compounds having at least one reactive unsaturated group and at least one epoxy group in a molecule (provided that (C) is optional in cases where the below described (D) has an average of more than one reactive unsaturated group in a molecule); and (D) a hydrophilic derivative having a reactive unsaturated group and a hydrophilic group that includes at least one hydrophilic unit selected from the hydrophilic units represented by the structural formulae (3-1) to (3-4).

It is preferred that the average number of silicon-bonded hydrogen atoms in a molecule of the component (A) that react with the unsaturated groups in the component (C) and/or component (D) that constitute the crosslinking portion is 0.1 or greater.

The component (A) preferably is represented by average composition formula (1):

$$R^5_a H_b SiO_{(4-a-b)/2} \quad (1)$$

(in the formula,
$R^5$ is each independently a monovalent organic group, wherein $1.0 \le a \le 3.0$ and $0.001 \le b \le 1.5$).

It is preferred that the component (B) is a compound having a siloxane dendron structure with single carbon-carbon double bond at a molecular terminal, represented by the following general formula (2'):

[Formula 13]

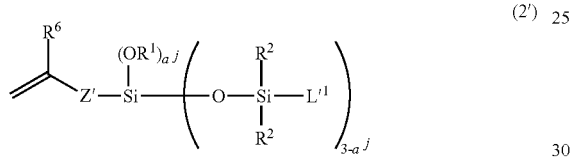

(2')

(in the formula,
$L^1$ is an alkyl group or phenyl group having from 1 to 6 carbons or, when j=1, is a silylalkyl group represented by following general formula (2"):

[Formula 14]

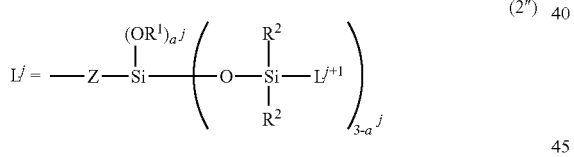

(2")

(in the formula,
$R^2$ is an alkyl group or phenyl group having from 1 to 6 carbons;
Z is a divalent organic group;
j represents the number of generations of the silylalkyl group that is represented by $L^j$, when the number of generations (the number of repetitions) of the silylalkyl group is k', j is an integer from 1 to k', and the number of generations k' is an integer from 1 to 10; $L^{j+1}$ is the silylalkyl group when j is less than k' and is the $R^2$ when j=k'; and
$a^j$ is a number in a range of 0 to 3),
Z' is a divalent organic group, and
$R^6$ is a hydrogen atom or methyl group).

The component (C) preferably is at least one organic compound selected from the following formulae (C1-1) to (C1-5) and (C2-1) to (C2-2):
(C1-1) an α,ω-diene represented by the general formula (5-1):

$$CH_2=CH(CH_2)_xCH=CH_2 \quad (5-1)$$

(in the formula, $1 \le x \le 20$);

(C1-2) an α,ω-diyne represented by the general formula (5-2):

$$CH\equiv C(CH_2)_xC\equiv CH \quad (5-2)$$

(in the formula, $1 \le x \le 20$);
(C1-3) an α,ω-ene-yne represented by the general formula (5-3):

$$CH_2=CH(CH_2)_xC\equiv CH \quad (5-3)$$

(in the formula, $1 \le x \le 20$);
(C1-4) a bisalkenyl polyether compound represented by the general formula (5-4):

$$C_qH_{2q-1}O(C_nH_{2n}O)_yC_qH_{2q-1} \quad (5-4)$$

(in the formula, $2 \le q \le 20$ and $2 \le n \le 4$; y is the total number of repetitions of oxyethylene units, oxypropylene units, and oxybutylene units, and $1 \le y \le 180$);
(C1-5) unsaturated group-containing silicone compound represented by the average composition formula (5-5):

$$R^7_c R^8_d SiO_{(4-c-d)/2} \quad (5-5)$$

(wherein, $R^7$ may each independently represent a monovalent organic group that differs from $R^8$;
$R^3$ is each independently a monovalent unsaturated aliphatic hydrocarbon group having from 2 to 30 carbons, $1.0 \le c \le 2.5$, and $0.001 \le d \le 1.5$);
(C2-1) an unsaturated epoxy compound represented by general formula (5-6):

[Formula 15]

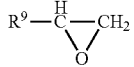

(5-6)

(in the formula, $R^9$ is a substituted or unsubstituted, straight or branched monovalent hydrocarbon group having one unsaturated bond and from 2 to 20 carbons); and
(C2-2) an unsaturated group-containing alicyclic epoxy compound represented by general formula (5-7):

[Formula 16]

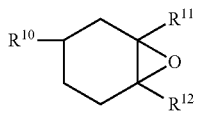

(5-7)

(in the formula, $R^{10}$ represents a substituted or unsubstituted, straight or branched monovalent hydrocarbon group having one unsaturated bond and from 2 to 20 carbons;
$R^{11}$ represents a hydrogen atom or methyl group; and
$R^{12}$ represents a hydrogen atom or methyl group).

It is preferred that the monovalent organic group represented by $R^5$ in the average composition formula (1) is selected from following (E1) to (E9):
(E1) a substituted or unsubstituted, straight or branched monovalent hydrocarbon group having from 1 to 60 carbons;
(E2) a polyoxyalkylene group represented by —$R^{13}$O(AO)$_z R^{14}$ (in the formula, AO is an oxyalkylene group having from 2 to 4 carbons, $R^{13}$ is a substituted or unsubstituted, straight or branched divalent hydrocarbon group having from 3 to 5 carbons, $R^{14}$ is a hydrogen atom, a substituted or unsubstituted, straight or branched monovalent hydrocarbon group having from 1 to 24 carbons, or a substituted or unsubstituted, straight or branched acyl group having from 2 to 24 carbons, and z=1 to 100);
(E3) a substituted or unsubstituted, straight or branched alkoxy group having from 1 to 30 carbons;
(E4) a hydroxyl group;
(E5) an ester group represented by —$R^{15}$—$COOR^{16}$ (in the formula, $R^{15}$ represents a substituted or unsubstituted, straight or branched divalent hydrocarbon group having from 2 to 20 carbons, and $R^{16}$ represents a substituted or unsubstituted, straight or branched monovalent hydrocarbon group having from 1 to 30 carbons);
(E6) an ester group represented by —$R^{17}$—$OCOR^{18}$ (in the formula, $R^{17}$ represents a substituted or unsubstituted, straight or branched divalent hydrocarbon group having from 2 to 20 carbons, and $R^{18}$ represents a substituted or unsubstituted, straight or branched monovalent hydrocarbon group having from 1 to 30 carbons);
(E7) an alkyl group substituted with a polysiloxane chain structure and represented by the following general formula (6):

[Formula 17]

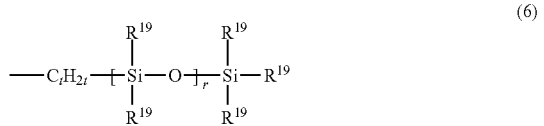
(6)

(in the formula, $R^{19}$ is each independently a substituted or unsubstituted, straight or branched monovalent hydrocarbon group having from 1 to 30 carbons, a hydroxyl group, or hydrogen atom, at least one of the $R^{19}$ being the monovalent hydrocarbon group; t is a number in a range of 2 to 10; and r is a number in a range of 1 to 100);
(E8) an epoxy group represented by the following general formula (7):

[Formula 18]

(7)

(in the formula, $R^{20}$ represents a substituted or unsubstituted, straight or branched divalent hydrocarbon group having from 2 to 20 carbons); and
(E9) an alicyclic epoxy group represented by the following general formula (8):

[Formula 19]

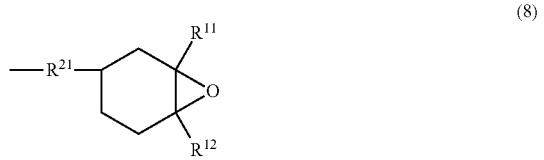
(8)

(in the formula, $R^{21}$ represents a substituted or unsubstituted, straight or branched divalent hydrocarbon group having from 2 to 20 carbons; and $R^{11}$ and $R^{12}$ are synonymous with those described above).

It is preferred that the organopolysiloxane elastomer of the present invention is in the form of a powder, and more preferably the form of a powder with a volume average particle size in a range of 20 to 1,000 um.
It is preferred that the organopolysiloxane elastomer of the present invention is swellable and contains a quantity of oil agent greater than or equal to its own weight.
Furthermore, the first object of the present invention can be achieved by an organopolysiloxane elastomer production method comprising a step of causing reactions between at least the following:
(A) an organohydrogenpolysiloxane;
(B) a siloxane dendron having one reactive unsaturated group in a molecule; and
(C) at least one organic compound selected from the group consisting of (C1) organic compounds having an average of more than one reactive unsaturated groups in a molecule, and (C2) organic compounds having at least one reactive unsaturated group and at least one epoxy group in a molecule.
In the organopolysiloxane elastomer production method, it is preferred that some or all of the reactions are performed in the presence of no solvent or in the presence of at least one solvent selected from a group represented by (P-1) to (P-2) below:
(P-1): an organic compound; and
(P-2): a compound having a silicon atom.
One embodiment of the organopolysiloxane elastomer production method is characterized in that the (A) and (B) are reacted first, and then (C) is added and a crosslinking reaction is performed, but the optional component (Q) shown below can be reacted with (A) before the (A)-(B) reaction, or can be further reacted following the (A)-(B) reaction, or can be reacted simultaneous with the (A)-(B) reaction, or can be further reacted following crosslinking by (C).
(Q): a compound having one unsaturated group in a molecule (excluding the compound (C2)).
Another embodiment of the organopolysiloxane elastomer production method is characterized in that the reaction between (A) and (C) to introduce crosslinking portions is performed first, after which, (B) is added and reacted, but the optional component (Q) shown below can be reacted with (A) before the (A)-(C) reaction, or can be further reacted following the (A)-(C) reaction, or can be further reacted following the reaction with (B).
(Q): a compound having one unsaturated group in a molecule (excluding the compound of (C2))
Furthermore, the second object of the present invention can be achieved by an organopolysiloxane elastomer production method comprising a step of causing reactions between at least the following:
(A) an organohydrogenpolysiloxane;
(B) a siloxane dendron having one reactive unsaturated group in a molecule;
(C) at least one organic compound selected from the group consisting of (C1) organic compounds having an average of more than one reactive unsaturated groups in a molecule, and (C2) organic compounds having at least one reactive unsaturated group and at least one epoxy group in a molecule (provided that (C) is optional in cases where the below described (D) has an average of more than one reactive unsaturated group in a molecule); and
(D) a hydrophilic derivative having a reactive unsaturated group and a hydrophilic group that includes at least one hydrophilic unit selected from the hydrophilic units represented by the structural formulae (3-1) to (3-4).
In the organopolysiloxane elastomer production method, it is preferred that some or all of the reactions are performed in the presence of at least one solvent selected from a group represented by (P-1) to (P-2) below:
(P-1): an organic compound; and
(P-2): a compound having a silicon atom.

One embodiment of the organopolysiloxane elastomer production method is characterized in that (B) and (D) are successively reacted with the (A) in any order (provided that (D) is limited to compounds having one reactive unsaturated group in a molecule), after which, (C) is added and a crosslinking reaction is performed, but the optional component (Q) shown below can be reacted with (A) before the (A)-(B) reaction or before the (A)-(D) reaction, or can be further reacted following the (A)-(B) reaction or following the (A)-(D) reaction, or can be reacted simultaneous with the (A)-(B) reaction or simultaneous with the (A)-(D) reaction, or can be further reacted following crosslinking by (C).
(Q): a compound having one unsaturated group in a molecule (excluding the compound (C2))

Another embodiment of the organopolysiloxane elastomer production method is characterized in that the reaction between (A) and (C) to introduce crosslinking portions is performed first, after which, (B) and (D) are added and successively reacted in any order (provided that (D) is limited to compounds having one reactive unsaturated group in a molecule), but the optional component (Q) shown below can be reacted with (A) before the (A)-(C) reaction, or can be further reacted following the (A)-(C) reaction, or can be further reacted following the reactions with (B) and (D).
(Q): a compound having one unsaturated group in a molecule (excluding the compound (C2))

A third and/or fourth objects of the present invention may be attained by an external use preparation raw material, cosmetic raw material, external use preparation, or cosmetic comprising the organopolysiloxane elastomer; or by a composition including at least one type of oil agent in addition to the organopolysiloxane elastomer; or by an external use preparation raw material, cosmetic raw material, external use preparation, or cosmetic comprising the composition. The composition preferably is an emulsion or paste.

The external use preparation raw material or cosmetic raw material can be a gelling agent, structuring agent, thickener, tactile sensation improver, moisturizing agent, masking agent, surfactant, emulsifier, or powder dispersion stabilizer.

Although the fourth object of the present invention in particular may be attained with advantage by an external use preparation or cosmetic including the organopolysiloxane elastomer, and preferably including the organopolysiloxane elastomer; however, the external use preparation or cosmetic does not include a compound having an oxyalkylene structure having an average number of repetitions of an oxyalkylene unit of 2 or higher as a hydrophilic group; and the external use preparation or cosmetic particularly preferably does not include a compound having a polyoxyethylene group or polyoxyethylene region.

A fifth object of the present invention may be attained by an organopolysiloxane elastomer obtained by the production method for the organopolysiloxane elastomer, or by the organopolysiloxane elastomer obtained by a process of adding at least one type of acidic substance for treatment to a composition containing at least one type of oil agent as well as the organopolysiloxane elastomer, and heating or reducing pressure to remove volatile components. The fifth object of the present invention may also be attained by a composition of the organopolysiloxane elastomer, or by an external use preparation raw material, cosmetic raw material, external use preparation, or cosmetic including the composition.

Effects of Invention

The present invention can provide a novel organic-modified organopolysiloxane elastomer, which has affinity with various oil agents and superior thickening properties and gelling properties, further provides excellent feel characterized in particular by a thick, velvety smoothness without any tackiness from the time of initial application until after drying, and which excellent feel is provided in a persistent manner.

Moreover, the organic-modified organopolysiloxane elastomer of the present invention is able to bring about excellent cosmetic effects such as a wrinkle-concealing effect, moisturizing effect, and the like.

The organic-modified organopolysiloxane elastomer of the present invention also has excellent emulsification properties, whereby it is possible to realize excellent emulsification performance not only with low polarity silicone oil agents and intermediate-to-high polarity ester oil agents, but also with non-polar hydrocarbon oil agents. Consequently, blending the organic-modified organopolysiloxane elastomer of the present invention into external use preparations or cosmetics makes it possible to design external use preparations or cosmetics of various type of formulations. Furthermore, the external use preparation or cosmetic of the present invention can be an external use preparation or cosmetic that does not have to contain compounds having a polyoxyethylene group or a polyoxyethylene region, e.g., polyether-modified silicones, and so does not include polyoxyethylene regions in response to the global trend to revise the formulations of end consumer products, such as cosmetic products and the like, to be completely PEG-free formulations. The organopolysiloxane elastomer of the present invention can be used to prepare a water-in-oil emulsion cosmetic or the like having sufficient stability, even without combined use with a nonionic surfactant such as a hydrophilic silicone emulsifier or the like having a PEG structure. The formulation of the cosmetic or external use preparation may be formulated as an overall PEG-free formulation (i.e. formulation that does not include a compound having a polyoxyethylene (PEG) structure as a hydrophilic group). Namely, by using the organopolysiloxane elastomer of the present invention, it is possible for the cosmetics industry to realize a highly environmentally compatible business strategy that complies with the worldwide trend to reform the constitution of end consumer products to completely PEG-free formulations.

Furthermore, a composition in which the organic-modified organopolysiloxane elastomer of the present invention has been blended can have both of the contradictory characteristics of an extremely soft feel, while also having a highly viscous nature that can ensure stability. This effect is remarkable when the organic-modified organopolysiloxane elastomer is in the particulate form.

Furthermore, the organic-modified organopolysiloxane elastomer of the present invention has an excellent effect in maintaining the dispersed state of a powder dispersed in a medium, and can particularly improve the storage stability of compositions that contain particles.

Due to the functions of the organic-modified organopolysiloxane elastomer of the present invention, the organic-modified organopolysiloxane elastomer of the present invention can be used suitably as a raw material for an external use preparation or cosmetic such as a thickener, gelling agent, structuring agent, tactile sensation improver, moisturizing agent, masking agent, surfactant, emulsifier, powder dispersion stabilizer, or the like. Moreover, the organic-modified organopolysiloxane elastomer of the present invention can be suitably blended in a cosmetic or external use preparation. In particular, non-aqueous type emulsion compositions of excellent stability that can be used as a drug delivery system can be provided, and water-in-oil or oil-in-water type emulsion compositions of excellent stability can likewise be provided.

Moreover, since the organic-modified organopolysiloxane elastomer of the present invention can be uniformly mixed with a wide variety of oil agents, the organic-modified organopolysiloxane elastomer of the present invention can be used as compositions with various types of oil agents. Furthermore, a composition comprising an oil agent in conjunction with the organic-modified organopolysiloxane elastomer of the present invention also has superior storage stability.

The odor of the organic-modified organopolysiloxane elastomer can be decreased according to the present invention. The odor-reduced organic-modified organopolysiloxane elastomer of the present invention is suitable as a raw material for external use preparations and cosmetics, and is particularly suitable as a component in external use preparations and cosmetics. In particular, the present invention can provide an organic-modified organopolysiloxane elastomer or composition comprising the same, that is substantially odorless or that has suppressed odor emission at high temperatures or with the passage of time, by a simple process, i.e. acidification.

The odor-reducing effect of the organic-modified organopolysiloxane elastomer of the present invention is extremely high, and odor-reducing effect like that obtained in the present invention can not be obtained by applying the acidification like that of the present invention to other modified organopolysiloxane elastomers. The advantage of the present invention is that it can provide a deodorized organic-modified organopolysiloxane elastomer or composition comprising the same, that is beneficial for implementation on an industrial scale, while also being simple and low-cost.

Moreover, when the odor-reduced organic-modified organopolysiloxane elastomer of the present invention is blended in an external use preparation or cosmetic, there is no need to mask the odor, allowing a high degree of freedom in the design of formulations for external use preparations or cosmetics. This is particularly advantageous in cosmetics, in which odor-containing functionality is emphasized.

DETAILED DESCRIPTION OF THE INVENTION (Organopolysiloxane Elastomer and Production Method Thereof)

A first embodiment of the present invention is an organopolysiloxane elastomer containing a compound having a siloxane dendron structure bonded to a silicon atom and represented by $L^1$, and having a three-dimensional crosslinked network structure that includes carbon-silicon bonds in the crosslinked region.

The group represented by $L^1$ is a group with a siloxane dendron structure, which, when i=1, is a silylalkyl group represented by the following general formula (2):

[Formula 20]

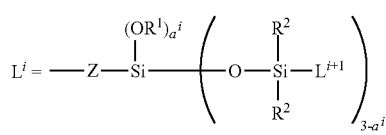

(in the formula,
$R^1$ represents a substituted or unsubstituted, straight or branched monovalent hydrocarbon group having from 1 to 30 carbons,
$R^2$ each independently represents an alkyl group or phenyl group having 1 to 6 carbons;
Z is a divalent organic group;
i represents a generation of the silylalkyl group represented by $L^i$ and is an integer of 1 to k when k is a number of generations that is a number of repetitions of the silylalkyl group; the number of generations k is an integer from 1 to 10; $L^{i+1}$ is the silylalkyl group when i is less than k, and $R^2$ when i=k, and $a^i$ is a number in a range of 0 to 3).

The silylalkyl group having a siloxane dendron structure is a functional group that includes a structure in which carbosiloxane units are spread out in a dendrimer form and manifests high water repellence, and an excellent balance in combination with a hydrophilic group. Additionally, the silylalkyl group having a siloxane dendron structure is chemically stable, and for this reason, the silylalkyl group is a functional group providing advantageous properties such as usability in combination with a wide range of cosmetic compounding components.

Examples of the substituted or unsubstituted, straight or branched monovalent hydrocarbon group having from 1 to 30 carbons (the $R^1$ moieties in general formula (2)) include methyl groups, ethyl groups, propyl groups, butyl groups, pentyl groups, hexyl groups, heptyl groups, octyl groups, and similar alkyl groups; cyclopentyl groups, cyclohexyl groups, and similar cycloalkyl groups; vinyl groups, allyl groups, butenyl groups, and similar alkenyl groups; phenyl groups, tolyl groups, and similar aryl groups; benzyl groups and similar aralkyl groups; and groups wherein the hydrogen atoms bonded to the carbons of these groups are substituted at least partially by fluorine or a similar halogen atom, or an organic group containing an epoxy group, a glycidyl group, an acyl group, a carboxyl group, an amino group, a methacryl group, a mercapto group, or the like (provided that the total number of carbons is from 1 to 30).

Among the phenyl group or the alkyl group having from 1 to 6 carbons represented by $R^2$ in general formula (2), examples of the alkyl group having from 1 to 6 carbons include straight, branched, or cyclic alkyl groups such as methyl, ethyl, n-propyl, i-propyl, n-butyl, i-butyl, s-butyl, pentyl, neopentyl, cyclopentyl, and hexyl.

In cases where i=k in general formula (2), $R^2$ preferably is a methyl group or a phenyl group. In particular, $R^2$ preferably is a methyl group when i=k.

From an industrial perspective, the number of generations k preferably is an integer from 1 to 3, and more preferably is 1 or 2. In each of the number of generations, the group represented by $L^1$ is represented as follows. In the formulae, $R^1$, $R^2$, and Z are the same groups as described above.

When the number of generations is k=1, $L^1$ is represented by the following general formula (2-1).

General Formula (2-1):

[Formula 21]

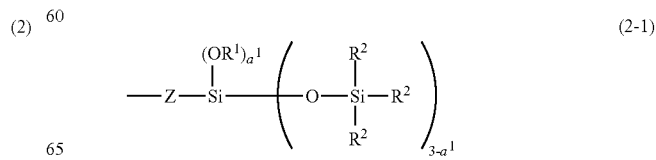

In the formula, $R^1$, $R^2$, and Z are the same groups described above, and $a^1$ is a number in a range of 0 to 3.

When the number of generations is k=2, $L^1$ is represented by the following general formula (2-2).

General Formula (2-2):

[Formula 22]

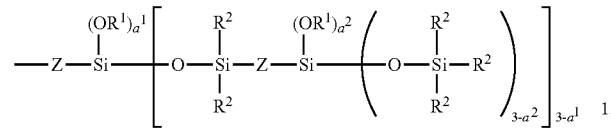

(2-2)

In the formula, $R^1$, $R^2$, and Z are the same groups described above, and $a^1$ and $a^2$ are each independently numbers in a range of 0 to 3.

When the number of generations is k=3, $L^1$ is represented by the following general formula (2-3).

General Formula (2-3):

[Formula 23]

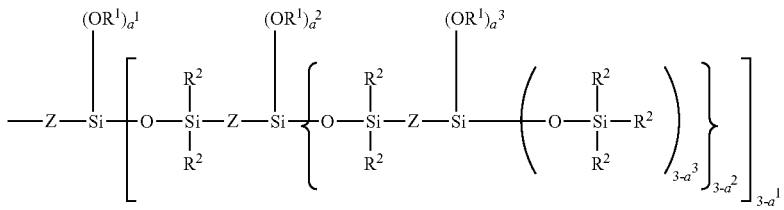

(2-3)

In the formula, $R^1$, $R^2$, and Z are the same groups described above, and $a^1$, $a^2$, and $a^2$ are each independently numbers in a range of 0 to 3.

In cases where the number of generations is from 1 to 3 in a structures represented by formulae (2-1) to (2-3), $a^1$, $a^2$, and $a^3$ are each independently a number in a range of 0 to 3. The values $a^i$ are preferably a number in a range of 0 to 1 and more preferably, $a^i$ is 0.

In general formulae (2) and (2-1) to (2-3), Z are each independently a divalent organic group, and specific examples thereof include a divalent organic group formed by addition-reacting a silicon-bonded hydrogen atom and a functional group having an unsaturated hydrocarbon group such as an alkenyl group, an acryloxy group, a methacryloxy group, or the like at the terminal. The functional group can be appropriately selected according to the method for introducing the silylalkyl group having a siloxane dendron structure, and is not restricted to the functional groups described above. More specifically, Z preferably is each independently a group selected from divalent organic groups represented by the following general formulae: $-R^{22}-$, $-R^{22}-CO-$, $R^{22}-COO-$, $-R^{22}-CONH-$, $-R^{22}-CO-R^{23}-$, $-R^{22}-COO-R^{23}-$, $-R^{22}-CONH-R^{23}-$, $-CO-R^{22}-$, $-COO-R^{22}-$, $-CONH-R^{22}-$, $-R^{23}-CO-R^{22}-$, $-R^{23}-COO-R^{22}-$, $-R^{23}-CONH-R^{22}-$, and $-R^{22}-R^{23}$. Of these, Z in $L^1$ preferably is a divalent organic group represented by $-R^{22}-$ that is introduced by a reaction between a silicon-bonded hydrogen atom and an alkenyl group. Likewise, Z is preferably a divalent organic group represented by general formula $-R^{22}-COO-R^{23}-$ that is introduced by a reaction between a silicon-bonded hydrogen atom and an unsaturated carboxylic ester group. On the other hand, in the silylalkyl group represented by $L^i$ in which the number of generations k is 2 or more, and $L^i$ is $L^2$ to $L^k$, Z is preferably an alkylene group having from 2 to 10 carbons, more preferably a group selected from an ethylene group, a propylene group, a methylethylene group, and a hexylene group, and most preferably an ethylene group.

In the general formulae described above, $R^{22}$ may have a substituent, and are each independently a straight or branched-chain alkylene group or alkenylene group having from 2 to 22 carbons, or an arylene group having from 6 to 22 carbons. More specifically, examples of $R^{22}$ include an ethylene group, a propylene group, a butylene group, a hexylene group, and similar straight alkylene groups; a methylmethylene group, a methylethylene group, a 1-methylpentylene group, a 1,4-dimethylbutylene group, and similar branched alkylene groups. $R^{22}$ is preferably a group selected from an ethylene group, a propylene group, a methylethylene group, and a hexylene group.

In the general formulae described above, $R^{23}$ is a group selected from divalent organic groups represented by the following formula.

[Formula 24]

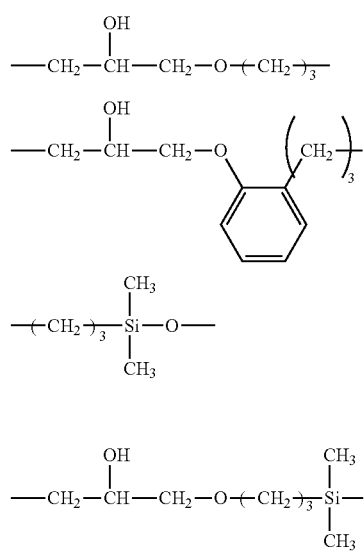

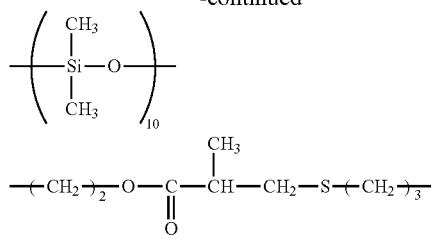

The organopolysiloxane elastomer of the present invention preferably is an elastomer with a relatively high crosslinking density, and preferably is a gel-like, rubber-like, or powdered solid that is insoluble in solvents and the like. The organopolysiloxane elastomer of the present invention preferably has no flowability (is in a non-liquid state) at 25° C. The expression "has no flowability at 25° C." is taken to mean that, once the organopolysiloxane elastomer has been introduced into a specified container and the surface of the organopolysiloxane elastomer leveled using a trowel or like tool, and then the container is tilted, the surface will not return to level after 24 hours. Here, the term "level" is taken to mean forming a flat surface that is perpendicular to the direction of action of gravity.

Moreover, preferably, the organopolysiloxane elastomer of the present invention has a three-dimensional crosslinked network structure provided with a crosslinking portion that includes a carbon-silicon bond. The crosslinking portion may also include a polysiloxane chain. However, the organopolysiloxane elastomer of the present invention preferably has a highly crosslinked molecular structure in which the polysiloxane chains are crosslinked in the three-dimensional network structure at relatively high density. Thus, the organopolysiloxane preferably is an insoluble gel, gum, or powdery solid in a solvent or the like.

The organopolysiloxane elastomer of the present invention preferably is capable of swelling by incorporating an amount of an oil agent that is at least the weight (mass) of the organopolysiloxane elastomer itself. The organopolysiloxane elastomer of the present invention including the oil agent can exist in the form of a paste. Although examples of the types of oil agent and the like are explained below, silicone oil is preferred.

It is preferred that the organopolysiloxane elastomer of the present invention possesses a hydrophilic group (especially a glycerin derivative group) represented by Q that is bonded to a different silicon atom from the silicon atom bonded to the group having a siloxane dendron structure represented by $L^1$. Q constitutes the hydrophilic region of the organopolysiloxane elastomer of the present invention. The structure of Q is not specifically limited as long as it has a hydrophilic region, especially a glycerin derivative region, but it is preferred that a glycerin derivative residue is bonded to a silicon atom via a divalent or higher organic group, preferably a divalent organic group.

The glycerin derivative residue is a hydrophilic group having a (poly)glycerin structure, which are hydrophilic groups having a monoglycerin, diglycerin, triglycerin, tetraglycerin, and pentamer or greater polyglycerin structure. Additionally, the terminal hydroxyl group may be partially capped with an alkyl group. Furthermore, the (poly)glycerin structure may be straight or branched, and may be a structure that is branched in a dendritic manner, as well.

It is preferred that Q is a hydrophilic group bonded to a silicon atom via a linking group that is at least divalent, and having at least one hydrophilic unit selected from hydrophilic units represented by the following structural formulae (3-1) to (3-4):

$$—C_rH_{2r}—O— \quad (3\text{-}1)$$

(in the formula, r is a number in a range of 1 to 6);

[Formula 25]

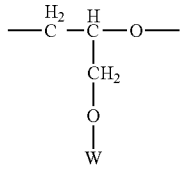

(3-2)

(in the formula, W represents a hydrogen atom or an alkyl group having from 1 to 20 carbons);

[Formula 26]

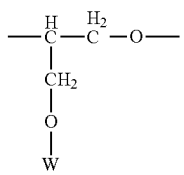

(3-3)

(in the formula, W is synonymous with the groups described above); and

[Formula 27]

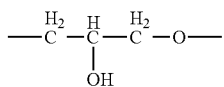

(3-4)

In the structural formulae (3-2) to (3-4) above, W preferably is a hydrogen atom. Particularly, W being a hydrogen atom has the advantage of being highly environmentally compatible since oxidation in air does not occur easily, and aldehydes such as formaldehyde and the like, and antigenic compounds such as formic acid esters and the like, are not easily produced over time during storage.

The hydrophilic units represented by structural formulae (3-2) to (3-4) are hydrophilic units that are included in hydrophilic groups derived from hydrophilic compounds selected principally from polyhydric alcohols containing glycerin, polyglycerins (also called "polyglycerols"), and polyglycidyl ethers or compounds in which terminal hydroxyl groups thereof are partially capped by hydrocarbon groups. Furthermore, when realizing formulations for cosmetics and external use preparations that are completely PEG-free formulations (i.e., formulations that do not include compounds having a polyoxyethylene (PEG) structure), it is preferred that the organopolysiloxane elastomer of the present invention does not include a group in which two or more of the hydrophilic units represented by the structural formula (3-1) are linked in a molecule.

The glycerin derivative group represented by the structural formulae (3-2) to (3-4) may be a hydrophilic group that does not have a branched structure, such as a monoglycerin-modified group or diglycerin-modified group, but it may also be a hydrophilic group having a branched structure in a portion of the functional group, such as a polyglycerol group or polyglycidyl ether group.

In further detail, Q may be a hydrophilic segment that is bonded to a silicon atom via a linking group that is at least divalent, and in which a plurality of at least one of hydrophilic units selected from the hydrophilic units represented by structural formulae (3-1) to (3-4) are linearly linked. Similarly, the glycerin derivative group may also be a hydrophilic segment that is bonded to a silicon atom via a linking group that is at least divalent, and in which a plurality of at least one of the hydrophilic units selected from the hydrophilic units represented by structural formulae (3-1) to (3-4) are bonded in a branching fashion via branching units selected from the groups represented by the following structural formulae (3-5) to (3-7).

[Formula 28]

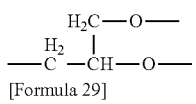

(3-5)

[Formula 29]

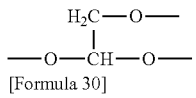

(3-6)

[Formula 30]

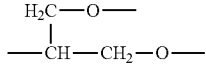

(3-7)

In structural formulae (3-5) to (3-7), the at least one hydrophilic unit selected from the hydrophilic units represented by the general formulae (3-1) to (3-4) are each independently bonded to the two oxygen atoms. The hydrophilic unit may further be bonded to a branch unit selected from groups represented by structural formulae (3-5) to (3-7). Moreover, the hydrophilic unit may be formed so as to have a dendroid-shape polyether structure, a polyglycerol structure, or a polyglycidyl ether structure obtained by branching into multiple generations. As an example, a structure is shown below of a glycerin derivative group in which one of the branching units represented by structural formula (3-5) and two of the branching units represented by structural formula (3-7) are dendritically branched, but of course the dendritic polyglycerol structure is not limited to this.

[Formula 31]

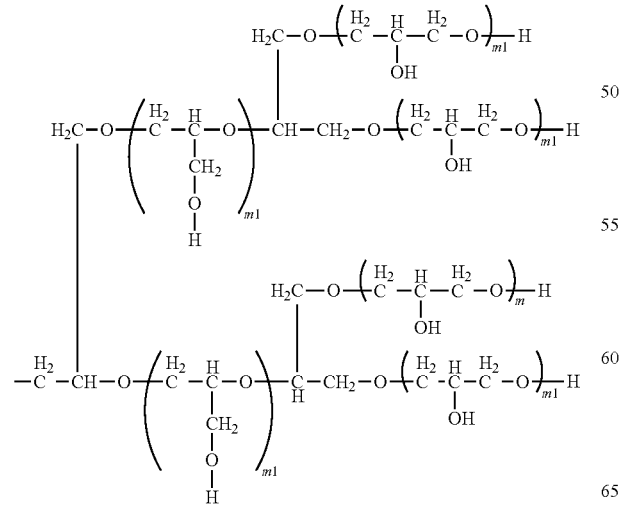

In the formula, m1 is a number in a range of 0 to 50, provided that not all of the m1 moieties are 0.

Linking groups that are at least divalent are silicon atom-bonding regions in a glycerin derivative group, and the structure thereof is not particularly limited, but examples thereof include alkylene groups such as ethylene groups, propylene groups, butylene groups, and hexylene groups; alkylene phenylene groups such as ethylene phenylene groups and propylene phenylene groups; alkylene aralkylene groups such as ethylene benzylene groups; alkyleneoxyphenylene groups such as ethyleneoxyphenylene groups and propyleneoxyphenylene groups; and alkyleneoxybenzylene groups such as methyleneoxybenzylene groups, ethyleneoxybenzylene groups, and propyleneoxybenzylene groups; as well as the groups shown below. Furthermore, it is preferred that there are from 0 to 3, and more preferably 0 or 1, ether bonds in the linking group that is at least divalent.

[Formula 32]

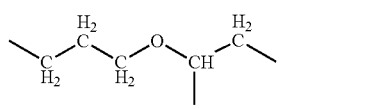
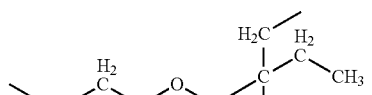
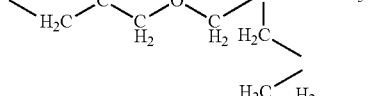
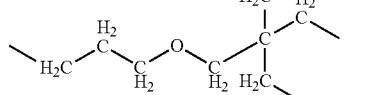
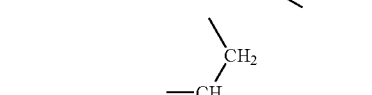
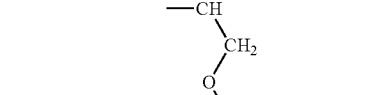
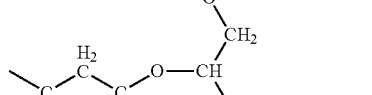
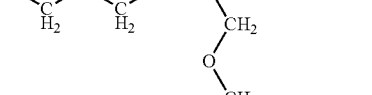
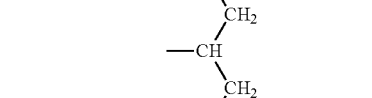
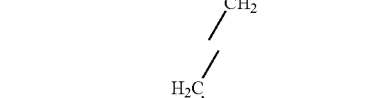
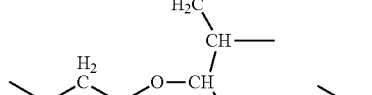
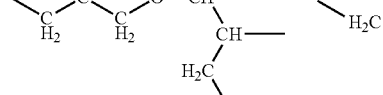
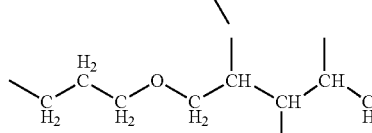

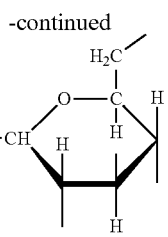

Q is preferably a hydrophilic group represented by the following structural formula (4-1) to (4-4).

General Formula (4-1):

$$—R^3(—O—X^1{}_m—R^4)_p \qquad (4\text{-}1)$$

In the formula,
$R^3$ is an organic group having (p+1) valency,
p is a number in a range of 1 to 3,
$X^1$ are each independently at least one hydrophilic unit selected from the hydrophilic units represented by the general formulae (3-1) to (3-4) above,
m is a number in a range of 1 to 100,
$R^4$ is a hydrogen atom or a group selected from the group consisting of alkyl groups, acyl groups, and glycidyl groups having from 1 to 20 carbons.

General Formula (4-2):

$$—R^3(—O—X^2)_p \qquad (4\text{-}2)$$

In the formula,
$R^3$ is synonymous with the groups described above,
p is the same number as described above, and
$X^2$ is a hydrophilic group represented by the following structural formula (4-2-1):

[Formula 33]

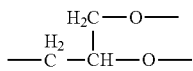
$$(4\text{-}2\text{-}1)$$

in the formula, at least one hydrophilic unit selected from the hydrophilic units represented by the general formulae (3-1) to (3-4) is independently bonded to each of the two oxygen atoms.

General Formula (4-3):

$$—R^3(—O—X^3)_p \qquad (4\text{-}3)$$

In the formula,
$R^3$ is synonymous with the groups described above,
p is the same number as described above, and
$X^3$ is a hydrophilic group represented by the following structural formula (4-3-1):

[Formula 34]

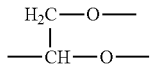
$$(4\text{-}3\text{-}1)$$

in the formula, at least one hydrophilic unit selected from the hydrophilic units represented by the general formulae (3-1) to (3-4) is independently bonded to each of the two oxygen atoms.

General Formula (4-4):

$$—R^3(—O—X^4)_p \qquad (4\text{-}4)$$

In the formula,
$R^3$ is synonymous with the groups described above,
p is the same number as described above, and
$X^4$ is a hydrophilic group represented by the following structural formula (4-4-1):

[Formula 35]

$$(4\text{-}4\text{-}1)$$

in the formula, at least one hydrophilic unit selected from the hydrophilic units represented by the general formulae (3-1) to (3-4) is independently bonded to each of the two oxygen atoms.

The same group as the linking group that is at least divalent described above can be given as an example of $R^3$.

In particular, p1 is preferably equal to 1, and a group selected from divalent organic groups represented by the following general formulae are given as preferable examples of $R^3$.

[Formula 36]

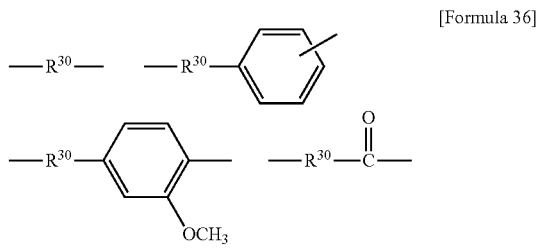

In the formula, $R^{30}$ may have a substituent, and are each independently a straight or branched alkylene group or alkenylene group having from 2 to 22 carbons, or an arylene group having from 6 to 22 carbons.

More preferably, Q is a hydrophilic group represented by the following structural formulae (6-1) to (6-4), and these generally are glycerin derivative groups derived from polyglycerin-based compounds.

[Formula 37]

$$(6\text{-}1)$$

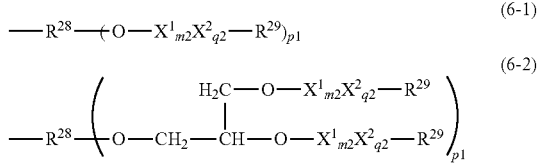
$$(6\text{-}2)$$

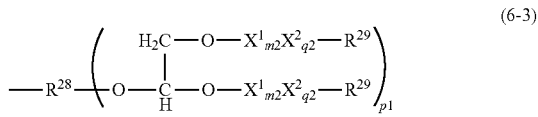
$$(6\text{-}3)$$

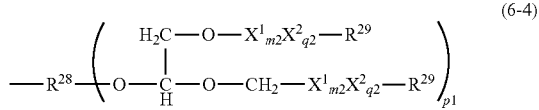

(6-4)

In formulae (6-1) to (6-4), $R^{28}$ is an organic group having (p1+1) valency, where p1 is a number that is greater than or equal to 1 and less than or equal to 3. The same groups as the linking group that is at least divalent can be given as examples of $R^{28}$.

More preferably, p1 is equal to 1, and a group selected from the divalent organic groups represented by the above general formulae can be given as preferable examples of $R^{28}$.

$X^1$ are each independently at least one hydrophilic unit selected from the hydrophilic units represented by the following general formulae (4-1-1) to (4-3-1), and m2 is a number in a range of 1 to 5, and is more preferably a number in a range of 1 to 4.

[Formula 38]

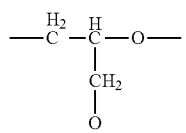

(4-1-1)

[Formula 39]

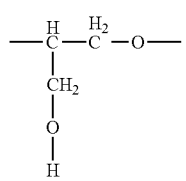

(4-2-1)

[Formula 40]

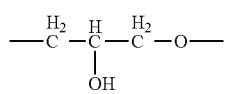

(4-3-1)

$X^2$ is any oxyalkylene unit, which may include a glycerin derivative group, and q2 is a number in a range of 0 to 50. It is preferred that q2 is a number in a range of 0 to 30, and preferably is 0. Furthermore, $X^2$ preferably is an oxyethylene unit or oxypropylene unit. Additionally, in cases where $X^2$ is continuously bonded, one or more can also be included in the glycerin derivative group as a polyoxyalkylene unit represented by $-(C_2H_4O)_{t1}(C_3H_6O)_{t2}-$ (in the formula, t1 and t2 are each a number greater than or equal to 0, where (t1+t2) is a number in a range of 0 to 50, preferably a number in a range of 0 to 30). Provided that, when realizing the formulation of a cosmetic or external use preparation as an entirely PEG-free formulation, it is preferred that the molecule does not include an oxyalkylene structure having an average number of repetitions of an oxyalkylene unit of 2 or higher.

The bonding format of $X^1$ and $X^2$ can be block or random. That is, the glycerin derivative group may be a hydrophilic group in which hydrophilic segments, which are obtained by bonding hydrophilic units represented by general formulae (4-1-1) to (4-3-1) above in a block manner, are bonded to hydrophilic segments comprising polyoxyalkylene units, and may be a hydrophilic group in which these constituent units are bonded in a random manner. An example thereof is a bonding pattern such as $-(X^2)_{m1}-X^1-(X^2)_{m2}-X^1-$.

$R^{29}$ is a hydrogen atom or a group selected from the group consisting of alkyl groups, acyl groups, and glycidyl groups having from 1 to 20 carbons.

From the aspects of the affinity with oil agents and emulsification properties of the organopolysiloxane elastomer of the present invention, the glycerin derivative group is particularly preferably a hydrophilic group that is derived from a (poly)glycerin represented by the following structural formula (6-1-1).

[Formula 41]

(6-1-1)

In the formula, $R^{28'}$ is a divalent organic group and can, e.g., be the same group as those described above,
$X^1$ and $R^{29}$ are the same groups as those described above, and m2 is a number in a range of 1 to 5.

From the perspectives of affinity with oil agents and emulsification properties, and use as various treatment agents (surfactants and surface treatment agents), particularly use as powder treatment agents and use as cosmetic raw material, the glycerin derivative group in the organopolysiloxane elastomer of the present invention is a hydrophilic group derived from a (poly)glycerin-based compound. Most preferably, the glycerin derivative group in the organopolysiloxane elastomer of the present invention is a hydrophilic group derived from a (poly)glycerin. Specifically, the hydrophilic group preferably is a (poly)glycerin monoallyl ether or a (poly)glyceryl eugenol, which are examples of hydrophilic groups derived from a glycerin-based compound having a monoglycerin, a diglycerin, a triglycerin, or a tetraglycerin structure.

From the viewpoints of affinity with oil agents and emulsification properties that can realize PEG-free formulations, it is particularly preferred that the glycerin derivative group in the organopolysiloxane elastomer of the present invention is a diglycerin derivative group.

In the glycerin derivative group, the average number of repetitions of the hydrophilic unit represented by the structural formulae (4-1-1) to (4-3-1) above is in a range of 1.1 to 2.9, and preferably this average number of repetitions is in a range of 1.5 to 2.4, more preferably in a range of 1.8 to 2.2, and most preferably the average number is 2. Having the average number of repetitions of the hydrophilic unit in the ranges described above has the advantage of making it possible to obtain emulsion compositions that are stable over long periods of time.

The number of repetitions of the glycerin unit may be an average value. A content of the diglycerin derivative group in which the number of repetitions of the glycerin unit is 2 is preferably more than 30 mass %, more preferably 50 mass % or more, and even more preferably 80 mass % or more, with respect to all of the other glycerin derivative groups. Most preferable is a pure form in which purity of the diglycerin derivative group is greater than 98% by mass. Additionally, where the goal is a PEG-free formulation, it is necessary that the functional group does not include an oxyalkylene structure having an average number of repetitions of an oxyalkylene unit of 2 or higher.

It is more preferable that the glycerin derivative group is a glycerin derivative group represented by the following structural formula (9):

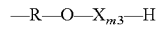 (9)

In the formula, R is a divalent organic group, examples of which are the same groups as the divalent linking groups described above. R is preferably a divalent linking group that does not include an oxyalkylene structure having an average number of repetitions of an oxyalkylene unit of 2 or higher. X is at least one glycerin unit selected from the hydrophilic units represented by the structural formulae (4-1-1) to (4-3-1) above. m3 represents the number of repetitions of the glycerin unit, and is on average, a number in a range of 1.5 to 2.4. Furthermore, the preferred range of the number of repetitions of each glycerin unit is the same as that described above.

Most preferably, the glycerin derivative group is a diglycerin derivative group represented by the following general formula (9-1):

[Formula 42]

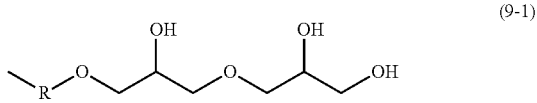
(9-1)

(in the formula, R represents a divalent organic group), or by the following general formula (9-2):

[Formula 43]

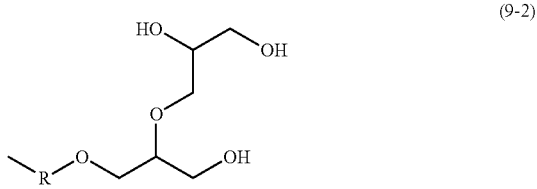
(9-2)

(in the formula R is the same as that described above).

In the organopolysiloxane elastomer of the present invention, the diglycerin derivative group-containing organic group is preferably a hydrophilic group derived from diglycerin monoallyl ether, diglyceryl eugenol, or the like.

The organopolysiloxane elastomer of the present invention can be produced by causing reactions between at least the following:
(A) an organohydrogenpolysiloxane,
(B) a siloxane dendron having one reactive unsaturated group in a molecule, and
(C) at least one type of organic compound selected from the group consisting of: (C1) organic compounds having an average of greater than one reactive unsaturated group in a molecule, and (C2) organic compounds having at least one reactive unsaturated group and at least one epoxy group in a molecule.

In particular, the organopolysiloxane elastomer of the present invention that comprises a hydrophilic group, preferably a glycerin derivative group, can be produced by causing reactions between at least the following:
(A) an organohydrogenpolysiloxane,
(B) a siloxane dendron having one reactive unsaturated group in a molecule,
(C) at least one organic compound selected from the group consisting of (C1) organic compounds having an average of more than one reactive unsaturated groups in a molecule, and (C2) organic compounds having at least one reactive unsaturated group and at least one epoxy group in a molecule (provided that (C) is optional in cases where the below described (D) has an average of more than one reactive unsaturated group in a molecule); and
(D) a hydrophilic derivative having a reactive unsaturated group and a hydrophilic group that includes at least one hydrophilic unit selected from the hydrophilic units represented by the structural formulae (3-1) to (3-4).

No particular limitation is placed on the (A) organohydrogenpolysiloxane as long as the organohydrogenpolysiloxane has silicon atoms hydrogen atoms. This organohydrogenpolysiloxane has an average of more than one such silicon-bonded hydrogen atom, preferably has on average of 1.01 to 100 silicon-bonded hydrogen atoms, more preferably has on average of 1.1 to 50 silicon-bonded hydrogen atoms, further preferably has on average of 1.2 to 25 silicon-bonded hydrogen atoms, and particularly preferably has on average of 1.3 to 10 silicon-bonded hydrogen atoms in a molecule. The utilized organopolysiloxane part of the organohydrogenpolysiloxane may be straight, branched, or net-like. The positions of the silicon-bonded hydrogen atoms in the organohydrogenpolysiloxane is not limited, and can be on the main chain or at the terminals. One type of organohydrogenpolysiloxane or a combination of 2 or more types organohydrogenpolysiloxane may be used as the component (A).

Examples of the component (A) include, e.g., 1,1,3,3-tetramethyl disiloxane, 1,3,5,7-tetramethylcyclotetrasiloxane, methylhydrogenpolysiloxane capped at both molecular terminals with trimethylsiloxy groups, dimethylsiloxane-methylhydrogensiloxane copolymer capped at both molecular terminals with trimethylsiloxy groups, dimethylsiloxane capped at both molecular terminals with dimethylhydrogensiloxy groups, dimethylpolysiloxane capped at both molecular terminals with dimethylhydrogensiloxy groups, dimethylsiloxane-methylhydrogensiloxane copolymer capped at both molecular terminals with dimethylhydrogensiloxy groups, methylhydrogensiloxane-diphenylsiloxane copolymer capped at both molecular terminals with trimethylsiloxy groups, methylhydrogensiloxane-diphenylsiloxane-dimethylsiloxane copolymer capped at both molecular terminals with trimethylsiloxy groups, copolymers formed from $(CH_3)_2HSiO_{1/2}$ units and $SiO_{4/2}$ units, and copolymers formed from $(CH_3)_2HSiO_{1/2}$ units, $SiO_{4/2}$ units, and $(C_6H_5)SiO_{3/2}$ units.

The component (A) is preferably a component represented by the average composition formula (1):

$$R^5{}_aH_bSiO_{(4-a-b)/2} \quad (1)$$

in the formula,
$R^5$ each independently represent monovalent organic groups, wherein $1.0 \le a \le 3.0$ and $0.001 \le b \le 1.5$.

The molecular structure of the (A) organohydrogenpolysiloxane molecule is not limited, and examples of this molecular structure include straight, straight with some branched regions, branched, cyclic, and dendritic structures, of which straight structures are preferable. Furthermore, the molecular weight thereof is not particularly limited, molecules may be used ranging from low molecular weight to high molecular weight. Specifically, the number-average molecular weight is preferably in a range of 100 to 1,000,000, and further preferably is in a range of 300 to 500,000.

This type of organohydrogenpolysiloxane is exemplified by organohydrogenpolysiloxanes represented by the following structural formulae:

(i)

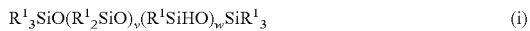
(ii)

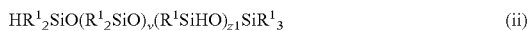
(iii)

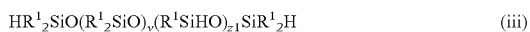

(in the formula, $R^1$ has the same meaning as above, v is 0 or a positive integer, w is a positive integer, and z1 is 0 or a positive integer). These organohydrogenpolysiloxanes are straight organohydrogenpolysiloxanes that have silicon-bonded hydrogen atoms (i) only on side chains, (ii) on side chains or one terminal of the molecular chain, or (iii) on side chains and at both terminals of the molecular chain.

The monovalent organic group is not particularly limited, but preferably is selected from the following (E1) to (E9):
(E1) a substituted or unsubstituted, straight or branched monovalent hydrocarbon group having from 1 to 60 carbons;
(E2) a polyoxyalkylene group represented by —$R^{13}O(AO)_zR^{14}$ (in the formula, AO is an oxyalkylene group having from 2 to 4 carbons, $R^{13}$ is a substituted or unsubstituted, straight or branched divalent hydrocarbon group having from 3 to 5 carbons, $R^{14}$ is a hydrogen atom, a substituted or unsubstituted, straight or branched monovalent hydrocarbon group having from 1 to 24 carbons, or a substituted or unsubstituted, straight or branched acyl group having from 2 to 24 carbons, and z=1 to 100);
(E3) a substituted or unsubstituted, straight or branched alkoxy group having from 1 to 30 carbons;
(E4) a hydroxyl group;
(E5) an ester group represented by —$R^{15}$—$COOR^{16}$ (in the formula, $R^{15}$ represents a substituted or unsubstituted, straight or branched divalent hydrocarbon group having from 2 to 20 carbons, and $R^{16}$ represents a substituted or unsubstituted, straight or branched monovalent hydrocarbon group having from 1 to 30 carbons);
(E6) an ester group represented by —$R^{17}$—$OCOR^{18}$ (in the formula, $R^{17}$ represents a substituted or unsubstituted, straight or branched divalent hydrocarbon group having from 2 to 20 carbons, and $R^{18}$ represents a substituted or unsubstituted, straight or branched monovalent hydrocarbon group having from 1 to 30 carbons);
(E7) an alkyl group substituted with a polysiloxane chain structure and represented by the following general formula (6):

[Formula 44]

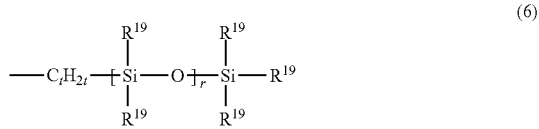

(6)

(in the formula, $R^{19}$ each represents an independent substituted or unsubstituted, straight or branched monovalent hydrocarbon group having from 1 to 30 carbons, hydroxyl group, or hydrogen atom, wherein at least one of the $R^{19}$ groups is the monovalent hydrocarbon group, t is a number in a range of 2 to 10, and r is a number in a range of 1 to 100;
(E8) an epoxy group represented by the following general formula (7):

[Formula 45]

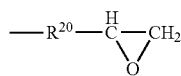

(7)

(in the formula, $R^{20}$ represents a substituted or unsubstituted, straight or branched divalent hydrocarbon group having from 2 to 20 carbons); and (E9) an alicyclic epoxy group represented by the following general formula (8):

[Formula 46]

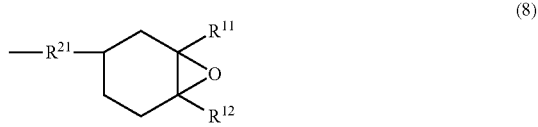

(8)

(in the formula, $R^{21}$ represents a substituted or unsubstituted, straight or branched divalent hydrocarbon group having from 2 to 20 carbons; and $R^{11}$ and $R^{12}$ are synonymous with those described above).

From the viewpoints of affinity with oil agents and emulsification properties that can realize PEG-free formulations, the molecule of the organopolysiloxane elastomer of the present invention preferably further contains at least one monovalent organic group selected from
(E1-1) a substituted or unsubstituted, straight or branched monovalent hydrocarbon group having from 9 to 60 carbons and
(E8) an alkyl group substituted with a polysiloxane chain structure represented by general formula (6) above,
which are introduced to the organopolysiloxane elastomer molecule of the present invention by reacting the corresponding component (C) with the component (A). Due to the high hydrophobicity and excellent affinity with oil agents of these functional groups, using them together with the glycerin derivative groups has the advantage of further improving the emulsification properties (applicability to a wide range of oil agents) of the organopolysiloxane elastomer of the present invention. It is possible and preferable to introduce two or more types of these functional groups in a molecule.

Examples of the substituted or unsubstituted, straight or branched monovalent hydrocarbon group of (E1), (E2), (E5), (E6), and (E7) include methyl groups, ethyl groups, propyl groups, butyl groups, pentyl groups, hexyl groups, heptyl groups, octyl groups, and similar alkyl groups; cyclopentyl groups, cyclohexyl groups, and similar cycloalkyl groups; vinyl groups, allyl groups, butenyl groups, and similar alkenyl groups; phenyl groups, tolyl groups, and similar aryl groups; benzyl groups and similar aralkyl groups; and groups wherein the hydrogen atoms bonded to the carbon atoms of these groups are substituted at least partially by fluorine or a similar halogen atom, or an organic group containing an epoxy group, a glycidyl group, an acyl group, a carboxyl group, an amino group, a methacryl group, a mercapto group, or the like. The monovalent hydrocarbon group preferably is a group other than an alkenyl group, and is more preferably a methyl group, ethyl group, or phenyl group.

The substituted or unsubstituted, straight or branched divalent hydrocarbon groups in (E2), (E5), (E6), (E8), and (E9) are as described above.

Examples of the substituted or unsubstituted, straight or branched alkoxy group in (E3) include lower alkoxy groups such as methoxy groups, ethoxy groups, isopropoxy groups, and butoxy groups; and higher alkoxy groups such as lauryl alkoxy groups, myristyl alkoxy groups, palmityl alkoxy groups, oleyl alkoxy groups, stearyl alkoxy groups, and behenyl alkoxy groups.

The component (B) is not particularly limited as long as the component (B) has at least one unsaturated bond and a siloxane dendron structure, but compounds are preferred that are represented by the following general formula (2') and have a siloxane dendron structure with one carbon-carbon double bond at the molecular terminal.

General Formula (2'):

[Formula 47]

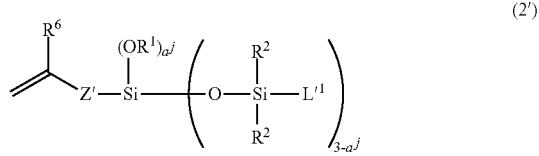

In the formula,
L$^{l1}$ is an alkyl group or phenyl group having from 1 to 6 carbons, or when j=1, L$^{l1}$ is a silylalkyl group represented by the following general formula (2"):

[Formula 48]

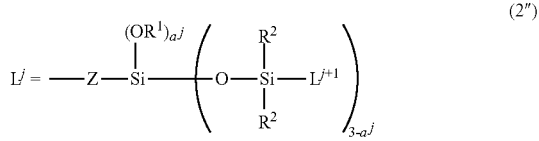

(in the formula,
R$^2$ is an alkyl group or phenyl group having from 1 to 6 carbons,
Z is a divalent organic group,
j represents the number of generations of the silylalkyl group that is represented by L$^j$, when the number of generations (the number of repetitions) of the silylalkyl group is k', j is an integer of 1 to k', and the number of generations k' is an integer from 1 to 10; L$^{j+1}$ is the silylalkyl group when j is less than k', and is the R$^2$ moiety when j=k'; and
a$^j$ is a number in a range of 0 to 3),
Z' is a divalent organic group, and
R$^6$ is a hydrogen atom or a methyl group.

Specific examples of R$^2$ and Z are as described above, and specific examples of the divalent organic groups of Z' are the same as the divalent organic groups for Z.

There are no particular restrictions regarding the structure of the component (C) as long as the component has more than one, preferably from 1.01 to 10, more preferably from 1.2 to 8, even more preferably from 1.5 to 6, and particularly preferably from 2.0 to 4.5 unsaturated bonds and preferably carbon-carbon double bonds on average in a molecule, and straight-chain, branched, or net-like organic compounds may be used. This organic compound preferably is an organopolysiloxane or unsaturated aliphatic hydrocarbon. The position of the unsaturated bond in the organic compound, preferably organopolysiloxane or unsaturated aliphatic hydrocarbon, also is not limited, and the unsaturated bond may be positioned on the main chain or at a terminal. However, from the aspect of the ease of controlling crosslinking density, it is preferable to use a compound of high purity having two unsaturated groups in a molecule, positioned, e.g., at both terminals.

It is preferred that the reactive unsaturated group is present in an unsaturated aliphatic hydrocarbon group. The unsaturated aliphatic hydrocarbon group preferably has from 2 to 30 carbons, and further preferably has from 2 to 20 carbons. Examples of the monovalent unsaturated aliphatic hydrocarbon group having from 2 to 30 carbons include straight or branched alkenyl groups such as vinyl groups, 1-propenyl groups, allyl groups, isopropenyl groups, 1-butenyl groups, 2-butenyl groups, pentenyl groups, hexenyl groups, and the like; cycloalkenyl groups such as cyclopentenyl groups, cyclohexenyl groups, and the like; cycloalkenylalkyl groups such as cyclopentenylethyl groups, cyclohexenylethyl groups, cyclohexenylpropyl groups, and the like; and alkynyl groups such as ethynyl groups, propargyl groups, and the like. Alkenyl groups are preferred, and vinyl groups and hexenyl groups are especially preferred.

When the component (C1) is an organopolysiloxane, the reactive unsaturated group-containing unsaturated aliphatic hydrocarbon group preferably is bonded to a silicon atom. In addition, when the component (C1) is an organopolysiloxane, group bonding to silicon atoms other than the unsaturated aliphatic hydrocarbon may be substituted or unsubstituted monovalent hydrocarbon groups or monovalent organic groups having a reactive functional group.

Substituted or unsubstituted monovalent hydrocarbon groups typically are substituted or unsubstituted, straight or branched monovalent saturated hydrocarbon groups having from 1 to 30 carbons, preferably from 1 to 10 carbons, and more preferably from 1 to 4 carbons, and monovalent aromatic hydrocarbon groups having from 6 to 30 carbons, and more preferably from 6 to 12 carbons. Moreover, the component (C1) may include, as a monovalent organic group, an alkoxy group having from 1 to 12 carbons, such as a methoxy group, ethoxy group, propoxy group, or butoxy group.

Examples of the monovalent saturated hydrocarbon group having from 1 to 30 carbons include straight or branched alkyl groups such as methyl groups, ethyl groups, n-propyl groups, isopropyl groups, n-butyl groups, isobutyl groups, sec-butyl groups, tert-butyl groups, pentyl groups, hexyl groups, heptyl groups, octyl groups, nonyl groups, decyl groups; and cycloalkyl groups such as cyclopentyl groups, cyclohexyl groups, cycloheptyl groups, and cyclooctyl groups.

Examples of the monovalent aromatic hydrocarbon group having from 6 to 30 carbons include aryl groups such as phenyl groups, tolyl groups, xylyl groups, and mesityl groups. Of these, phenyl groups are preferable. Furthermore, in the present specification, "aromatic hydrocarbon groups" include groups formed only from an aromatic hydrocarbon, as well as groups in which an aromatic hydrocarbon and a saturated aliphatic hydrocarbon are conjugated. Examples of groups in which an aromatic hydrocarbon and a saturated hydrocarbon are conjugated include aralkyl groups such as benzyl groups and phenethyl groups.

Hydrogen atoms in the monovalent hydrocarbon groups described above may be substituted by one or more substituted groups, and the substituted groups may be selected from the group consisting of, for example, a halogen atom (a fluorine atom, a chlorine atom, a bromine atom, or an iodine atom), a hydroxyl group, an amide group, an ester group, a carboxyl group and an isocyanate group. A monovalent saturated or aromatic hydrocarbon group having at least one of the substituted groups is preferred. Specifically, examples include 3,3,3-trifluoropropyl groups, 3-chloropropyl groups, 3-hydroxypropyl groups, 3-(2-hydroxyethoxy)propyl groups, 3-carboxypropyl groups, 10-carboxydecyl groups, and 3-isocyanatopropyl groups.

Examples of monovalent organic groups having reactive functional groups include monovalent saturated or aromatic hydrocarbon groups having reactive functional groups selected from the group consisting of, e.g., hydroxyl groups, mercapto groups, epoxy groups, amino groups, amide groups, ester groups, carboxyl groups and isocyanate groups.

One or a plurality of reactive functional groups may exist in the monovalent organic group. $R^1$ preferably is a monosaturated or aromatic hydrocarbon group having at least one of the reactive functional groups described above. Specific examples of the reactive functional group include 3-hydroxypropyl groups, 3-(2-hydroxyethoxy)propyl groups, 3-mercaptopropyl groups, 2,3-epoxypropyl groups, 3,4-epoxybutyl groups, 4,5-epoxypentyl groups, 2-glycidoxyethyl groups, 3-glycidoxypropyl groups, 4-glycidoxybutyl groups, 2-(3,4-epoxycyclohexyl)ethyl groups, 3-(3,4-epoxycyclohexyl)propyl groups, aminopropyl groups, N-methylaminopropyl groups, N-butylaminopropyl groups, N,N-dibutylaminopropyl groups, 3-(2-aminoethoxy)propyl groups, 3-(2-aminoethylamino)propyl groups, 3-carboxypropyl groups, 10-carboxydecyl groups, and 3-isocyanate propyl groups.

The component (C1) preferably is a straight or branched polysiloxane. The straight component (C1) preferably is a polymer including diorganosiloxane units and triorganosiloxy units, examples of which include dimethylpolysiloxanes capped at both molecular terminals with dimethylvinylsiloxy groups, dimethylsiloxane-methylphenylsiloxane copolymers capped at both molecular terminals with dimethylvinylsiloxy groups, dimethylsiloxane-methylvinylsiloxane copolymers capped at both molecular terminals with dimethylvinylsiloxy groups, dimethylsiloxane-methylvinylsiloxane copolymers capped at both molecular terminals with trimethylsiloxy groups, dimethylsiloxane-methylvinylsiloxane-methylphenylsiloxane copolymers capped at both molecular terminals with trimethylsiloxy groups, dimethylsiloxane-methylvinylsiloxane copolymers capped at both molecular terminals with silanol groups, such polymers where part of the methyl groups are substituted by non-methyl groups such as ethyl groups and propyl groups, such polymers substituted with halogenated alkyl groups such as 3,3,3-trifluoropropyl groups, and mixtures of two or more such polymers. In particular, straight diorganopolysiloxanes are preferred that have an unsaturated aliphatic hydrocarbon groups only at both molecular terminals, and straight diorganopolysiloxanes having an alkenyl group are especially preferred.

Polymers that include a diorganosiloxane unit, an organosilsesquioxane unit, and a triorganosiloxy unit are particularly preferred as the branched component (C1). Silicon-bonded organic groups in these units preferably are monovalent hydrocarbon groups including alkyl groups such as methyl groups, ethyl groups and propyl groups; alkenyl groups such as vinyl groups, allyl groups, butenyl groups and hexenyl groups; aryl groups such as phenyl groups and tolyl groups; and halogenated alkyl groups such as 3,3,3-trifluoropropyl groups, and the like, and may contain extremely small quantities of hydroxyl groups, as well as alkoxy groups such as methoxy groups, but at least two silicon-bonded organic groups in this polymer must be unsaturated aliphatic hydrocarbon groups, and especially alkenyl groups. In addition, the proportions of these units are not limited, but in this polymer, it is preferable for the quantity of diorganosiloxane units be in a range of 80.00 to 99.65 mol % and the quantity of organosilsesquioxane units to be in a range of 0.10 to 10.00 mol %, with the remaining mol % comprising triorganosiloxy units.

Examples of the component (C1) include, e.g., the (C1-5) unsaturated group-containing silicone compound represented by the average composition formula (5-5):

$$R^7{}_c R^8{}_d SiO_{(4-c-d)/2} \quad (5\text{-}5)$$

(in the formula,
$R^7$ may be each independently monovalent organic group that differs from $R^8$;

$R^8$ are each independently monovalent unsaturated aliphatic hydrocarbon groups having from 2 to 30 carbons, $1.0 \le c \le 2.5$, and $0.001 \le d \le 1.5$). Examples of the monovalent unsaturated aliphatic hydrocarbon group having from 2 to 30 carbons are as listed above.

In the average composition formula (5-5), the monovalent organic group that is $R^7$ is not particularly limited, but the monovalent organic group is preferably selected from the following (F1) to (F6):
(F1) a substituted or unsubstituted, straight or branched monovalent hydrocarbon group having from 1 to 60 carbons (excluding monovalent hydrocarbon groups having from 2 to 20 carbons and an aliphatic unsaturated group);
(F2) a hydroxyl group;
(F3) an ester group represented by —$R^{15}$—$COOR^{16}$ (in the formula, $R^{15}$ and $R^{16}$ are as described above);
(F4) an ester group represented by —$R^{17}$—$OCOR^{18}$ (in the formula, $R^{17}$ and $R^{18}$ are as described above);
(F5) an amide group represented by —$R^{24}$—$NR^{25}COR^{26}$ (in the formula, $R^{24}$ represents a substituted or unsubstituted, straight or branched divalent hydrocarbon group having from 2 to 20 carbons, $R^{25}$ represents a hydrogen atom or a substituted or unsubstituted, straight or branched monovalent hydrocarbon group having from 1 to 20 carbons, and $R^{26}$ represents a substituted or unsubstituted, straight or branched monovalent hydrocarbon group having from 1 to 30 carbons); and
(F6) an amide group represented by —$R^{24}$—$CONR^{25}R^{27}$ (in the formula, $R^{24}$ is a substituted or unsubstituted, straight or branched divalent hydrocarbon group having from 2 to 20 carbons, and $R^{25}$ and $R^{27}$ are each independently a hydrogen atom or a substituted or unsubstituted, straight or branched monovalent hydrocarbon group having from 1 to 20 carbons). The definitions, types, and the like of the substituted or unsubstituted, straight or branched monovalent hydrocarbon groups and divalent hydrocarbon groups are as previously described.

On the other hand, the component (C1) may be an unsaturated aliphatic hydrocarbon. Examples of unsaturated aliphatic hydrocarbons include various dienes, diynes, enynes and the like having two or more unsaturated bonds. On the aspect of crosslinking, dienes, diynes, and enynes are preferable. Dienes, diynes, and enynes are compounds that have a structure in which at least two unsaturated bonds are separated by one or more, preferably two or more, single bonds in a molecule. The unsaturated aliphatic hydrocarbon group may be present at the terminal of the molecular chain, or as a pendant group along the molecular chain.

Examples of unsaturated aliphatic hydrocarbons as the component (C1) include α,ω-unsaturated alkenes or alkynes having from 2 to 30 carbons. Examples of the component (C1) include (C1-1) α,ω-dienes represented by the general formula (5-1):

$$CH_2\!=\!CH(CH_2)_xCH\!=\!CH_2 \quad (5\text{-}1)$$

(in the formula, $1 \le x \le 20$); (C1-2) α,ω-diynes represented by the general formula (5-2):

$$CH\!\equiv\!C(CH_2)_xC\!\equiv\!CH \quad (5\text{-}2)$$

(in the formula, $1 \le x \le 20$); (C1-3) α,ω-ene-ynes represented by the general formula (5-3):

$$CH_2\!=\!CH(CH_2)_xC\!\equiv\!CH \quad (5\text{-}3)$$

(in the formula $1 \le x \le 20$); and (C1-4) bisalkenyl polyether compounds represented by the general formula (5-4):

$$C_qH_{2q-1}O(C_nH_{2n}O)_yC_qH_{2q-1} \quad (5\text{-}4)$$

(in the formula, $2 \le q \le 20$, $2 \le n \le 4$, y is the total number of repetitions of oxyethylene units, oxypropylene units, and oxybutylene units, and $1 \le y \le 180$).

Specific examples as the unsaturated aliphatic hydrocarbon of the component (C1) include 1,4-pentadiene, 1,5-hexadiene, 1,6-heptadiene, 1,7-octadiene, 1,8-nonadiene, 1,9-decadiene, 1,11-dodecadiene, 1,13-tetradecadiene, 1,19-eicosadiene, 1,3-butadiene, 1,5-hexadiyne, and 1-hexen-5-yne.

The component (C1) can be used individually, or it is possible to use two or more types of components with different structures in combination. That is to say, the component (C1) may be a mixture of one or more types of organopolysiloxane and one or more types of unsaturated aliphatic hydrocarbon. Therefore, "having a number of unsaturated bonds greater than 1 on average" means having more than one unsaturated bond on average per molecule when two or more types of organopolysiloxanes and/or unsaturated aliphatic hydrocarbons are used.

The (C2) organic compound having at least one unsaturated bond and at least one epoxy group in a molecule serving as the component (C) is not structurally limited as long as the compound has a total of two or more, preferably from 2 to 10, more preferably from 2 to 7, even more preferably from 2 to 5, and particularly preferably from 2 to 4, unsaturated bonds and epoxy groups in a molecule, and straight, branched, or net-like organic compounds can be used. An organopolysiloxane or unsaturated aliphatic hydrocarbon is preferred as the organic compound. The position of the unsaturated bond in the organic compound, preferably organopolysiloxane or unsaturated aliphatic hydrocarbon, also is not limited, and the unsaturated bond may be positioned on the main chain or at a terminal. However, from the aspect of the ease of controlling the crosslinking density, it is preferable to use a compound of high purity in which the total of unsaturated groups and epoxy groups in a molecule is two.

It is preferred that an unsaturated bond is present in an unsaturated aliphatic hydrocarbon group. Examples of the utilized unsaturated aliphatic hydrocarbon group are as previously described.

When the component (C2) is an organopolysiloxane, the unsaturated aliphatic hydrocarbon group including an unsaturated bond and/or epoxy group preferably is bonded to a silicon atom. In addition, when the component (C2) is an organopolysiloxane, the group bonding to silicon atoms other than the unsaturated aliphatic hydrocarbon or the epoxy group may be a substituted or unsubstituted monovalent hydrocarbon group or a monovalent organic group having a reactive functional group as described above.

The component (C2) preferably is an epoxy group-containing unsaturated aliphatic hydrocarbon having at least one epoxy group. Examples of the unsaturated aliphatic hydrocarbon include compounds having the unsaturated aliphatic hydrocarbon groups described above. A compound having a monovalent unsaturated aliphatic hydrocarbon group is preferable.

Examples of the component (C2) include (C2-1) unsaturated epoxy compounds represented by the general formula (5-6):

[Formula 49]

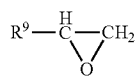

(5-6)

(in the formula, $R^9$ is a substituted or unsubstituted, straight or branched monovalent hydrocarbon group having one unsaturated bond and from 2 to 20 carbon atoms); and (C2-2) an unsaturated group-containing cycloaliphatic epoxy compound represented by the general formula (5-7):

General formula (5-7):

[Formula 50]

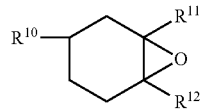

(5-7)

(in the formula, $R^{10}$ represents a substituted or unsubstituted, straight or branched monovalent hydrocarbon group having one unsaturated bond and from 2 to 20 carbons;
$R^{11}$ represents a hydrogen atom or methyl group; and
$R^{12}$ represents a hydrogen atom or methyl group). The definitions, types, and the like of the unsaturated bonds and the substituted or unsubstituted, straight or branched monovalent hydrocarbon groups in the general formulae above are as described above.

Specific examples of epoxy group-containing unsaturated aliphatic hydrocarbons serving as the component (C2) include allylglycidylether, methallylglycidylether, 1-methyl-4-isopropenylcyclohexene oxide, 1,4-dimethylcyclohexene oxide, 4-vinylcyclohexene oxide, vinylnorbornene monooxide, dicyclopentadiene monooxide, butadiene monooxide, 1,2-epoxy-5-hexene, 1,2-epoxy-9-decene, and 2,6-dimethyl-2,3-epoxy-7-octene. Among these, 4-vinyl cyclohexene oxide is preferable.

The component (C2) can be used individually, or it is possible to use two or more types of components with different structures in combination.

The hydrophilic derivative having a (D) reactive unsaturated group and a hydrophilic group including at least one hydrophilic unit selected from the hydrophilic units represented by the structural formulae (3-1) to (3-4) is not particularly limited as long as it has at least one unsaturated bond and a hydrophilic group, but the hydrophilic derivative is preferably a glycerin derivative having a carbon-carbon double bond at a molecular terminal. These are (poly)glycerin derivatives having reactive functional group, such as an alkenyl group, at a molecular terminal, such as an allyl(poly) glycerin, allyl polyglycidyl ether, or (poly)glycerin monoallyl ether, and can be synthesized according to known methods.

From the perspectives of affinity with oil agents, emulsion properties, and use as various types of treatment agents (surfactants or surface treatment agents), particularly use as powder treatment agents and use as cosmetic raw materials, the component (B) in the organopolysiloxane elastomer of the present invention specifically is (poly)glycerin-based compound that is a (poly)glycerinmonoallyl ether and (poly)glyceryl eugenol, having a monoglycerin, diglycerin, triglycerin, or tetraglycerin structure. The preferred structure of the glycerin residue part of the glycerin derivative group, the structure of the compounds for imparting the suitable derivative group, and the like are as described above.

The reactions for producing the organopolysiloxane elastomer of the present invention can be performed according to known methods in the presence or absence of reaction solvents. The reaction between the unsaturated group and the Si—H group in the present invention is a hydrosilylation reaction. In addition, when crosslinking is performed using an epoxide of (C2) the organic compound having one or more unsaturated bonds and one or more epoxy groups in a molecule, bonding caused by the reaction of the unsaturated group and the Si—H group and ether bond generation caused by the self ring-opening polymerization of the epoxy groups (cationic polymerization reaction that occurs in the presence of a SiH group and a platinum catalyst) both occur, resulting in crosslinking. It is possible to further promote this reaction by using high energy beam irradiation (ultraviolet radiation or the like) or further adding a general cation polymerization catalyst.

No particular limitation is placed on the reaction solvent as long as the reaction solvent is non-reactive. The reaction solvent is exemplified by alcohol-based solvents such as ethanol, isopropyl alcohol, and the like; aromatic hydrocarbon-based solvents such as toluene, xylene, and the like; ether-based solvents such as dioxane, THF, and the like; aliphatic hydrocarbon-based solvents such as n-hexane, cyclohexane, n-heptane, cycloheptane, methylcyclohexane, and the like; and chlorinated hydrocarbon-based organic solvents such as carbon tetrachloride and the like. The below described oil agents may also be used as reaction solvents. When an oil agent is used as the reaction solvent, a composition containing the organopolysiloxane and the oil agent can be directly obtained after the hydrosilylation reaction (crosslinking), and a composition containing a particulate organopolysiloxane elastomer and the oil agent, preferably a paste-like composition, can be easily obtained by using mechanical force to pulverize the product.

The hydrosilylation reaction may be performed in the presence or absence of a catalyst, but preferably is performed in the presence of a catalyst because the reaction can be carried out at a low temperature and in a shorter period of time. Examples of the hydrosilylation reaction catalyst include platinum, ruthenium, rhodium, palladium, osmium, iridium, and similar compounds, and platinum compounds are particularly effective due to their high catalytic activity. Examples of platinum compounds include chloroplatinic acid; platinum metal; platinum metal supported on a carrier such as alumina, silica, and carbon black; and platinum complexes such as platinum-vinylsiloxane complex, platinum-phosphine complex, platinum-phosphite complex, and platinum alcoholate catalyst. A usage amount of the catalyst is about 0.5 to 1000 ppm in terms of platinum metal, when using a platinum catalyst.

The reaction temperature of the hydrosilylation reaction normally is from 30 to 120° C., and reaction time normally is from 10 minutes to 24 hours and preferably from 1 to 10 hours.

Due to the hydrosilylation reaction or the cation polymerization reaction of the epoxy group, the component (A) is crosslinked by the component (C), and the polysiloxane chains derived from the component (A) are linked by crosslinking portion having the carbon-silicon bond derived from the component (C). The component (A) also comprises a siloxane dendron structure derived from the component (B). Then, when a component (D) is used, a glycerin derivative group derived from the component (D) is also provided. It is possible in this manner to obtain the organopolysiloxane elastomer of the present invention. However, the component (D) may also have more than one reactive unsaturated group in a molecule. In this case, the component (C) is not necessary because the component (D) also does the work of the component (C) as the crosslinking component.

Furthermore, although the organopolysiloxane elastomer of the present invention typically has a structure linked by crosslinking portion having the carbon-silicon bond derived from the component (C), a part of the organopolysiloxane elastomer of the present invention may have crosslinking parts due to Si—O—C bonds. When this structure has functional groups capable of condensation reaction (i.e. groups such as the silanol group, alkoxy group, and the like) in the components (A) to (C), if crosslinking conditions are severe (i.e. crosslinking can be formed between polysiloxane chains, and the like), it is possible to secondarily form such crosslinking by reactions such as partial reaction between hydroxyl groups in the glycerin derivative groups derived from the component (D) and the S—H groups of the component (A).

During production of the organopolysiloxane elastomer of the present invention, the component (A) and the component (B) may be reacted, followed by further reaction of the component (C) and/or component (D) with the component (A). It is also possible to react the component (A) and the component (C) and/or component (D), and then to further react the component (B) with the component (A).

When the component (C) and/or component (D) is further reacted with the component (A) after the reaction between the component (A) and the component (B), the average value of the number of silicon-bonded hydrogen atoms per molecule of the component (A) reacting with the unsaturated bonds of the component (C) and/or component (D) is preferably 0.1 or greater and less than 2. In other words, the number of silicon-bonded hydrogen atoms in a molecule of the component (A) that react with the unsaturated bonds in the component (C) and/or component (D), and which constitute the crosslinking portions, is, on average, not less than 1.0, preferably in a range of 0.2 to 1.5, and especially preferably in a range of 0.6 to 1.3.

Furthermore, the organopolysiloxane elastomer may be subjected to hydrogenation treatment for the purpose of improving the odor after the reaction caused by the remaining unsaturated compound. Methods of hydrogenation treatment include a method using pressurized hydrogen gas and a method using a hydrogenation agent such as a metal hydride, and further the hydrogenation treatments consist of homogeneous reactions and heterogeneous reactions. One of these methods may be performed alone, or multiple methods may be performed in combination. However, taking into consideration the advantage that the catalyst that is used will not remain in the finished product, a heterogeneous catalytic hydrogenation reaction using a solid catalyst is most preferable.

Examples of solid catalysts (hydrogenation catalyst) that can be used include noble metal-based catalysts such as common platinum-based catalysts and palladium-based catalysts, as well as nickel-based catalysts. More specific examples include single substances such as nickel, palladium, platinum, rhodium, and cobalt, and catalysts combining a plurality of metals such as platinum-palladium, nickel-copper-chromium, nickel-copper-zinc, nickel-tungsten, and nickel-molybdenum. Examples of optional catalyst carriers include activated carbon, silica, silica alumina, alumina, and zeolite. In addition, copper-containing hydrogenation catalysts such as Cu—Cr, Cu—Zn, Cu—Si, Cu—Fe—Al, and Cu—Zn—Ti may be used. The form of the hydrogenation catalyst differs depending on the type of the reaction vessel and therefore cannot be determined generally, but the form normally is appropriately selected from forms such as a powder, granules, or pellets. In addition, the platinum catalyst used in the synthesis process (hydrosilylation reaction) can be used as it is. These hydrogenation catalysts may be used alone or as a combination of two or more types of catalysts.

The hydrogenation treatment can also be used to refine a crude product of the organopolysiloxane elastomer obtained by the hydrosilylation reaction described above. Specifically, a crude product can be refined by deodorization by hydrogenation treatment in the presence of a hydrogenation catalyst, with or without a solvent, and such a refined product preferably used in applications as external use preparations or cosmetics in which reduced odor and compatibility with other components are desired. Moreover, the deodorizing treatment preferably has, as a pre-process or a post-process, a stripping treatment in which nitrogen gas is brought into contact with the crude product of the organopolysiloxane elastomer or the hydrogenated product to remove light matter under reduced pressure.

In addition to the component (A), component (B) and component (C) and/or component (D), an (Q) organic compound having one unsaturated bond in a molecule (excluding the component (C2)) may be further reacted in the production of the organopolysiloxane elastomer of the present invention. One type of component (Q) may be used, or two or more types of component (Q) may be used. The reactions preferably can be performed consecutively in the presence of the hydrosilylation reaction catalyst. Furthermore, the definitions, types, and the like of the unsaturated groups in the component (Q) are as described above.

For example, if the component (C) and/or the component (D) is further reacted with the component (A) after reaction between the component (A) and the component (B), the component (Q) may be reacted with the component (A) prior to reaction between the component (A) and the component (B), or the component (Q) may be reacted with the component (A) after reaction between the component (A) and the component (B), or the component (Q) may be reacted with the component (A) after reaction of the component (C) and/or the component (D).

Additionally, when the component (A) and the component (C) and/or the component (D) are reacted, and then the component (B) is further reacted with the component (A), the component (Q) may be reacted with the component (A) before the reaction between the component (A) and the component (C) and/or the component (D), the component (Q) may be reacted with the component (A) after the reaction between the component (A) and the component (C) and/or the component (D), or the component (Q) may be further reacted with the component (A) after the reaction with the component (B).

Examples of the component (Q) include chain organopolysiloxanes that have one reactive unsaturated group in a molecule or hydrocarbon compounds having one reactive unsaturated group in a molecule.

The hydrocarbon compound having one reactive unsaturated group in a molecule is preferably a monounsaturated hydrocarbons having from 9 to 30 carbons and is more preferably a 1-alkene. Examples of the 1-alkene include 1-nonene, 1-decene, 1-undecene, 1-dodecene, 1-tridecene, and 1-tetradecene. Examples of organopolysiloxane chains having a single reactive unsaturated group in a molecule include dimethylpolysiloxanes capped at one molecular terminal with a vinyl group and methylphenylpolysiloxanes capped at one molecular terminal with a vinyl group.

In the production of the organopolysiloxane elastomer of the present invention, it is preferred that the organopolysiloxane elastomer of the present invention obtained by a hydrosilylation reaction between the component (A), component (B), component (C) and/or component (D), and optional component (Q) is further subjected to an acid treatment step in which the obtained organopolysiloxane elastomer is treated with at least one type of acidic substance. It is possible to reduce odor of the organopolysiloxane elastomer by this step.

The acidic substance is not particularly limited and may be any acid that matches the definition of a Lewis-acid, a Bronsted acid, or an Arrhenius acid. The acidic substance used in the present invention preferably is a water soluble acid. Therefore, the acidic substance used in the present invention preferably is an Arrhenius acid that releases protons in an aqueous solution. One type of the acidic substance may be used alone, or two or more types of acidic substances may be used in combination. In the present invention, by using such an acidic substance, the organopolysiloxane elastomer can be substantially deodorized and the generation of odor over time can be completely suppressed without severing the carbon-oxygen bonds or the silicon-oxygen bonds.

The acidic substance can be selected from the group consisting of inorganic acids, organic acids, acidic inorganic salts, and acidic platinum catalysts.

The inorganic acids are not particularly limited, and examples thereof include hydrochloric acid, sulfuric acid, nitric acid, phosphoric acid, carbonic acid, boric acid, sulfonic acid, and sulfinic acid. Furthermore, substances including organic groups such as benzene sulfonic acid are not preferred as inorganic acids.

The organic acids are not particularly limited, and can be monocarboxylic acid (including monohydroxy monocarboxylic acid and dihydroxy monocarboxylic acid), dicarboxylic acid (including monohydroxy dicarboxylic acid and dihydroxy dicarboxylic acid), or polycarboxylic acid, or the like. Examples thereof include:

straight saturated aliphatic monocarboxylic acids (alkanoic acids) such as formic acid, acetic acid, trifluoroacetic acid, propionic acid, butyric acid, valeric acid, caproic acid, enanthic acid, caprylic acid, pelargonic acid, capric acid, and undecanoic acid;

branched saturated aliphatic monocarboxylic acids (alkanoic acids) such as 2-methylpropanoic acid, 2-methylbutanoic acid, trimethylpropanoic acid, 2-methylpentanoic acid, and trimethyl acetic acid;

unsaturated aliphatic monocarboxylic acids (alkenoic acids) such as acrylic acid, methacrylic acid, crotonic acid, isocrotonic acid, vinyl acetic acid, allyl acetic acid, hexenoic acid, heptenoic acid, and octenoic acid;

unsaturated aliphatic monocarboxylic acids (alkynoic acids) such as propiolic acid, tetrolic acid, allyl acetic acid, hexynoic acid, and octynoic acid;

polyunsaturated aliphatic monocarboxylic acids such as pentadienoic acid, and sorbic acid;

α-hydroxymonocarboxylic acids such as citric acid, lactic acid, glycolic acid, and α-oxybutyric acid;

β-hydroxymonocarboxylic acids such as 2-hydroxyvaleric acid, 2-hydroxycaproic acid, and β-oxybutyric acid;

γ-hydroxymonocarboxylic acids such as γ-oxybutyric acid and the like;

dihydroxymonocarboxylic acids such as glyceric acid;

other hydroxymonocarboxylic acids such as hydroxy(meth)acrylic acid;

saturated aliphatic dicarboxylic acids such as oxalic acid, malonic acid, succinic acid, glutaric acid, and adipic acid;

monohydroxy saturated aliphatic dicarboxylic acids such as tartronic acid, and malic acid;

dihydroxy saturated aliphatic dicarboxylic acids such as tartaric acid;

unsaturated aliphatic dicarboxylic acids such as maleic acid and fumaric acid;

aromatic monocarboxylic acid such as benzoic acid;

aromatic dicarboxylic acids such as phthalic acid;

amino acids such as glycine, alanine, valine, leucine, glutamic acid, aspartic acid, and PL-pyrrolidone carboxylic acid; and polycarboxylic acids such as gallic acid.

In addition, alkyl sulfuric acid, alkyl phosphoric acid, phenol, and the like can be used as the organic acid. Furthermore, higher fatty acids or salts thereof are not preferred as organic acids.

The acidic inorganic salts are not limited, but a water soluble salt is preferred. Particularly preferable is a water soluble acidic inorganic salt that is solid at 25° C. and, when 50 g thereof is dissolved in 1 L of ion exchanged water, the solution has a pH at 25° C. of 4 or lower, preferably 3.5 or lower, and more preferably 2.0 or lower. When the acidic inorganic salt is a solid at room temperature (25°), the acidic inorganic salt may be readily removed by filtration, as required. Moreover, if the acidic inorganic salt is water soluble, the acidic inorganic salt may be readily rinsed using water, as required. The value of pH for the present invention is the value of a sample aqueous solution measured using a pH meter equipped with a glass electrode at room temperature (25° C.).

Examples of the acidic inorganic salt that can be used include acidic inorganic salts in which at least a monovalent hydrogen atom of an inorganic acid that is at least divalent is neutralized by a base. Examples of inorganic acids that are at least divalent include sulfuric acid and sulfurous acid. Examples of bases include alkali metals and ammonia.

More specifically, the acidic inorganic salt is preferably at least one type of acidic inorganic salt comprising a hydrogen sulfate ion ($HSO_4^-$) or a hydrogen sulfite ion ($HSO_3^-$) and a monovalent cation ($M^+$). Examples of the monovalent cation ($M^+$) include alkali metal ions or an ammonium ion. Particularly, the monovalent cation is preferably at least one type selected from the group consisting of a sodium ion, a potassium ion, and an ammonium ion.

Specific examples of the acidic inorganic salt include lithium hydrogen sulfate, sodium hydrogen sulfate, potassium hydrogen sulfate, rubidium hydrogen sulfate, cesium hydrogen sulfate, ammonium hydrogen sulfate, sodium hydrogen sulfite, hydrates of such salts, and Lewis acids such as $AlCl_3$, $FeCl_3$, $TiCl_4$, $BF_3 \square Et_2O$, and the like. For several acidic inorganic salts, the pH values of aqueous solutions when 50 g of the acidic salt is dissolved in 1 L of ion exchanged water are shown in the table below. From the perspective of the technical benefit of reducing odor, the water soluble acidic inorganic salt having a pH of not higher than 2.0 is preferably at least one type of acidic inorganic salt selected from the group consisting of sodium hydrogen sulfate, potassium hydrogen sulfate, and ammonium hydrogen sulfate.

TABLE 1

| Acidic inorganic salt | pH (50 g/L) |
| --- | --- |
| Sodium hydrogensulfate | 1.5 or lower |
| Potassium hydrogensulfate | 2.0 or lower |
| Ammonium hydrogensulfate | 1.5 or lower |
| Sodium hydrogensulfite | 3.5 |

Examples of acidic platinum catalysts that can be used include chloroplatinic acids, alcohol-modified chloroplatinic acids, olefin complexes of chloroplatinic acids, ketone complexes of chloroplatinic acids, vinylsiloxane complexes of chloroplatinic acids, and platinum tetrachlorides. Of these, chloroplatinic acid is preferable.

The acid treatment step may be performed by contacting the organopolysiloxane elastomer with the acidic substance according to a desired embodiment.

Specifically, the acid treatment step can be performed by, e.g., an operation such as heated stirring, kneading, or pulverization in which at least one type of the acidic substances and optionally water and/or an organic solvent such as alcohol are added to a reaction system (e.g. in reaction vessel such as a flask or the like, or a mixing/powder crushing vessel, emulsification equipment, or the like) containing the organopolysiloxane elastomer, or by repeating the above operation. Alternatively and further preferably, the organopolysiloxane elastomer, or a composition including the organopolysiloxane elastomer and an oil agent, may undergo pulverization pre-treatment. Then, at least one type of the acidic substance is added, optionally together with water and/or an organic solvent such as an alcohol and the like, and the mixture is processed by heating and stirring, or the like.

The acid treatment step can be carried out at any temperature and treatment time, and can be carried out at a temperature from 0 to 200° C., and more preferably from 50 to 100° C., for a reaction time of from 0.5 to 24 hours, and more preferably from about 1 to 10 hours. Furthermore, such treatment is preferably performed in the presence of a solvent such as a lower monohydric alcohol or the like. The quantity of the acidic substance used can be appropriately selected in accordance with the acid strength, treatment equipment, treatment time, and treatment temperature. However, when the acidic substance is one with moderate acid strength such as sodium hydrogensulfate, potassium hydrogensulfate, ammonium hydrogensulfate, citric acid, glycolic acid, or phosphoric acid, the content preferably is in a range of 100 to 1000 ppm and more preferably in a range of 150 to 500 ppm in the organopolysiloxane elastomer of the present invention. Additionally, when the acidic substance is one with high acidic strength such as hydrochloric acid or sulfuric acid, the content preferably is in a range of 1 to 100 ppm in the organopolysiloxane elastomer, and in the case of a weak acidic substance with a low acidic strength, the content preferably is in a range of 1,000 to 10,000 ppm in the organopolysiloxane elastomer.

In the production method for the organopolysiloxane elastomer of the present invention, after the acid treatment step, there is preferably a heating and/or pressure reduction step (stripping step). The heating and/or pressure reduction is capable of removing (stripping off) the low-boiling components, i.e. odor-causing substances. Moreover, after the stripping, it is possible to remove more odor-causing substances by again performing the acid treatment step. At this time, when acidic substance remains in the reaction system, there is a benefit that it is unnecessary to newly add acidic substance and it is sufficient to add only water. That is to say, the acid treatment step and stripping step may be each repeated two or more times with objects such as increasing the degree of deodorizing or the like.

The "low-boiling components" removed by the stripping step, in addition to substances thought to cause odor such as carbonyl compounds (propionaldehyde or the like), also includes volatile components such as the reaction solvent, or the like used in the synthesis of the organopolysiloxane elastomer.

Furthermore, the stripping step may be performed prior to the acid treatment step.

Commonly known reaction conditions can be employed in the stripping method, but stripping under atmospheric pressure or reduced pressure is preferable, and it is preferably performed at 120° C. or lower. For efficient stripping, stripping preferably is performed under reduced pressure or performed, e.g., under a nitrogen gas or similar inert gas stream. A specific example of the low-boiling components removal operation is one in which the organopolysiloxane elastomer or composition thereof or a hydrogenated product thereof comprising a low-boiling components is placed in a flask having a refluxing cooler, a nitrogen injection port, or the like. While nitrogen gas is supplied, the internal pressure is reduced and the temperature is increased, and the pressure and temperature are then kept constant so as to remove light matter. Here, typically, a pressure reduction parameter is from 0.1 to 10.0 kPa, a heating temperature is from 50 to 120° C., and a treatment time is from 10 minutes to 24 hours.

Following this acid treatment step, the organopolysiloxane elastomer may also be neutralized by a basic substance in the present invention. One type of basic substance may be used alone, or alternatively, two or more basic substance may be used. The basic substance is exemplified by inorganic bases such as sodium hydroxide, potassium hydroxide, calcium hydroxide, barium hydroxide, ammonia water, sodium hydrogen carbonate, and the like; basic buffering agents such as trisodium phosphate, tripotassium phosphate, sodium citrate, sodium acetate, and the like; and organic bases such as basic amino acids, amines, pyridines, and the like. An amount of the basic substance is preferably an amount needed to neutralize a reaction system comprising the organopolysiloxane elastomer but, as necessary, the amount of the basic substance may be adjusted to an amount by which weak acidity or weak alkalinity is obtained.

The organopolysiloxane elastomer of the present invention is preferably in the form of particles, and further preferably is in the form of solid particles.

This particulate organopolysiloxane can be obtained simply by using mechanical force to pulverize cured organopolysiloxane elastomer, and solid organopolysiloxane elastomer particles of a desired particle size can be obtained by using commonly known methods to adjust the pulverization parameters. Furthermore, pulverization may be performed by mixing an oil agent with the organopolysiloxane elastomer before or after primary pulverization, and then using mechanical force to perform primary pulverization or finer secondary pulverization of this organopolysiloxane elastomer in a dispersed or swollen state due to the oil agent.

No particular limitation is placed on the mechanical means used for pulverizing the organopolysiloxane elastomer or composition. However, the pulverization method is preferably at least one method selected from methods such as shearing, kneading, or passing through an orifice under pressure.

On the other hand, an aqueous dispersion of the organopolysiloxane elastomer particles can be obtained by emulsifying/dispersing in water the organopolysiloxane elastomer raw material composition prior to curing, and then crosslinking the emulsion, and it is possible to then obtain the organopolysiloxane elastomer particles by removing water from the aqueous dispersion and drying the organopolysiloxane elastomer particles.

No particular limitation is placed on the diameter of the organopolysiloxane elastomer particles, and this diameter may be selected according to application and feel. However, from the standpoint of formulation of the below described composition with the oil agent, volume average particle diameter as measured using microscopic observation or a particle diameter distribution measurement apparatus is preferably in a range of 20 to 1,000 μm, and further preferably is in a range of 25 to 300 μm.

(Composition Including the Organopolysiloxane Elastomer)

The present invention also relates to a composition that includes the organopolysiloxane elastomer. No particular limitation is placed on the blended amount of the organopolysiloxane elastomer in the composition. For example, this blended amount relative to the total weight (mass) of the composition is in a range of 5 to 80 wt. % (mass %), preferably is in a range of 10 to 60 wt. % (mass %), further preferably is in a range of 15 to 50 wt. % (mass %), yet further preferably is in a range of 20 to 40 wt. % (mass %), and most preferably is in a range of 25 to 35 wt. % (mass %).

The composition of the present invention may further comprise at least one type of oil agent in addition to the organopolysiloxane elastomer. No particular limitation is placed on the oil agent, and a solid, semisolid, or liquid oil agent may be used. Specific examples include one type or two or more types of oil agent selected from silicone oils, hydrocarbon oils, ester oils, vegetable oils and fats, animal oils and fats, fatty acids, higher alcohols, triglycerides, artificial sebums, and fluorocarbon type oil agents. These specific examples are as described in another patent application for which priority right is asserted based on Japanese Patent Application No. 2011-121097 (relating to a sugar alcohol-modified silicone elastomer), the content of which is incorporated herein for reference, and the organopolysiloxane elastomer of the present invention is capable of stably maintaining various types of powders dispersed in an oil phase containing such silicone oils and the like, and is capable of stably emulsifying/dispersing a water phase in an oil phase containing such silicone oils, and the like. Moreover, from the standpoint of improving environmental suitability and switching to a PEG-free formulation for the overall composition of the cosmetic or external use preparation, an oil agent is preferably selected that has a non-POE (polyoxyethylene) structure.

No particular limitation is placed on the blended amount of the oil agent in the composition of the present invention. For example, this blended amount relative to the total weight (mass) of the composition is in a range of 20 to 95 wt. % (mass %), preferably is in a range of 40 to 90 wt. % (mass %), further preferably is in a range of 50 to 85 wt. % (mass %), still further preferably is in a range of 60 to 80 wt. % (mass %), and most preferably is in a range of 65 to 75 wt. % (mass %).

The organopolysiloxane elastomer of the present invention functions as a surfactant or emulsifier due to having a hydrophobic silicone chain and a hydrophilic group typified by a glycerin derivative group. Thus, the composition including the organopolysiloxane elastomer of the present invention and at least one type of oil agent may be in the form of an emulsion. No particular limitation is placed on the emulsion form, and any desired form may be used, such as an aqueous-oil type emulsion composition such as an oil-in-water emulsion, water-in-oil emulsion, and the like; or an oil-in-alcohol emulsion, alcohol-in-oil emulsion (e.g. polyol as the alcohol), or the like.

The average particle diameter of the emulsion particle emulsified by the organopolysiloxane elastomer of the present invention may be measured by a known measurement apparatus using the laser diffraction method, laser scattering method, or the like. The emulsion composition of the present invention is preferably a polar solvent-in-oil type emulsion, although an oil-in-polar solvent type emulsion is also permissible. In addition, the emulsion composition of the present invention may be a transparent micro-emulsion in which the measured average particle size is 0.1 μm or less or may be a large particulate white turbid emulsion in which the average particle size exceeds 10.0 μm. Furthermore, the emulsion particles may be micronized for the purpose of improving the stability and transparent appearance of the emulsion. An emulsion having a particle size from 0.5 to 20 μm can be selected for the purpose of improving sensation during use and adhesion properties to hair and skin.

The aforementioned emulsion or the like may be produced by mixing with water by use of mechanical forced using an apparatus to mix the organopolysiloxane elastomer of the present invention, or the composition including the organopolysiloxane elastomer of the present invention. The mixing apparatus is exemplified by a homomixer, paddle mixer, Henschel mixer, homo-disper, colloid mill, propeller stirrer, homogenizer, in-line continuous emulsification device, ultrasonic emulsification device, vacuum kneader, or the like.

Moreover, the utilized amounts and blend ratios of water in the method for producing the emulsion composition are as described above. According to the form of the emulsion and the application of the emulsion, the amount in the entire emulsion composition may be selected appropriately in a range of 1 to 99 wt. % (mass %).

The composition of the present invention, which includes at least one type of oil agent in addition to the organopolysiloxane elastomer, may be used in the form of a paste.

The organopolysiloxane elastomer blended in the composition of the present invention is preferably in the form of particles. Although any blending ratio (weight (mass) ratio) with the oil agent may be used, from the standpoint of obtaining a paste-like composition formed from fine and uniform particles that are free of the sensation of a foreign body, this blending ratio is preferably in a range of 5/95 to 50/50, particularly preferably is in a range of 10/90 to 40/60, and most preferably is in a range of 15/85 to 30/70. In particular, when the organopolysiloxane elastomer swells due to a mass of the oil agent at least the same as the mass of the organopolysiloxane elastomer itself, the organopolysiloxane elastomer is readily made to swell using an amount of the oil agent at least that of the organopolysiloxane elastomer, and preferably a paste-like composition may be readily prepared.

The composition including the oil agent and the particulate organopolysiloxane elastomer may be obtained by pulverizing the organopolysiloxane elastomer using mechanical force and then mixing with the oil agent. Alternatively, a mixture of the organopolysiloxane elastomer and the oil agent may be pulverized using mechanical force to obtain the composition including the oil agent and the particulate organopolysiloxane elastomer.

The composition of the present invention may contain water. No particular limitation is placed on the blended amount of water in the composition of the present invention. For example, this blended amount relative to the total amount (mass) of the composition is in a range of 1 to 90 wt. % (mass %), preferably is in a range of 5 to 80 wt. % (mass %), further preferably is in a range of 10 to 70 wt. % (mass %), still further preferably is in a range of 20 to 60 wt. % (mass %), and most preferably is in a range of 30 to 50 wt. % (mass %).

The composition of the present invention may further contain at least one type of alcohol. The alcohol preferably is a water-miscible alcohol, and more preferably a lower alcohol or polyhydric alcohol. Specific examples and utilized quantities of the alcohol are as described in the other patent application for which priority right is asserted based on Japanese Patent Application No. 2011-121097 (relating to a sugar alcohol-modified silicone elastomer), the content of which is incorporated herein for reference, and from the standpoint of improving environmental compatibility and switching to a completely PEG-free formulation for cosmetics or external use preparations, the alcohol preferably is selected from non-polyether structure polyhydric alcohols and/or lower monohydric alcohols.

The compounded amount of the alcohol in the composition of the present invention is not particularly limited but, for example, can be set in a range from 0.1 to 50 wt. % (mass %), preferably from 1 to 40 wt. % (mass %), more preferably from 2 to 30 wt. % (mass %), even more preferably from 3 to 20 wt. % (mass %), and even more preferably from 4 to 10 wt. % (mass %) based on the total weight (mass) of the composition.

The organopolysiloxane elastomer of the present invention or the composition including the organopolysiloxane elastomer of the present invention has fundamentally little tendency to oxidize and change in properties due to oxidation by oxygen in the air. Thus, it is not necessary to add a phenol, a hydroquinone, a benzoquinone, an aromatic amine, a vitamin, or similar antioxidant in order to prevent oxidation deterioration; or take steps to increase oxidation stability. However, adding such an antioxidant, for example, BHT (2,6-di-t-butyl-p-cresol), vitamin C, vitamin E, or the like, will result in a further increase in stability. In this case, an added amount of the antioxidant that is used is in a range (by weight (mass)) from 10 to 1,000 ppm, and preferably from 50 to 500 ppm, of the organopolysiloxane elastomer.

(External Use Preparation Raw Material or Cosmetic Raw Material)

The organopolysiloxane elastomer of the present invention or the composition comprising the same may be used appropriately as an external use preparation raw material or cosmetic raw material used for the human body. In particular, a paste-like composition containing the particulate organopolysiloxane elastomer of the present invention and an oil agent may be used without modification as an external use preparation raw material or cosmetic raw material.

The proportion of organopolysiloxane elastomer or the proportion of the composition containing the organopolysiloxane elastomer in the external use preparation raw material or cosmetic raw material relative to the raw material (total weight (mass) basis) is preferably from 10 to 50 wt. % (mass %), further preferably is from 15 to 40 wt. % (mass %), and most preferably is from 20 to 30 wt. % (mass %). A proportion of the raw material compounded in the external use preparation or the cosmetic is not particularly limited but, for example, can be from 0.1 to 90 wt. % (mass %), and is preferably from 1 to 80 wt. % (mass %), more preferably from 2 to 70 wt. % (mass %), and even more preferably from 5 to 50 wt. % (mass %) based on the total weight (mass) of the external use preparation or the cosmetic.

Examples of the external use preparation raw material or cosmetic raw material of the present invention include oil phase gelling agents, oil phase structuring agents, oil phase thickeners, tactile sensation improvers, moisturizing agents, masking agents such as wrinkle concealment agents, surfactants, emulsifiers, and power dispersion stabilizers.

(External Use Preparations and Cosmetics)

The organopolysiloxane elastomer of the present invention or composition comprising the same, or raw materials for external use preparations and cosmetics that contain the organopolysiloxane elastomer or composition containing the same, may be suitably blended in an external use preparation or cosmetic, whereby the external use preparation or cosmetic of the present invention can be constituted. Also, the external use preparation or cosmetic of the present invention is preferably contained in a container produced from a thermoplastic substance or a non-thermoplastic substance. Moreover, the container may have at least one compartment, and a unit for an external use preparation or for cosmetic use may be constituted using this container and the cosmetic or external use preparation of the present invention. Also, the external use preparation or cosmetic of the present invention may be used appropriately for a keratin-type substance such as skin, hair, or the like as a non-medical beautifying method mainly in order to apply a cosmetic (makeup) or care product (e.g. treatment for dry skin).

The external use preparation is a product to be applied to human skin, nails, hair, and the like and, for example, medicament active components can be compounded therein and used in the treatment of various disorders. The cosmetic is also a product to be applied to human skin, nails, hair, and the like, and is used for beauty purposes. The external use preparation or cosmetic, for example, is preferably a skin external use preparation or skin cosmetic, skincare cosmetic, sun care cosmetic, anti-perspirant, foundation, colored cosmetic, external use preparation for hair, or hair cosmetic.

The skin external use preparation or skin cosmetic of the present invention includes the organopolysiloxane elastomer of the present invention or includes the composition comprising the same. No particular limitation is placed on the form of the skin external use preparation or skin cosmetic of the present invention, and this form is exemplified by a liquid, cream-like, solid, semi-solid, paste-like, gel-like, powder-like, multi-layer, mousse-like, and spray. Specific examples of the skin external use preparation or the skin cosmetic product according to the present invention include toilet water, emulsions, creams, sunscreen emulsions, sunscreen creams, hand creams, cleansing compositions, massage lotions, cleansing agents, anti-perspirants, deodorants, and similar basic cosmetic products; foundations, make-up bases, blushers, rouges, eye shadows, eye liners, mascaras, nail enamels, and similar make-up cosmetic products; and the like.

In the same manner, the hair external use preparation or hair cosmetic of the present invention includes the organopolysiloxane elastomer of the present invention or includes the composition comprising the same; and various forms may be used. For example, the hair external use preparation or the hair cosmetic of the present invention may be dissolved or dispersed in an alcohol, a hydrocarbon, a volatile cyclic silicone, or the like and used; furthermore, these may be used in the form of an emulsion by dispersing a desired emulsifier in water. Additionally, the hair external use preparation or the hair cosmetic of the present invention can be used as a spray by using propane, butane, trichloromonofluoromethane, dichlorodifluoromethane, dichlorotetrafluoroethane, carbonic acid gas, nitrogen gas, or a similar propellant. Examples of other forms include milk-like, cream-like, solid, semi-solid, paste-like, gel-like, powder-like, multi-layer, mousse-like, and similar forms. These various forms can be used as shampooing agents, rinsing agents, conditioning agents, setting lotions, hair sprays, permanent wave agents, mousses, hair colorants, and the like.

The following other components generally used in external use preparations or cosmetics may be added to the external use preparation or the cosmetic of the present invention, provided that such components do not inhibit the effectiveness of the present invention: water, powders or coloring agents, alcohols, water-soluble polymers, film-forming agents, oil agents, oil-soluble gelling agents, organomodified clay minerals, surfactants, resins, mediums allowable in cosmetic products, adipose phases, film-forming polymers, fibers, light protection systems capable of blocking UV rays, UV absorbers, moisturizing agents, preservatives, antimicrobial agents, perfumes, salts, antioxidants, pH adjusting agents, chelating agents, refreshing agents, anti-inflammatory agents, skin beautifying components (skin-lightening agents, cell activating agents, agents for ameliorating skin roughness, circulation promoters, skin astringents, antiseborrheic agents, and the like), vitamins, amino acids, nucleic acids, hormones, clathrates, and the like; bioactive substances, medicament active ingredients, and perfumes. However, the additives are not particularly limited thereto. Specific examples, methods of use, compounding objectives, and utilized quantities of these cosmetic components are as described in the other patent application for which priority right is asserted based on Japanese Patent Application No. 2011-121097 (relating to a sugar alcohol-modified silicone elastomer), the content of which is incorporated herein for reference. Moreover, from the standpoint of increasing environmental compatibility and switching to a PEG-free formulation for the entire composition of the cosmetic or external use preparation, a formulation is preferred in which the cosmetic raw materials are non-polyether structure type water-soluble polymers, surfactants, emulsifiers, film-forming agents, moisturizing agents, or the like.

The organopolysiloxane elastomer of the present invention or the composition comprising the same is preferably used in combination with an organic-based UV absorber. Generally, the organic-based UV absorber has high polarity and does not readily dissolve. Therefore, conventionally, it has been difficult to stably compound a desired (high) amount of the organic-based UV absorber in water-in-oil (W/O) emulsion cosmetics. However, if the organopolysiloxane elastomer of the present invention is used as an emulsifier, and if an intermediate polarity oil (ester oil or the like) is jointly used as a binding agent, even if a low polarity oil (e.g., silicone oil, hydrocarbon oil, or the like) is included in the oil phase, it is possible to obtain a W/O emulsion cosmetic in which is stably blended a UV absorber, and it is possible to finely disperse the UV absorber in the preparation in a stable manner. This therefore results in a further excellent sun care effect. In this case, the mono-glycerin and/or di-glycerin derivative-modified organopolysiloxane elastomer of the present invention is preferably used in combination with a xylitol-modified silicone having a siloxane dendron structure and long-chain alkyl groups, or a diglycerin-modified silicone having a siloxane dendron structure and long-chain alkyl groups, as a secondary emulsification agent. In this case, the compounded amount of the organic-based UV absorber is preferably in a range of 0.1 to 10 mass %, and the compounded amount of the binding agent is preferably in a range of 0.005 to 5 mass %.

[Combination with Other Silicone-Based Cosmetic Raw Materials]

In the external use preparation or cosmetic of the present invention, according to the form thereof and formulation, solid silicone resins, crosslinking organopolysiloxanes (other than the organopolysiloxane elastomer of the present invention), acryl silicone dendrimer copolymers, silicone raw rubbers (silicone rubbers), polyamide-modified silicones, alkyl-modified silicone waxes, and alkyl-modified silicone resin waxes may be further blended. The organopolysiloxane elastomer of the present invention may have a main chain that is constituted from a polysiloxane chain, have a group having a siloxane dendron structure as a modifying group, and further have a hydrophilic group or long-chain alkyl group made primarily from a glycerin derivative, and therefore has the advantages of having excellent blending stability with these silicone-based compounds, and of being able to design cosmetics make use of the characteristic feel of these silicone-based cosmetic raw materials.

Specific examples, methods of use, compounding objectives, and utilized quantities of these silicone-based cosmetic raw materials are as described in the other patent application for which priority right is asserted based on Japanese Patent Application No. 2011-121097 (relating to a sugar alcohol-modified silicone elastomer), the content of which is incorporated herein for reference. Similarly, the advantageous effects obtained when the organopolysiloxane elastomer of the present invention is combined with these silicone-based cosmetic raw materials are as described in the other patent application for which priority right is asserted based on Japanese Patent Application No. 2011-121097 (relating to a sugar alcohol-modified silicone elastomer), the content of which is incorporated herein for reference. Moreover, from the standpoint of increasing environmental compatibility and switching to a PEG-free formulation for the entire composition of the cosmetic or external use preparation, a formulation is preferred that selects a combination with silicone-based cosmetic raw materials that do not include a polyether structure.

Additionally, in cases where the external use preparation or the cosmetic according to the present invention is an antiperspirant, or depending on the purpose thereof, the external use preparation or the cosmetic can contain an anti-perspiration active component and/or a deodorant agent. Examples of the deodorant agent include deodorizers, perfumes, and substances that prevent or remove odors caused by perspiration. Such deodorant agents are antimicrobial agents (germicides or fungicides), bacteriostatic agents, odor absorbing substances, deodorizers, perfumes, or the like, and are compounded for the purpose of preventing underarm odor, odor from perspiration, foot odor, and other bodily odors. Note that these deodorant agents are useful in cosmetics or external use preparations other than anti-perspirants and it goes without saying that they can be beneficially compounded in the cosmetic or external use preparation of the present invention.

Specific examples, methods of use, compounding objectives, and utilized quantities of these antiperspirant active ingredients, deodorant agents, or the like are as described in the other patent application for which priority right is asserted based on Japanese Patent Application No. 2011-121097 (relating to a sugar alcohol-modified silicone elastomer), the content of which is incorporated herein for reference.

(Carbonyl Value Measurement Method)

The degree of odor of the organopolysiloxane elastomer of the present invention or the composition comprising the same may be determined by the carbonyl value, which is measured from the absorbance of a reaction liquid obtained by reaction with the organopolysiloxane elastomer of the present invention or the composition comprising the same and 2,4-dinitrophenylhydrazine (2,4-DNPH) in a reaction medium containing at least one type of monohydric lower alcohol having from 1 to 4 carbons. Furthermore, in addition to a compound having a carbonyl group such as an aldehyde or a ketone, the "carbonyl compound" also includes a potential carbonyl compound such as an acetal, propenyl ether, or a similar compound that does not comprise a carbonyl group but generates a carbonyl group by decomposing under certain conditions.

Thus, in order to quantitatively determine the degree of odor of the organopolysiloxane elastomer of the present invention or the composition comprising the same, the carbonyl compound-containing organopolysiloxane elastomer or composition containing the organopolysiloxane elastomer and 2,4-dinitrophenylhydrazine are reacted in a reaction medium containing at least one type of monohydric lower alcohol having from 1 to 4 carbons, and the carbonyl value may be measured for the organopolysiloxane elastomer or composition comprising the same based on absorbance of the reaction liquid obtained from the reaction. Details and the specific measurement method are as described in the other patent application for which priority right is asserted based on Japanese Patent Application No. 2011-121097 (relating to a sugar alcohol-modified silicone elastomer), the content of which is incorporated herein for reference. Here, the "carbonyl value" is the carbonyl content index value, and is a value obtained by converting the absorbance (absorbance at 430 nm or 460 nm) of the reaction solution, obtained by reacting 2,4-DNPH with the sample, to per 1 g of sample. Furthermore, the measurement of the carbonyl value can quantitatively measure carbonyl compounds accurately and easily, and this method thus has the advantage of being able to be used appropriately for the evaluation of odor of an external use preparation or cosmetic.

For the organopolysiloxane elastomer of the present invention or the composition comprising the same, the carbonyl value measured by the aforementioned method is preferably less than or equal to 2.5 Abs/g, further preferably is less than or equal to 1.6 Abs/g, and most preferably is less than or equal to 1.2 Abs/g.

Industrial Field of Use

The organopolysiloxane elastomer of the present invention or the composition comprising the same may be used with advantage as an external use preparation raw material or a cosmetic raw material. Odor is reduced for the organopolysiloxane elastomer of the present invention produced using the acid treatment step and the composition of the present invention comprising the organopolysiloxane elastomer. Therefore, blending is possible with advantage in an external use preparation or cosmetic.

PRACTICAL EXAMPLES

The present invention is described below using practical examples, but the present invention is not limited thereto. Furthermore, in the below described composition formulae, the $Me_3SiO$ group (or $Me_3Si$ group) is represented as M, the $Me_2SiO$ group is represented as D, the $Me_2HSiO$ group (or $Me_2HSi$ group) is represented as $M^H$, the MeHSiO group is represented as $D^H$, the unit in which one of the methyl groups of M is modified by a substituting group is represented by $M^R$, the unit in which one of the methyl groups of D is modified by a substituting group is represented by $D^R$, Furthermore, although the "production of silicone compound No. X" or the like are described in the below described practical examples and comparative examples, the obtained product is in the form of a mixture that includes the main component as well as minor amounts of unreacted raw materials, diluents, or the like.

Practical Example 1

Production of Silicone Compound No. 1

A reaction vessel was loaded with 170.1 g of methylhydrogen polysiloxane represented by the average composition formula: $MD_{43.2}D^H{}_{8.2}M$, 6.0 g of 3-methacryloxypropyl(tris (trimethylsiloxy) silylethyl dimethylsiloxy) silane represented by the following average composition formula:

[Formula 51]

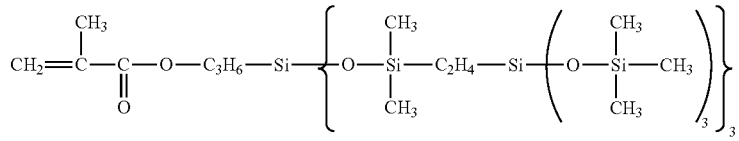

and 30.7 g of hexadecene (α-oefin purity: 91.7%), which was then heated to 30° C. while stirring under a nitrogen flow. 0.10 mL of a hexamethyldisiloxane solution of platinum-1,3-divinyl-1,1,3,3-tetramethyldisiloxane complex (Pt concentration: 0.45 wt. %) were added and heated to 55° C. and reacted for 1 hour. When a small quantity of the reaction liquid was sampled and the reaction rate calculated by the alkali decomposition gas generation method (remaining Si—H groups are decomposed by an ethanol/water solution of KOH, and the reaction rate is calculated from the volume of hydrogen gas generated), it was found that a modified silicone intermediate represented by $MD_{43.2}D^{R*31}{}_{0.1}D^{R*11}{}_{3.1}D^H{}_{4.7}D^{OR}{}_{0.3}M$ had been produced. Next, a solution made from 19.7 g of diglycerin monoallyl ether, 0.02 g of natural vitamin E, and 138 g of isopropyl alcohol (IPA) was added to the reaction mixture, and another 0.20 mL of the platinum catalyst was added, and reacted for 5.5 hours at 50 to 60° C., and when the reaction rate was subsequently checked by the same method, it was found that a modified silicone intermediate represented by the average composition formula $MD_{43.2}D^{R*31}{}_{0.1}D^{R*21}{}_{1.84}D^{R*11}{}_{3.1}D^H{}_{2.86}D^{OR}{}_{0.3}M$ had been produced. Here, $R^{*11}$, $R^{*21}$, and $R^{*31}$ are as described below.

Moreover, $D^{OR}$ is a structural unit generated by dehydrogenation reaction with $D^H$ and an alcoholic hydroxyl group or moisture, and this is a Me(OR)SiO group including a Si—O—C bond or Si—O—H bond.

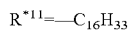

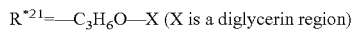

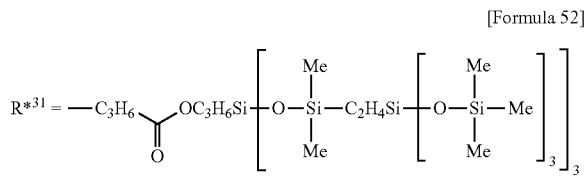

[Formula 52]

Next, 230 g of caprylyl methicone, which is both a diluent and crosslinking reaction solvent, were added and the reaction liquid was mixed, and then IPA was removed by distillation under reduced pressure. The temperature of the reaction mixture at this time was 40 to 55° C.

After cooling to 50° C., 5.93 g of 1,5-hexadiene and 0.25 mL of the platinum catalyst were added and stirred for 70 minutes at 50° C., at which time the viscosity of the homogenous semitransparent reaction liquid increased slightly. Furthermore, the Vi/H mole ratio of the crosslinking reaction was 1.20.

Furthermore, the reaction liquid was heated to 50 to 60° C. and aging was continued for another 2 hours without stirring to complete the production of the organopolysiloxane elastomer of the present invention (production of 450 g of a composition containing the organopolysiloxane elastomer of the present invention and caprylyl methicone, elastomer concentration: 50%).

Next, the composition was removed from the reaction vessel and divided in thirds, loaded into a high-shear mixer at a ratio of 326 g of caprylyl methicone per 150 g of the composition, and subjected for 30 minutes to shearing and pulverizing treatment, whereupon a homogenous paste-like composition was obtained with absolutely no sense of foreign objects when touched. This operation was similarly performed on the remaining unpulverized composition (150 g×two batches) to yield similar homogenous paste-like compositions.

Another reaction vessel was loaded with the 1,418 g of the homogenous paste-like composition, to which a 0.03 g of sodium hydrogen sulfate monohydrate, 3.6 g of purified water, and 92 g of IPA were added, and then mixed by stirring for 1 hour at 70 to 80° C., after which, the pressure was reduced and the low-boiling components were distilled out (first acidizing treatment). For a second time, 3.6 g of purified water and 92 g of IPA were added and the same treatment was performed, after which, the pressure was reduced and the low-boiling components were distilled out (second acidizing treatment). This operation was performed once more (third acidizing treatment), and then 23 g of 0.1% sodium bicarbonate water was added and stirred to neutralize the mixture. Immediately thereafter, the mixture was heated to 70 to 105° C. under reduced pressure and the low-boiling components were distilled out to yield a homogenous paste-like composition containing a novel organopolysiloxane elastomer that had been modified with a siloxane dendron structure, a hydrophilic group, and a long-chain alkyl group (Elastomer concentration: 16%).

The average structural formula (schematic drawing) of the organopolysiloxane elastomer obtained in Practical Example 1 is shown below.

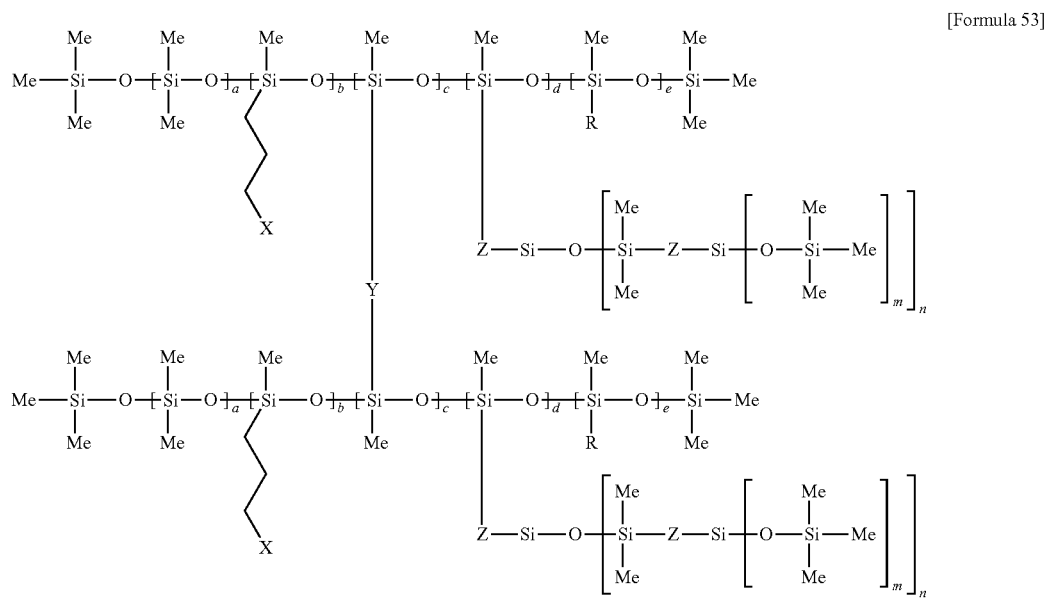

[Formula 53]

(in the formula, Me=methyl group, Z inside [ ]n=—$CH_2CH_2$—, Z outside [ ]n=—$C_3H_6$—COO—$C_3H_6$—, R=—$C_{16}H_{33}$, Y=—$C_6H_{12}$—, X=$(C_3H_6O_2)_2$H, a=43.2, b=1.84, c=2.86, d=0.1, e=3.1, m=3, and n=3)

Practical Example 2

Production of Silicone Compound No. 2

A reaction vessel was loaded with 74.3 g of methylhydrogenpolysiloxane represented by the average composition formula: $MD_{43.4}D^H{}_{7.4}M$, 2.6 g of 3-methacryloxypropyl(tris(trimethylsiloxy) silylethyl dimethylsiloxy) silane represented by the following average composition formula:

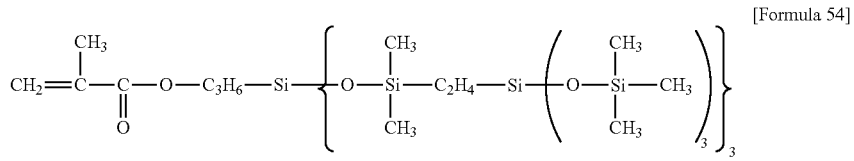

[Formula 54]

and 20.6 g of hexadecene (α-oefin purity 91.7%), which was then heated to 20° C. while stirring under a nitrogen flow. 0.10 mL of a hexamethyldisiloxane solution of platinum-1,3-divinyl-1,1,3,3-tetramethyldisiloxane complex (Pt concentration 0.45 wt. %) were then added, at which time the temperature was raised to 48° C. by the exothermic heat generated. This mixture was then heated to 50 to 60° C. and reacted for 1 hour. When a small quantity of the reaction liquid was sampled and the reaction rate was calculated by the alkali decomposition gas generation method, it was found that a modified silicone intermediate represented by $MD_{43.4}D^{R*31}_{0.1}D^{R*11}_{4.7}D^{H}_{2.6}M$ had been produced. Here, $R^{*11}$ and $R^{*31}$ are as described below. $R^{*11}$=—$C_{16}H_{33}$

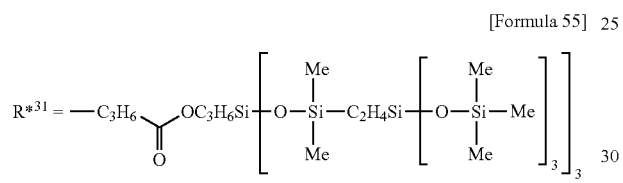

[Formula 55]

At this point, 100 g of caprylyl methicone, which is both a diluent and crosslinking reaction solvent, were introduced and the reaction liquid was mixed, and then 2.44 g of 1,5-hexadiene and 0.15 mL of the platinum catalyst were added at a temperature of 40 to 50° C., and when stirring was continued at 40 to 50° C., elastomerization occurred after 2 hours and the reaction mixture changed to a clear and soft greasy mass. The Vi/H mole ratio upon crosslinking here was 1.2. The reaction was continued for another 2 hours in this state to promote crosslinking, immediately after which, the reaction system was heated to 40 to 70° C. under reduced pressure and the low-boiling components were distilled out.

The composition was then removed from the reaction vessel and loaded into a high-shear mixer at a ratio of 199 g of caprylyl methicone to 199 g of the composition, and subjected for 30 minutes to shearing and pulverizing treatment, whereby 385 g of a homogenous paste-like composition was obtained containing a novel organopolysiloxane elastomer that had been modified with a siloxane dendron structure and a long-chain alkyl group, and which had absolutely no sense of foreign objects when touched (Elastomer concentration: 25%).

Practical Example 3

Production of Silicone Compound No. 3

A reaction vessel was loaded with 91.9 g of methylhydrogen polysiloxane represented by the average composition formula: $MD_{46.1}D^{H}_{3.15}M$ and 5.1 g of vinyl tris-trimethylsiloxysilane represented by the average composition formula: $CH_2$=CH—$Si(OSiMe_3)_3$, which was then heated to 70° C. while stirring under a nitrogen flow. 0.70 mL of a hexamethyl disiloxane solution of platinum-1,3-divinyl-1,1,3,3-tetramethyldisiloxane complex (Pt concentration: 0.45 wt. %) were then added and reacted for 5 hours at 70 to 80° C. When a small quantity of the reaction liquid was sampled and the reaction rate was calculated by the alkali decomposition gas generation method, it was found that a modified silicone intermediate represented by $MD_{46.1}D^{R*32}_{0.38}D^{H}_{2.77}M$ had been produced. Here, $R^{*32}$ has the below described meaning.

$R^{*32}$=—$C_2H_4$—$Si(OSiMe_3)_3$

At this point, 99 g of caprylyl methicone, which is both a diluent and crosslinking reaction solvent, were introduced and the reaction liquid was mixed, and then when 3.50 g of 1,5-hexadiene were added at a temperature of 40 to 50° C., and stirring was continued, elastomerization occurred after 50 minutes and the reaction mixture changed to a clear and soft greasy mass. The Vi/H mole ratio upon crosslinking here was 1.27. As a result of continuing the reaction for another 5.5 hours in this state to promote crosslinking, hardness increased, yielding a disintegratable grease-and-powder mass with a dry feel. Immediately thereafter, the product was heated to 40 to 70° C. under reduced pressure, and the low-boiling components were distilled out.

The composition was then removed from the reaction vessel and loaded into a high-shear mixer at a ratio of 198 g of caprylyl methicone to 198 g of the composition, and subjected for 30 minutes to shearing and pulverizing treatment, whereby 386 g of a homogenous paste-like composition was obtained containing a novel organopolysiloxane elastomer that had been modified with a siloxane dendron structure, and which had absolutely no sense of foreign objects when touched (Elastomer concentration: 25%).

Comparative Example 1

Production of Silicone Compound No. RE-1

A reactor was loaded with 110.1 g of methylhydrogenpolysiloxane represented by the average composition formula $MD_{40}D^{H}_{15}M$ and 12.1 g of 1-dodecene (corresponding to ¼ of the total charge quantity of 1-dodecene), which was then heated to 50° C. while being stirred under a nitrogen flow, and then 0.10 g of an ethanol solution of chloroplatinic acid were added (Pt concentration: 3 wt. %). The heat of reaction caused a temperature increase to 80° C., and then after confirming that the temperature had naturally dropped, 12.1 g of 1-dodecene were added a second time and reacted. 1-dodecene was further added and reacted a third and fourth time by the same method. Subsequently, after the mixture was reacted for 1 hour at 90 to 100° C., a small amount of the reaction liquid was sampled and it was confirmed by the alkali decomposition gas generation method that the target reaction rate had been achieved. The mixture was then heated under reduced pressure and low-boiling components, e.g., unreacted dodecene or the like, were removed.

Thereafter, 25.4 g of vinylmethylpolysiloxane represented by the average composition formula $^{Vi}MD_6M$ and 0.10 g of the platinum catalyst were added to the reaction mixture and reacted for 2 hours at 90 to 100° C., after which, it was confirmed by the same method that the target reaction rate had been reached. As a result of calculating the reaction rate, it was found that a modified silicone intermediate represented by the average composition formula $MD_{40}D^{R*41}_{15}D^{R*12}_{10}D^{H}_{3.5}M$ had been produced. Here, $R^{*12}$ and $R^{*41}$ are as described below.

$R^{*12}$=—$C_{12}H_{25}$ $R^{*41}$=—$C_2H_4SiMe_2(OSiMe_2)_6OSiMe_3$

At this point, 46.4 g of bis-allylpolyether represented by the average composition formula: $CH_2$=CH—$CH_2$—$(OCH_2CH_2)_{15}$—O—$CH_2$—CH=$CH_2$, 0.025 g of natural vitamin E, 138 g of toluene, and 0.10 g of the platinum catalyst were added and reacted for 2 hours at 90° C., whereupon elastomerization occurred and the reaction mixture changed into a soft and sticky rice cake-like or jam-like form that seemed semi-transparent. The Vi/H mole ratio upon crosslinking here was 1.2. As a result of continuing the reaction for another 2 hours in this state to promote crosslinking, hardness increased, yielding a disintegratable grease-like material with a dry feel. The material was then heated under reduced pressure to remove the toluene.

Next, 25.3 g of a 2% aqueous solution of citric acid was added, and treatment was performed for 2 hours at 80° C., after which, 2% sodium bicarbonate water was added and neutralization treatment was carried out for 1 hour. Heating under reduced pressure to distill out the low-boiling components yielded an organopolysiloxane elastomer modified by a group having a polyether group/C12 alkyl group/linear polysiloxane structure. The elastomer subsequently was transferred to a Hobart mixer and kneading and pulverization treatment was performed for 3 hours to yield a homogenous, white greasy composition. The mixture was then kneaded while gradually introducing 680 g of isododecane as a diluent over 3 hours to yield a semitransparent to white, soft, paste-like composition (elastomer concentration: 25%).

Comparative Example 2

Production of Silicone Compound No. RE-2

A reaction vessel was loaded with 125.3 g of methylhydrogenpolysiloxane represented by the average composition formula $MD_{40}D^H{}_{15}M$ and 13.7 g of 1-dodecene (corresponding to ¼ of the total charge quantity of 1-dodecene), which was heated to 50° C. while stirring under a nitrogen flow, and then 0.10 g of an ethanol solution of chloroplatinic acid were added (Pt concentration: 3%). The heat of reaction caused temperature increase to 85° C., and then after confirming that the temperature had naturally dropped, 13.7 g of 1-dodecene were added a second time and reacted. 1-dodecene was further added and reacted a third and fourth time by the same method. Subsequently, after the mixture was reacted for 1 hour at 90 to 100° C., a small amount of the reaction liquid was sampled and it was confirmed by the alkali decomposition gas generation method that the target reaction rate had been achieved. Thereafter, the mixture was heated under reduced pressure to remove the low-boiling components, e.g., unreacted dodecene or the like.

Thereafter, 28.9 g of vinylmethylpolysiloxane represented by the average composition formula $^{Vi}MD_6M$ and 0.10 g of the platinum catalyst were added to the reaction mixture and reacted for 2 hours at 90 to 100° C., after which, it was confirmed by the same method that the target reaction rate had been reached. As a result of calculating the reaction rate, it was found that a modified silicone intermediate represented by the average composition formula $MD_{40}D^{R*41}{}_{1.5}D^{R*12}{}_{10}D^H{}_{3.5}M$ had been produced. Here, $R^{*12}$ and $R^{*41}$ have the same meanings as indicated above.

At this point, 20.9 g of bis-allyl triglycerin represented by the average composition formula $CH_2$=CH—$CH_2$O—$(C_3H_6O_2)_3$—$CH_2$—CH=$CH_2$, 0.025 g of natural vitamin E, 138 g of toluene, and 0.10 g of the platinum catalyst were added and reacted for 2 hours at 80° C., whereupon, elastomerization occurred and the reaction mixture changed into a soft and sticky rice cake-like or jam-like form that seemed semi-transparent. The Vi/H mole ratio upon crosslinking here was 1.2. As a result of continuing the reaction for another 2 hours in this state to promote crosslinking, hardness increased, yielding a disintegratable grease-like material with a dry feel. The material was then heated under reduced pressure to remove the toluene.

Next, 25.3 g of a 2% aqueous solution of citric acid was added, and treatment was performed for 2 hours at 80° C., after which, 2% sodium bicarbonate water was added and neutralization treatment was carried out for 1 hour. Heating under reduced pressure to distill out the low-boiling components yielded an organopolysiloxane elastomer modified by a group having a triglycerin group/C12 alkyl group/linear polysiloxane structure. The elastomer subsequently was transferred to a Hobart mixer and kneading and pulverization treatment was performed for 3 hours to yield a homogenous, white greasy composition. The mixture was then kneaded while gradually introducing 680 g of isododecane as a diluent over 3 hours to yield a semitransparent to white, soft, paste-like composition (elastomer concentration: 25%).

Practical Example 4, Comparative Examples 3 and 4

The sensation during use (sensation during use in a non-aqueous system) was assessed for mixtures (dispersions) of isododecane and the paste-like compositions obtained in practical example 1 and comparative examples 1 and 2 according to the following procedures and assessment criteria. The results are shown in Table 2. In the table, "parts" indicates "parts by weight (mass)."

[Functionality Assessment (Sensation During Use) Method]

1. A transfer pipette was used to collect 0.10 g of the mixture, which was placed on the back of the hand and spread with the fingers.
2. At this time, the tactile sensation was assessed at initial application and once applied, and skin impression and the skin feel after drying (15 minutes after application) were assessed.
3. Retention of the excellent feel characteristic of elastomers was judged based on the above results.

[Functionality Assessment Criteria: Oil Agent=Isododecane]

"Tactile Sensation: At Initial Application and Once Applied"
◎: Velvety and thick like an elastomer, good slipping smoothness, spread smoothly. ○: Excellent slip and spreadability, but felt a little sticky and lacked some of the characteristic thick elastomer feel.
Δ: Good slip and spreadability, but has virtually none of the characteristic thick elastomer feel.
x: Insufficient slip feel, spread has a heavy and oily feel. Also has none of the characteristic thick elastomer feel.
"Skin Impression: Once Applied"
○: Blended well into skin, minimally oily, matte feel gives a natural impression on the skin.
Δ: Neither good nor bad. Minimal shiny luster.
x: Intense and persistent oily shine (luster).
"Skin Feel after Application: After Drying"
◎: Retains good characteristic elastomer smoothness, with absolutely no sticky feeling.
○: Has characteristic elastomer thick smoothness, but with a somewhat resistant feel.
Δ: Retains slip, but without any of the characteristic thick elastomer feel, and gave a slightly sticky feel.
x: Intensely sticky, with absolutely no slip feel.
"Tactile Sensation Retention"
○: Retains characteristic elastomer thick smoothness with virtually no change from when initially applied, once applied, and even after drying.
Δ: Tactile sensation changes over the period from initial application, once applied, and after drying, but with minimal unpleasant feel. Or, tactile sensation doesn't reach an unpleasant level.

x: Tactile sensation deteriorates significantly over the period from initial application, once applied, and further after drying.

TABLE 2

Formulations and Assessment Results for Mixtures (Dispersions) with Isododecane (Practical Example 4, Comparative Examples 3 and 4)

| Raw Material | Practical Example 4 | Comparative Examples 3 | Comparative Examples 4 |
|---|---|---|---|
| Practical Example 1 paste-like composition (elastomer concentration: 16%) | 50 | — | — |
| Comparative Example 1 paste-like composition (elastomer concentration: 25%) | — | 32 | — |
| Comparative Example 2 paste-like composition (elastomer concentration: 25%) | — | — | 32 |
| Isododecane | 50 | 68 | 68 |
| Elastomer Concentration (%) | 8 | 8 | 8 |
| Tactile Sensation: Initial application to once applied | ◎ | ○ | ○ |
| Skin Impression: Once applied | ○ | X | X |
| After skin application feel: After drying | ◎ | X | X |
| Tactile Sensation Retention | ○ | X | X |

Practical Example 5, Comparative Examples 5 and 6

The sensation during use (sensation during use in a non-aqueous system) was assessed for mixtures (dispersions) of mineral oil and the paste-like compositions obtained in practical example 1 and comparative examples 1 and 2 according to the following procedures and assessment criteria. The results are shown in Table 3. In the table, "parts" indicates "parts by weight (mass)".

[Functionality Assessment (Sensation During Use) Method]
1. A transfer pipette was used to collect 0.10 g of the mixture, which was placed on the back of the hand and spread with the fingers.
2. At this time, the tactile sensation was assessed at initial application and once applied, and skin impression and the skin feel after drying (15 minutes after application) were assessed.
3. Retention of the excellent feel characteristic of elastomers was judged based on the above results.

[Functionality Assessment Criteria: Oil Agent=Mineral Oil]

"Tactile Sensation: At Initial Application and Once Applied"
◎: Pleasant slip feel characteristic of an elastomer powder, light and good spread. Moreover, this sensation persists
○: Thick slip feel characteristic of elastomers, but felt a little sticky.
x: Normal slip feel, with virtually none of the characteristic elastomer feel, and with an oily feel.

"Skin Impression: Once Applied"
◎: Blends well into skin, minimal oily feel. Minimal oily shine.
Δ: Neither good nor bad. Moderate oily shine.
x: Intense and persistent oily shine (luster).

"Skin Feel after Application: After Drying"
◎: Retains pleasant characteristic elastomer slip feel without any change, and with absolutely no sticky feeling.
○: Has characteristic elastomer thick slip feel, but with a somewhat resistant feel.
Δ: Produces sticky feel, and gives a clearly resistant feel with decreased slipperiness.
x: Intensely sticky, with absolutely no slip feel.

"Tactile Sensation Retention"
◎: Retains pleasant characteristic elastomer slip feel with absolutely no change from when initially applied, once applied, and even after drying.
Δ: Tactile sensation changes over the period from initial application, once applied, and after drying, but with minimal unpleasant feel. Or, tactile sensation doesn't reach an unpleasant level.
x: Tactile sensation deteriorates significantly over the period from initial application, once applied, and further after drying.

TABLE 3

Formulations and Assessment Results for Mixtures (Dispersions) with Mineral Oil (Practical Example 5, Comparative Examples 5 and 6)

| Raw Material | Practical Example 5 | Comparative Examples 5 | Comparative Examples 6 |
|---|---|---|---|
| Practical Example 1 paste-like composition (elastomer concentration: 16%) | 50 | — | — |
| Comparative Example 1 paste-like composition (elastomer concentration: 25%) | — | 32 | — |
| Comparative Example 2 paste-like composition (elastomer concentration: 25%) | — | — | 32 |
| Mineral oil 50SUS (37.8° C.) | 50 | 68 | 68 |
| Elastomer Concentration (%) | 8 | 8 | 8 |
| Tactile Sensation: Initial application and once applied | ◎ | ○ | ○ |
| Skin Impression: Once applied | ○ | Δ | Δ |
| Skin Feel After Application: After drying | ◎ | Δ | Δ |
| Tactile Sensation Retention | ◎ | X | X |

The purpose of testing practical examples 4 and 5 and comparative examples 3 to 6 was to know whether adding the organopolysiloxane elastomer of the present invention to an organic oil with inferior tactile sensation compared to silicone oil would dramatically improve the tactile sensation in a non-aqueous system primarily consisting of an organic oil, and to what extent compared with comparative products, how the addition would improve the skin feel, etc. after application, and how these effects would be retained. Namely, since the products of the present invention and the comparative products both were elastomers having silicone as the main backbone, they naturally had a good affinity with silicone oils, and it was unlikely that differences would appear in the effects thereof, even when tested in systems used in combination with silicone oils with good tactile feel. Therefore, differences in the effects were checked in mixed systems with non-silicone oils, in which it was thought that the differences in tactile sensation due to the elastomer would be easily presented.

It was shown, as described above, that the organopolysiloxane elastomer of the present invention (the type including a hydrophilic group) had excellent affinity with a variety of organic oils and not only with silicone oils, and surprisingly retained the thick, smooth, and somewhat powdery initial usage feel characteristic of elastomers not only when initially applied, but also after application and further after drying, without virtually any change. This kind of performance was a feature of the products of the present invention that was not achieved by conventional hydrophilic silicone elastomers, which was also apparent upon reviewing the results of the comparative examples 3 to 6. Moreover, mixtures of the product of the present invention and oil agents provided a consistent natural skin feel with minimal shininess from initial application to after drying. This aspect also contrasted with the silicone elastomers of the comparative examples (which, despite being an elastomer, had a substantial oily shine and gave the skin an oily sheen). Isododecane is a typical volatile oil agent and, while it is rare that the volatility of such oils has virtually no effect on (does not adversely affect) the sensation during use of formulations to which it has been admixed, the results of utilizing the product of this invention showed that it was possible to dramatically increase the degree of freedom in formulating cosmetics and external use preparations, and the convenience when designing formulations.

Practical Examples 6 to 9 and Comparative Examples 7 to 14

Water-in-oil emulsion compositions of the compositions shown in Tables 4 and 5 were prepared by the following procedures, using the paste-like compositions obtained in practical example 1 and comparative examples 1 and 2, and the viscosities thereof were measured. Furthermore, the functionality (tactile sensation, sensation during use), standing stability (appearance and form), stability under stress, stability of emulsified particle size, and odor production over time were assessed according to the following assessment criteria. The results are shown in Tables 4 and 5. In the table, "parts" indicates "parts by weight (mass)".

[Preparation Method for Water-in-Oil Emulsion Composition]
1. A 200 mL vessel was loaded with an oil agent and a paste-like composition, as a surfactant (emulsifier).
2. Stirring was performed to uniformly disperse the paste-like composition in the oil agent (oil phase or powder-in-oil dispersion phase A).
3. Another vessel was loaded with sodium chloride and ion exchanged water and dissolved by mixing with a spatula. Furthermore, 1,3-butylene glycol was mixed and dissolved therein (aqueous phase B).
4. After immersing the blades of a homo-disper in the oil phase A and securing the vessel, the aqueous phase B was poured into the oil phase A at nearly a constant rate over approximately 45 seconds while stirring at 1,000 rpm.
5. The rotation speed of the homo-disper was increased to 3,500 rpm, and mixing was continued for 2 minutes until the overall mixture became homogenous.
6. Stirring was stopped, the oil component and the like attached to the inner wall of the container was scraped down, and admixed to the resulting emulsion.
7. Mixing was carried out for 3 minutes at a homo-disper speed of 3,500 rpm to homogenize the entire mixture.

[Emulsion Viscosity and Properties]
1. The properties of the water-in-oil emulsion composition resulting from the above method were recorded.
2. The viscosity of this emulsion composition at 25° C. was measured using an E-type viscometer. Measurement was conducted at this time with the cone rotor speed of the viscometer set to 0.5 rpm.

[Functionality Assessment (Tactile Sensation and Sensation During Use)]
The sensation during use at initial application, during application and once applied, and the skin feel after drying were assessed for the water-in-oil emulsion compositions when used as cosmetics. Since 2 cs and mineral oil were the only oil agents that could be completely emulsified with all of the paste-like compositions of the practical examples and comparative examples, functionality assessments were conducted only for these formulations. Since the spreadability, simple acceptability of slipperiness, soft feel, and wrinkle concealing effect were at excellent levels for all the samples, assessments were performed focusing on the following aspects. Specifically:

1. 0.10 g of the water-in-oil emulsion composition was placed on a finger and spread on the back of the hand.
2. At this time, the watery feel and thick slipperiness and powdery feel characteristic of elastomers at initial application, during application, once applied, and after drying, as well as imparting a moisturizing feel after application and minimal sense of stickiness during drying, and the like were assessed according to the following criteria.

"Tactile Sensation: At Initial Application and During Application"
⊚: Yields a watery feel, and retains characteristic thick smoothness. Balance with oils is also good.
○: Initially, yields very watery feel, but also has a slightly thick and slimy slippery feel.
Δ: Yields a watery feel, but does not have much of a smooth or thick feel.
x: Feels somewhat thick and smooth, but otherwise has almost none of the watery application feel, and has a feel of a normal cream.

"Moisturizing Feel and Skin Feel: Once Applied"
⊚: Blends well into the skin, yields a good moisturizing feel, and has a great balance between oils and water content on the skin. Yields a sensuous appearance and natural skin feel, without noticeable shine.
○: Good moisturizing feel, but slightly oily shine can be seen.
Δ: Doesn't really have a moisturizing feel, but has an excellent matte, natural skin feel.
x: No moisturizing feel, intensely oily, slimy, and shiny.

"Skin Feel after Application: After Drying"
⊚: Has a powdery feel, with good retention of velvety feel with no change in the characteristic thick smoothness, and producing absolutely no sticky feel.
Δ: Velvety thick smoothness remains to some extent, but slipperiness decreased and resistant feel increased.
x: Intense sticky feel and absolutely no slippery feel. Or intensely oily slimy feel.

"Tactile Sensation Retention"
⊚: Retains pleasant characteristic elastomer feel with almost no change from when initially applied, once applied, and even after drying.
Δ: Tactile sensation changes over the period from initial application, once applied, and after drying, but with minimal unpleasant feel. Or, tactile sensation doesn't reach an unpleasant level.
x: Tactile sensation deteriorates significantly over the period from initial application, once applied, and further after drying.

[Emulsion Standing Stability: Appearance and Form]
For each of the water-in-oil emulsion compositions on the date of preparation, and also for each emulsion composition after being set aside for 1 month at 50° C. (28 g measured out into a 35 mL glass container and then tightly stoppered), visual appearance and form were observed. These were evaluated by the below described criteria.
⊚: Has an entirely uniform matte cream or gel form, even after the passage of time.
○: Has a mostly uniform matte cream or gel form, even after the passage of time. There may be a slight quantity of precipitate.
Δ: After the passage of time, roughness is readily visible on the surface of the emulsion, which is irregular, and has a fairly large quantity of precipitate
x: The emulsion itself was initially incomplete, and phase separation occurred.

[Emulsion Stability Under Stress]
⊚: When the cream is taken up by the fingers and applied to the back of the hand, even when the cream is pressed against the skin somewhat strongly, there is no generation whatsoever of water droplets.
Δ: When cream is taken up by the fingers and simply placed on the back of the hand, although water droplets are not generated, water droplets are somewhat generated while the cream is being spread by the fingers.

x: The cream breaks down simply by being taken up by the fingers, and water droplets are generated. When the cream is coated on the back of the hand simply by lightly spreading the cream using the fingers, large droplets suddenly appear (emulsion breaks down immediately).

[Measurement of Emulsified Particle Size and Stability Assessment]

For each of the water-in-oil emulsion compositions on the day after preparation, and for each emulsion composition after being set aside for 1 month at 50° C. (in the aforementioned manner, 28 g weighed out into a glass container and tightly stoppered), the range of distribution of particle diameter was visually determined by optical microscope observation (1,000×) and photographic imaging. Thereby, stability was evaluated by examining the initial emulsified particle size and the emulsified particle size over time.

Note that notes were made in the tables when particle coalescence was observed.

◎: There is a little change in emulsified particle size, and signs of coalescence are absent.

○: It is possible that the emulsified particle size increased somewhat, but no clear coalescence is observed. Alternatively, the emulsified particle size increased, but the overall particle size is small and the emulsion system was maintained.

Δ: Some particle coalescence is suspected, and emulsion particle size has clearly increased.

x: Many particles are coalesced and emulsion is in the state of breaking down. Alternatively, there was severe coalescence from the start.

[Assessment of Odor Emission by Emulsion Over Time]

Each water-in-oil emulsion composition (as described above, 28 g were weighed out into a 35 mL glass container and then tightly stoppered) left to stand for one month at 50° C., and then removed and returned to room temperature. The bottles were opened on the next day, and the odor produced was evaluated in accordance with the following criteria. Note that relative comparisons were carried out within groups that used a common oil agent.

◎: Level with practically no noticeable odor.
○: Slight odor (unique, sweet solvent-like odor) is perceived.
Δ: Moderate odor (unique, sweet solvent-like odor) is perceived.
x: Strong odor (unique, sweet solvent-like odor) is perceived.

TABLE 4

Formulations and Assessment Results for Water-in-Oil Emulsion Compositions
(Practical Examples 6 and 7, Comparative Examples 7 to 10)

| Raw Materials | Practical Examples 6 | 7 | Comparative Examples 7 | 8 | 9 | 10 |
|---|---|---|---|---|---|---|
| Practical Example 1 paste-like composition (elastomer concentration: 16%) | 12.5 | 12.5 | — | — | — | — |
| Comparative Example 1 paste-like composition (elastomer concentration: 25%) | — | — | 8 | 8 | — | — |
| Comparative Example 2 paste-like composition (elastomer concentration: 25%) | — | — | — | — | 8 | 8 |
| Dimethylpolysiloxane (2 cst) | 12.5 | — | 17 | — | 17 | — |
| Mineral oil 50SUS (37.8° C.) | — | 12.5 | — | 17 | — | 17 |
| Sodium chloride | 0.5 | 0.5 | 0.5 | 0.5 | 0.5 | 0.5 |
| Purified water | 68.5 | 68.5 | 68.5 | 68.5 | 68.5 | 68.5 |
| 1,3-butylene glycol | 6 | 6 | 6 | 6 | 6 | 6 |
| Emulsifier conc. (%) | 2 | 2 | 2 | 2 | 2 | 2 |
| Emulsion properties | Creamy to gel-like | Same as at left | Creamy to gel-like | Same as at left | Same as at left | Same as at left |
| Emulsion viscosity (mPas) | 12,000 | 55,000 | 103,000 | 135,000 | 107,000 | 155,000 |
| Feel: At initial application and during application | ◎ | ◎ | X | X | ○ | ○ |
| Moisturizing Feel and Skin Feel: Once applied | ◎ | ◎ | X | X | Δ | Δ |
| Skin Feel After Application: After drying | ◎ | ◎ | X | Δ | Δ | Δ |
| Tactile Sensation Retention | ◎ | ◎ | X | X | X | X |
| Emulsion Standing Stability | ◎ | ◎ | ◎ | ◎ | ◎ | ◎ |
| Emulsion Stress Stability | ◎ | ◎ | ◎ | ◎ | X | X |
| Initial particle Size Distribution (μm) | 3-8 | 2-7 | 1-5 | 2-7 | 3-13 coalesced | 4-40 coalesced |
| Particle Size Distribution After Time Has Passed (μm) | 3-8 | 2-8 | 1-6 | 2-8 | 3-20 coalesced | 5-40 coalesced |
| Emulsified Particle Stability | ◎ | ◎ | ◎ | ◎ | X | X |
| Emulsion Odor Over Time | ○ | ○ | ○ | ○ | ○ | ○ |

TABLE 5

Formulations and Assessment Results for Water-in-Oil Emulsion Compositions
(Practical Examples 8 and 9, Comparative Examples 11 to 14)

| Name of raw material | Examples | | Comparative Examples | | | |
|---|---|---|---|---|---|---|
| | 8 | 9 | 11 | 12 | 13 | 14 |
| Practical Example 1 paste-like composition (elastomer concentration: 16%) | 12.5 | 12.5 | — | — | — | — |
| Comparative Example 1 paste-like composition (elastomer concentration: 25%) | — | — | 8 | 8 | — | — |
| Comparative Example 2 paste-like composition (elastomer concentration: 25%) | — | — | — | — | 8 | 8 |
| Isododecane | 12.5 | — | 17 | — | 17 | — |
| Caprylyl methicone | — | 12.5 | — | 17 | — | 17 |
| Sodium chloride | 0.5 | 0.5 | 0.5 | 0.5 | 0.5 | 0.5 |
| Purified water | 68.5 | 68.5 | 68.5 | 68.5 | 68.5 | 68.5 |
| 1,3-butylene glycol | 6 | 6 | 6 | 6 | 6 | 6 |
| Emulsifier conc. (%) | 2 | 2 | 2 | 2 | 2 | 2 |
| Properties of emulsion | Creamy to gel-like | Same as at left | Creamy to gel-like | Same as at left | Separated | Separated |
| Emulsion Viscosity (mPas) | 9,800 | 14,000 | 67,000 | 111,000 | — | — |
| Emulsion Standing Stability | ◎ | ◎ | ◎ | ◎ | X | X |
| Emulsion Stress Stability | ◎ | ◎ | ◎ | ◎ | X | X |
| Initial Particle Size Distribution (μm) | 3-13 | 3-8 | 2-9 | 2-6 | — | — |
| Particle Size Distribution After Time Has Passed (μm) | 2-14 | 2-8 | 2-10 | 2-7 | — | — |
| Emulsified Particle Stability | ◎ | ◎ | ◎ | ◎ | X | X |
| Emulsion Odor Over Time | ◎ | ○ | ◎ | ○ | — | — |

The above has made it clear that the organopolysiloxane elastomer of the present invention (type including a hydrophilic group), despite being a silicone elastomer that includes absolutely no polyether groups, exhibits excellent affinity with a variety of organic oils and not only with silicone oils in water-in-oil emulsions containing water, and provides an emulsion of excellent stability in a wide range of types of oil agents The fact that this completely was not achieved by the polyglycerin-modified silicone elastomer according to conventional technology (composition of comparative example 2) is apparent upon reviewing the results of comparative examples 9, 10, 13, and 14.

Furthermore, water-in-oil emulsions containing the organopolysiloxane elastomer of the present invention (type including a hydrophilic group) produced a watery feel when applied to the skin, and because they retained this feel, had an excellent moisturizing feel, while simultaneously also retaining a suitable level of oils, and were able to impart a consistent and natural skin feel with minimal shininess from initial application until after drying. This verifies the benefit that the performance-related features of the organopolysiloxane elastomer of the present invention can be advantageously retained in blended formulations. Additionally, it was confirmed that water-in-oil emulsions containing the organopolysiloxane elastomer of the present invention (type including a hydrophilic group) retain the characteristic thick and smooth, and slightly powdery initial usage feel of elastomers, virtually without change, not only at initial application, but surprisingly also until after dried. This type of performance is one feature of the product of the present invention that is not achieved by conventional hydrophilic silicone elastomers, which is made clear by comparisons of practical examples 6 and 7 versus comparative examples 7 and 8. Furthermore, it was confirmed that the water-in-oil emulsion composition of the present invention has retention of excellent moisturizing effect. Consequently, by using this in external use preparations and cosmetics, transdermal moisture loss can be effectively suppressed, whereby the effects of providing protection and nutrition to the skin can be expected.

However, the greatest discovery and achievement of the present invention is the fact that the organopolysiloxane elastomer of the present invention (type including a hydrophilic group), which is also a hydrophilic polymer, surfactant, and emulsifier, demonstrated all of the aforementioned excellent effects while also manifesting hard to believe performance without imparting absolutely any sticky feeling for the time from when the emulsion is applied until it dries, or even after it has dried. While it is uncertain why the present invention is able to resolve several such tradeoffs all at once, the fact that, regardless of having an immobile cream to gel-like physical form, a water-in-oil emulsion composition of the present invention has a soft tactile sensation and exhibits substantially lower measured viscosity than water-in-oil emulsion compositions obtained from comparative products manifesting the same physical form, is considered to reflect the completely lack of stickiness that is a feature of the product of the present invention. In addition to this, the excellent stability of emulsions obtained from the product of the present invention is a discovery that defies conventional wisdom, and not only dramatically increases the degree of freedom in formulation and the convenience when designing formulations for cosmetics and external use preparations using the product of the present invention, but also can achieve substantially improved performance and efficacy in the cosmetics and external use preparations. Therefore, the present invention makes a very considerable social contribution.

Practical Example 10, Comparative Examples 15 and 16

Mixtures of oil agents and paste-like compositions obtained in practical example 1 and comparative examples 1 and 2 were prepared according to the following procedures, and according to the compositions in Table 5 (elastomer concentration: 16%). The viscosities of the resulting compositions were also measured, and the oil thickening, gelling, and structuring effects of the organopolysiloxane elastomer of the present invention were confirmed. The results are shown in Table 5. In the table, "parts" indicates "parts by weight (mass)".

[Preparation Method for Mixtures with Oil Agents]
1. A Hobart mixer was loaded with the paste-like composition, and the oil agent was introduced by dripping over 5 minutes while mixing to yield a uniform composition (powder-in-oil dispersion).
2. The viscosity of this mixture at 25° C. was measured using an E-type viscometer. The physical properties were also recorded. Viscosity was measured at this time while changing the cone rotor speed of the viscometer set between the two settings of 10 rpm and 0.5 rpm.
3. The thixotropy index TI of the dispersion was calculated by the following equation.

TI=Measured viscosity at 0.5 rpm/Measured viscosity at 10 rpm

TABLE 6

Formulations and Assessment Results for Mixtures (Dispersions) with Oil Agents (Practical Example 10, Comparative Examples 15 and 16)

|  | Practical Example | Comparative Examples | |
|---|---|---|---|
| Raw Materials | 10 | 15 | 16 |
| Practical Example 1 paste-like composition (elastomer concentration: 16%) | 100 | — | — |
| Comparative Example 1 paste-like composition (elastomer concentration: 25%) | — | 64 | — |
| Comparative Example 2 paste-like composition (elastomer concentration: 25%) | — | — | 64 |
| Oil agent = caprylyl methicone | 0 | 36 | 36 |
| Elastomer Concentration (%) | 16 | 16 | 16 |
| Dispersion Viscosity (10 rpm) [mPa · s] | 3200 | 600 | 710 |
| Dispersion Viscosity (0.5 rpm) [mPa · s] | 10600 | 900 | 1100 |
| Dispersion Thixotropy Index | 3.3 | 1.5 | 1.5 |
| Dispersion Physical Form | Paste | Liquid | Liquid |

It was understood from the above that when the organopolysiloxane elastomer of the present invention (type including a hydrophilic group) and a hydrophilic silicone elastomer according to conventional technology were compared at identical concentrations, the former was clearly superior in oil agent thickening performance, gelling performance, and constructing performance. It was also confirmed that the product of the present invention had the effect of providing greater thixotropy to oil agents. In contrast, the latter two comparative products had problems on the aspects of thickening, gelling, and structuring efficiency, requiring the compounding of large quantities of elastomer to manifest clear effects as oil structuring agents.

The organopolysiloxane elastomer of the present invention (type not including a hydrophilic group) will be explained below. Typically constituted from only a lipophilic group or hydrophobic group, this organopolysiloxane elastomer is a type of non-emulsifiable silicone elastomer with no surface activity or emulsifying capability. However, since a characteristic of the organopolysiloxane elastomer of the present invention (type not including a hydrophilic group) is that it includes a siloxane dendron structure, the organopolysiloxane elastomer of the present invention has superior slipperiness compared with non-emulsifiable silicone elastomers of conventional technology, while having characteristic elastomer tactile feel, and can impart even less stickiness to no stickiness to cosmetics and external use preparations. Consequently, the organopolysiloxane elastomer of the present invention (type not including a hydrophilic group) can be used in the similar applications to conventional non-emulsifiable crosslinking organopolysiloxanes, and can provide a better sensation during use.

By combining the organopolysiloxane elastomer of the present invention (type not including a hydrophilic group) with a co-modified organopolysiloxane having a siloxane dendron structure reported in International Unexamined Patent Application No. 2011/049248 that has a monoglycerin derivative as a hydrophilic group, and blending this mixture into a water-in-oil emulsion composition, the organopolysiloxane elastomer of the present invention (type not including a hydrophilic group) can be made to exhibit characteristic properties of the paste-like composition obtained in comparative example 2 more easily and at lower cost. Although the silicone elastomer of comparative example 2 cannot stand alone as an emulsifier, as already discussed, it is known that it has unique efficacy as a temporary tactile sensation improver for water-in-oil emulsions.

Explained more specifically, since emulsions obtained using the silicone elastomer of comparative example 2 are extremely weak under stress, the emulsion has the quality of instantaneously breaking down and producing large water droplets when applied to the skin, whereby, albeit temporary, a very watery tactile sensation is obtained. It was thought that there was no other technique whereby this quality and the thick, smooth sensation during use that is characteristic of elastomers could both be realized, but it was shown that the same effect could be realized at lower cost by the present invention This will be explained below, using practical examples.

Practical Examples 11 and 12, Comparative Example 9

Water-in-oil emulsion compositions were prepared of the compositions shown in Table 6 by the following procedure, using the paste-like compositions obtained in practical examples 2 and 3 and comparative example 2, and the functionality (tactile sensation, sensation during use) thereof was assessed according to the following assessment criteria. The results are shown in Table 6. In the table, "parts" indicates "parts by weight (mass)".

[Preparation Method for Water-in-Oil Emulsion Composition]
1. A 200 mL vessel was loaded with an oil agent, surfactant (emulsifier), and paste-like composition. Furthermore, the paste-like composition of comparative example 2 serves as a surfactant.
2. Stirring was performed to uniformly disperse the paste-like composition into the oil agent (oil phase or powder-in-oil dispersion phase A).
3. Sodium chloride and ion exchanged water were placed in a separate container and dissolved by mixing using a spatula. Furthermore, 1,3-butylene glycol was mixed and dissolved therein (aqueous phase B).
4. After immersing the blades of a homo-disper in the oil phase A and securing the vessel, the aqueous phase B was poured into the oil phase A at nearly a constant rate over approximately 45 seconds while stirring at 1,000 rpm.
5. The rotation speed of the homo-disper was increased to 3,500 rpm, and mixing was continued for 2 minutes until the overall mixture became homogenous.
6. Stirring was stopped, the oil component and the like attached to the inner wall of the container was scraped down, and admixed to the resulting emulsion.
7. Mixing was carried out for 3 minutes at a homo-disper speed of 3,500 rpm to homogenize the entire mixture.

[Functionality Assessment (Tactile Sensation and Sensation During Use)]

The sensation during use at initial application, during application and once applied, and the skin feel after drying were assessed for the water-in-oil emulsion compositions when used as cosmetics. Since the spreadability, simple acceptability of slipperiness, soft feel, and wrinkle concealing effect were at excellent levels for all the samples, assessments were performed focusing particularly on a very watery feel at initial application (produced by the emulsion breaking down under stress), and the thick smoothness and powdery feel characteristic of elastomers at initial application and once applied. Specifically:

1. 0.10 g of the water-in-oil emulsion composition was placed on a finger and spread on the back of the hand.

2. At this time, the sensation during use at initial application, during application, once applied, and after drying, as well as imparting a moisturizing feel after application and minimal sense of stickiness during drying, and the like were assessed according to the following criteria.

[Tactile Sensation: Initial Application and During Application]

⊚: Yields a very watery feel, and retains characteristic elastomer thick smoothness.

○: Initially, yields very watery feel, but also has a slightly thick and slimy slippery feel.

Δ: Yields a watery feel, but does not have much of a smooth or thick feel.

x: Feels somewhat thick and smooth, but otherwise has almost none of the watery application feel, and has a feel of a normal cream.

"Moisturizing Feel and Skin Feel: Once Applied"

⊚: Blends well into the skin, yields a good moisturizing feel, and has a great balance between oils and water content on the skin. Yields a sensuous appearance and natural skin feel, without noticeable shine.

○: Slight moisturizing feel, matte with excellent natural skin feel.

Δ: Doesn't really have a moisturizing feel, but has an excellent matte, natural skin feel.

x: No moisturizing feel, intensely oily, slimy, and shiny.

"Skin Feel after Application: After Drying"

⊚: Has a powdery feel, with good retention of velvety feel with no change in the characteristic thick smoothness, and producing little sticky feel.

Δ: Velvety thick smoothness remains to some extent, but slipperiness decreased and resistant feel increased.

x: Intensely sticky, with absolutely no slip feel. Or intensely oily slimy feel.

"Tactile Sensation Retention"

⊚: Retains pleasant characteristic elastomer feel with almost no change from when initially applied, once applied, and even after drying.

Δ: Tactile sensation changed over the period from initial application, once applied, and after drying, but only an acceptable level.

x: Tactile sensation deteriorates significantly over the period from initial application, once applied, and further after drying.

TABLE 7

Formulations and evaluation results of the water-in-oil emulsion compositions (Practical Examples 11 to 12 and Comparative Example 9)

| Raw Materials | Practical Example 11 | Practical Example 12 | Comparative Example 9 |
|---|---|---|---|
| Practical Example 2 paste-like composition (elastomer concentration: 25%) | 8 | — | — |
| Practical Example 3 paste-like composition (elastomer concentration: 25%) | — | 8 | — |
| Monoglycerin derivative-modified silicone having a siloxane dendron structure *1) | 2 | 2 | — |
| Comparative Example 2 paste-like composition (elastomer concentration, 25%) | — | — | 8 |
| Dimethylpolysiloxane (2 cst) | 17 | 17 | 17 |
| Sodium chloride | 0.5 | 0.5 | 0.5 |
| Purified water | 68.5 | 68.5 | 68.5 |
| 1,3-butylene glycol | 6 | 6 | 6 |
| Emulsifier conc. (%) | 2 | 2 | 2 |
| Feel: At initial application and during application | ⊚ | ⊚ | ○ |
| Moisturizing Feel and Skin Feel: Once applied | ○ | ○ | Δ |
| Skin Feel After Application: After drying | ○ | ○ | Δ |
| Tactile Sensation Retention | Δ | ○ | X |

Note
1*) Glycerin-modified silicone having a siloxane dendron structure and an alkyl group shown in practical example 5 of International Unexamined Patent Application No. 2011/049248, and represented by the average composition formula $MD_{400}D^{R*13}{}_{2}D^{R*32}{}_{3}D^{R*22}{}_{5}M$.
In the formula, $R^{*13}$, $R^{*22}$, and $R^{*32}$ are as indicated below.
$R^{*13} = -C_{10}H_{21}$
$R^{*22} = -C_3H_6OCH_2CH(OH)CH_2OH$
$R^{*32} = -C_2H_4Si(OSiMe_3)_3$ Considering that the hydrophilic silicone elastomer of comparative example 2 cannot be a material positioned with the crucial responsibility of maintaining the stability and emulsion viscosity of an oil-and-water system, i.e., cannot adequately fill the role of an emulsifier, the production thereof requires the use of complex processes and reaction solvents and, moreover, necessitates the use of expensive polyglycerin derivatives as raw materials, and therefore has been a material with little appeal on the aspect of cost versus efficacy. On the other hand, the organopolysiloxane elastomers of the present invention (type not including a hydrophilic group) according to practical examples 2 and 3 do not require reaction solvents and have a relatively simple process. Additionally, the material described above that is a co-modified organopolysiloxane having a siloxane dendron structure reported in International Unexamined Patent Application No. 2011/049248 having a monoglycerin as a hydrophilic group can be produced in a one-pot process, and the glycerinmonoallyl ether that is a hydrophilic raw material is available relatively inexpensively, thus making production possible at vastly lower cost than elastomer type materials. According to the above, the novel combination of the two materials discovered here is an invention that more economically improves the sensation during use of compositions from water-in-oil emulsions to cosmetics, and the like, making a significant social contribution.

Furthermore, when the organopolysiloxane elastomer of the present invention (type not including a hydrophilic group), like those shown in practical examples 2 and 3 is employed as an oil phase structuring agent, and the novel liquid organopolysiloxane disclosed in Japanese Unexamined Patent Application No. 2011-286976 and/or the novel liquid organopolysiloxane disclosed in Japanese Unexamined Patent Application No. 2011-121095 is employed as an emulsifier, excellent efficacy can be demonstrated similar to when the organopolysiloxane elastomer of the present invention (type including a hydrophilic group) is used alone, as shown in practical example 1. The former is a means of delegating the two different roles of structuring and emulsifying to different materials, while the latter is a technique for fulfilling those two roles with a single material.

As shown above, the organopolysiloxane elastomer of the present invention is very useful as a gelling agent, structuring agent, thickener, tactile sensation improver, moisturizing agent, masking agent (wrinkle concealer), surfactant, emulsifier, film forming agent, and powder dispersion stabilizer, and the like, and the performance thereof surpasses that of conventional technology. The organopolysiloxane elastomer of the present invention (type including a hydrophilic group) does not necessarily have a polyether group in its structure and can stand alone as an emulsifier for water-in-oil emulsions, and moreover is a material that can provide the excellent sensation during use that is characteristic of elastomers. Consequently, the organopolysiloxane elastomer of the present invention that in particular has a structure that includes a glycerin derivative as a hydrophilic group and does not include a polyoxyethylene structure can be used to prepare water-in-oil emulsion cosmetics and the like having sufficient stability, without requiring the concomitant use of nonionic surfactants, such as other hydrophilic silicone emulsifiers having a PEG structure, and therefore make it possible to revise the formulations of cosmetics and external use preparations to be completely PEG-free formulations (i.e., formulations that do not include compounds having a polyoxyethylene (PEG) structure). Namely, using the organopolysiloxane elastomer of the present invention makes it possible for the cosmetics industry to revise the composition of end consumer products to have completely PEG-free formulations.

In other words, it has been confirmed not only that pulverized particles of the organopolysiloxane elastomer of the present invention can be used in far more multifaceted ways compared to conventional hydrophilic silicone elastomers of the conventional examples, but also that it greatly increases the overall value of external use preparations and cosmetics.

Furthermore, the emulsion obtained here has the excellent feature that there is very little odor generation due to the passage of time or temperature, which verifies that the emulsion is extremely useful as a raw material for an external use preparation or a cosmetic.

The cosmetic and external use preparation of the present invention can also be obtained by substituting the paste-like composition according to the present invention for the "paste-like composition of practical example X" in the various formulation examples in the other patent application for which priority right is asserted based on Japanese Patent Application No. 2011-121097 (relating to a sugar alcohol-modified silicone elastomer), submitted on the same day as this application. Furthermore, the organopolysiloxane elastomer of the present invention may be used in the specific cosmetic formulations 1 to 47 indicated in the below table.

TABLE 8

[Formulation Example 1] W/O cream foundation
[Formulation Example 2] W/O Liquid foundation
[Formulation Example 3] W/O type compact foundation
[Formulation Example 4] O/W/O type liquid foundation
[Formulation Example 5] W/O makeup foundation
[Formulation Example 6] Rouge
[Formulation Example 7] Powder foundation
[Formulation Example 8] W/O type compact foundation
[Formulation Example 9] Eye shadow
[Formulation Example 10] W/O type UV blocking cream TABLE 8-continued

[Formulation Example 11] W/O type UV blocking emulsion
[Formulation Example 12] O/W type UV blocking cream
[Formulation Example 13] W/O/W type cream
[Formulation Example 14] O/W/O type emulsion
[Formulation Example 15] Skin care emulsion
[Formulation Example 16] Skin care cream
[Formulation Example 17] Foundation
[Formulation Example 18] O/W type sunscreen agent
[Formulation Example 19] Powder eye shadow
[Formulation Example 20] Rouge
[Formulation Example 21] Mascara
[Formulation Example 22] O/W cream
[Formulation Example 23] O/W cream
[Formulation Example 24] Stick type antiperspirant
[Formulation Example 25] Anhydrous roll-on type antiperspirant
[Formulation Example 26] Nonaqueous antiperspirant deodorant stick composition
[Formulation Example 27] W/O solid antiperspirant stick composition
[Formulation Example 28] W/O emulsion type antiperspirant cream composition
[Formulation Example 29] Water-in-oil type emulsion transparent antiperspirant composition
[Formulation Example 30] Nonaqueous stick type antiperspirant composition
[Formulation Example 31] Hair conditioner
[Formulation Example 32] Shampoo
[Formulation Example 33] Hair cream (set type)
[Formulation Example 34] Shampoo
[Formulation Example 35] Hair conditioner
[Formulation Example 36] Hair treatment, rinse type
[Formulation Example 37] Hair treatment, leave-on type
[Formulation Example 38] Hair mist
[Formulation Example 39] Hair foam
[Formulation Example 40] Hair spray
[Formulation Example 41] Hair wax
[Formulation Example 40] Hair cream
[Formulation Example 43] Hair lotion
[Formulation Example 44] Hair oil
[Formulation Example 45] Oxidation type hair color
[Formulation Example 46] Hair manicure
[Formulation Example 47] Perm solution The specific details of these formulation examples are disclosed completely and in detail in a patent application corresponding to the present application (Japanese patent application asserting priority right based on Japanese Patent Application No. 2011-121097) and filed in Japan by the applicant of the present application on the same date as the present application as well as in the Japanese patent application (Japanese Patent Application No. 2011-121097) serving as the basis for the assertion of priority right for the patent application. These disclosures are herein incorporated by reference.

The invention claimed is:

1. An organopolysiloxane elastomer comprising: a group having a siloxane dendron structure represented by $L^1$ that is bonded to a silicon atom, and having a crosslinked structure that includes a carbon-silicon bond in a crosslinking portion;
wherein, $L^1$ is a silylalkyl group having a siloxane dendron structure and, when i=1, represented by following general formula (2):

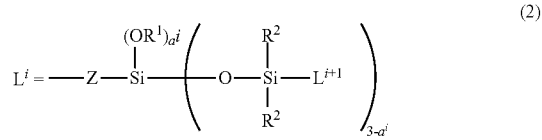

wherein,
$R^1$ represents a substituted or unsubstituted, straight or branched monovalent hydrocarbon group having from 1 to 30 carbons;

$R^2$ each independently represents an alkyl group or a phenyl group having from 1 to 6 carbons;

Z is a divalent organic group;

i represents a generation of the silylalkyl group represented by $L^i$ and is an integer of 1 to k when k is a number of generations that is a number of repetitions of the silylalkyl group; the number of generations k is an integer from 1 to 10; $L^{i+1}$ is the silylalkyl group when i is less than k, and $R^2$ when i=k, and $a^i$ is a number in a range of 0 to 3.

2. The organopolysiloxane elastomer according to claim 1, wherein $L^1$ in general formula (2) is a functional group represented by following general formula (2-1) or general formula (2-2):

General Formula (2-1):

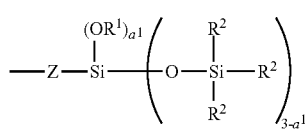
(2-1)

General Formula (2-2):

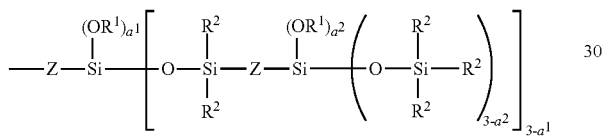
(2-2)

wherein, $R^1$, $R^2$, and Z are the same groups as described above, and $a^1$ and $a^2$ are each independently numbers in a range of 0 to 3.

3. The organopolysiloxane elastomer according to claim 1, comprising the group having a siloxane dendron structure represented by $L^1$ that is bonded to a silicon atom, and having a hydrophilic group represented by Q bonded to a different silicon atom from the silicon atom, and having the crosslinked structure that includes a carbon-silicon bond in the crosslinking portion;

wherein, Q is a hydrophilic group bonded to a silicon atom via a linking group that is at least divalent including at least one type of hydrophilic unit selected from hydrophilic units represented by following general formulae (3-1) to (3-4):

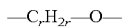
(3-1)

wherein, r is a number in a range of 1 to 6;

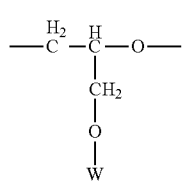
(3-2)

wherein, W represents a hydrogen atom or an alkyl group having from 1 to 20 carbons;

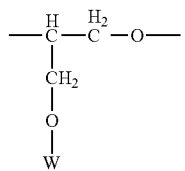
(3-3)

wherein, W is synonymous with the groups described above; and

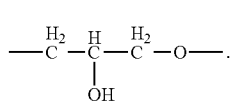
(3-4)

4. The organopolysiloxane elastomer according to claim 3, wherein the Q
has a linear hydrophilic segment having a plurality of the hydrophilic units bonded in a linear fashion, or
has a branched hydrophilic segment having a plurality of the hydrophilic units bonded in a branched fashion via at least one branching unit selected from groups represented by following structural formulae (3-5) to (3-7):

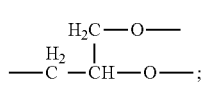
(3-5)

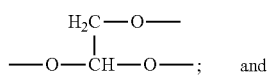
(3-6)

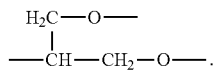
(3-7)

5. The organopolysiloxane elastomer according to claim 3, wherein the Q is a hydrophilic group represented by any one of following general formulae (4-1) to (4-4):

General Formula (4-1):

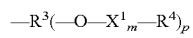
(4-1)

wherein,
$R^3$ is an organic group having (p+1) valency,
p is a number in a range of 1 to 3;
$X^1$ are each independently at least one hydrophilic unit selected from the hydrophilic units represented by the general formulae (3-1) to (3-4) above;
m is a number in a range of 1 to 100; and
$R^4$ is a hydrogen atom or a group selected from the group consisting of alkyl groups, acyl groups, and glycidyl groups having from 1 to 20 carbons;

General Formula (4-2):

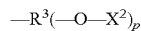
(4-2)

wherein,
$R^3$ is synonymous with the groups described above,
p is the same number as described above, and $X^2$ is a hydrophilic group represented by the following structural formal (4-2-1):

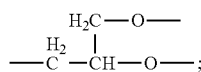
(4-2-1)

wherein, at least one hydrophilic unit selected from the hydrophilic units represented by the general formulae (3-1) to (3-4) is independently bonded to each of the two oxygen atoms;

General Formula (4-3):

$$—R^3(—O—X^3)_p \quad (4\text{-}3)$$

wherein,
$R^3$ is synonymous with the groups described above,
p is the same number as described above, and
$X^3$ is a hydrophilic group represented by the following structural formula (4-3-1):

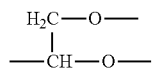
(4-3-1)

wherein, at least one hydrophilic unit selected from the hydrophilic units represented by the general formulae (3-1) to (3-4) is independently bonded to each of the two oxygen atoms;

General Formula (4-4):

$$—R^3(—O—X^4)_p \quad (4\text{-}4)$$

wherein,
$R^3$ is synonymous with the groups described above,
p is the same number as described above, and
$X^4$ is a hydrophilic group represented by following structural formula (4-4-1):

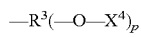
(4-4-1)

wherein, at least one hydrophilic unit selected from the hydrophilic units represented by the general formulae (3-1) to (3-4) is independently bonded to each of the two oxygen atoms.

6. The organopolysiloxane elastomer according to claim 1, the organopolysiloxane elastomer being obtained by causing reactions between at least the following:
(A) an organohydrogenpolysiloxane;
(B) a siloxane dendron having one reactive unsaturated group in a molecule; and
(C) at least one organic compound selected from the group consisting of (C1) organic compounds having an average of more than one reactive unsaturated groups in a molecule, and (C2) organic compounds having at least one reactive unsaturated group and at least one epoxy group in a molecule.

7. The organopolysiloxane elastomer according to claim 1, the organopolysiloxane elastomer being obtained by causing reactions between at least the following:
(A) an organohydrogenpolysiloxane;
(B) a siloxane dendron having one reactive unsaturated group in a molecule;
(C) at least one organic compound selected from the group consisting of (C1) organic compounds having an average of more than one reactive unsaturated groups in a molecule, and (C2) organic compounds having at least one reactive unsaturated group and at least one epoxy group in a molecule, provided that the (C) is optional in cases where (D) has an average of more than one reactive unsaturated group in a molecule; and
(D) a hydrophilic derivative having a reactive unsaturated group and a hydrophilic group that includes at least one hydrophilic unit selected from the hydrophilic units represented by the structural formulae (3-1) to (3-4).

8. The organopolysiloxane elastomer according to claim 6, wherein an average number of silicon-bonded hydrogen atoms in a molecule of the component (A) that react with an unsaturated bond in the component (C) and/or component (D) is 0.1 or greater.

9. The organopolysiloxane elastomer according to claim 6, wherein the component (A) is represented by average composition formula (1):

$$R^5{}_a H_b SiO_{(4-a-b)/2} \quad (1)$$

wherein,
$R^5$ each independently represent monovalent organic groups, wherein $1.0 \le a \le 3.0$ and $0.001 \le b \le 1.5$.

10. The organopolysiloxane elastomer according to claim 6, wherein the component (B) is a compound having a siloxane dendron structure having one carbon-carbon double bond at a molecular terminal, and represented by following general formula (2'):

General Formula (2'):

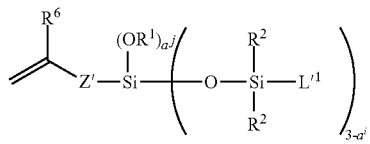
(2')

wherein,
$L'^1$ is an alkyl group or phenyl group having from 1 to 6 carbons, or when j=1, a silylalkyl group represented by the following general formal (2"):

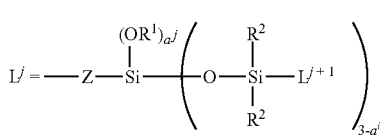
(2")

wherein,
$R^2$ is an alkyl group or phenyl group having from 1 to 6 carbons,
Z is a divalent organic group,
j represents the number of generations of the silylalkyl group that is represented by $L^j$, when the number of generations, the number of repetitions, of the silylalkyl group is k', j is an integer from 1 to k', and the number of generations k' is an integer from 1 to 10; $L^{j+1}$ is the silylalkyl group when j is less than k' and is the $R^2$ when j=k'; and
$a^j$ is a number in a range of 0 to 3;
Z' is a divalent organic group, and
$R^6$ is a hydrogen atom or a methyl group.

11. The organopolysiloxane elastomer according to claim 6, wherein the component (C) is at least one organic compound selected from following (C1-1) to (C1-5) and (C2-1) to (C2-2):

(C1-1) an α,ω-diene represented by general formula (5-1):

$$CH_2=CH(CH_2)_xCH=CH_2 \qquad (5-1)$$

wherein, $1 \leq x \leq 20$;

(C1-2) an α,ω-diyne represented by general formula (5-2):

$$CH\equiv C(CH_2)_xC\equiv CH \qquad (5-2)$$

wherein, $1 \leq x \leq 20$;

(C1-3) an α,ω-ene-yne represented by general formula (5-3):

$$CH_2=CH(CH_2)_xC\equiv CH \qquad (5-3)$$

wherein, $1 \leq x \leq 20$;

(C1-4) a bisalkenyl polyether compound represented by general formula (5-4):

$$C_qH_{2q-1}O(C_nH_{2n}O)_yC_qH_{2q-1} \qquad (5-4)$$

wherein, $2 \leq q \leq 20$ and $2 \leq n \leq 4$, y is the total number of repetitions of oxyethylene units, oxypropylene units, or oxybutylene units, and $1 \leq y \leq 180$;

(C1-5) unsaturated group-containing silicone compound represented by average composition formula (5-5):

$$R^7_cR^8_dSiO_{(4-c-d)/2} \qquad (5-5)$$

wherein, $R^7$ may each independently represent a monovalent organic group that differs from $R^8$;
$R^3$ is each independently a monovalent unsaturated aliphatic hydrocarbon group having from 2 to 30 carbons, $1.0 \leq c \leq 2.5$, and $0.001 \leq d \leq 1.5$;

(C2-1) an unsaturated epoxy compound represented by general formula (5-6):

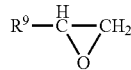
(5-6)

wherein, $R^9$ is a substituted or unsubstituted, straight or branched monovalent hydrocarbon group having one unsaturated bond and from 2 to 20 carbons; and (C2-2) an unsaturated group-containing alicyclic epoxy compound represented by general formula (5-7):

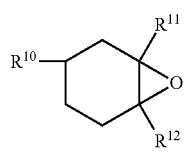
(5-7)

wherein, $R^{10}$ represents a substituted or unsubstituted, straight or branched monovalent hydrocarbon group having one unsaturated bond and from 2 to 20 carbons, $R^{11}$ represents a hydrogen atom or a methyl group; and $R^{12}$ represents a hydrogen atom or a methyl group.

12. The organopolysiloxane elastomer according to claim 9, wherein the monovalent organic group that is $R^5$ in the average composition formula (1) is selected from following (E1) to (E9):

(E1) a substituted or unsubstituted, straight or branched monovalent hydrocarbon group having from 1 to 60 carbons;

(E2) a polyoxyalkylene group represented by —$R^{13}$O(AO)$_z$$R^{14}$, wherein, AO is an oxyalkylene group having from 2 to 4 carbons, $R^{13}$ is a substituted or unsubstituted, straight or branched divalent hydrocarbon group having from 3 to 5 carbons, $R^{14}$ is a hydrogen atom, a substituted or unsubstituted, straight or branched monovalent hydrocarbon group having from 1 to 24 carbons, or a substituted or unsubstituted, straight or branched acyl group having from 2 to 24 carbons, and $z=1$ to 100;

(E3) a substituted or unsubstituted, straight or branched alkoxy group having from 1 to 30 carbons;

(E4) a hydroxyl group;

(E5) an ester group represented by —$R^{15}$—COOR$^{16}$, wherein, $R^{15}$ represents a substituted or unsubstituted, straight or branched divalent hydrocarbon group having from 2 to 20 carbons, and $R^{16}$ represents a substituted or unsubstituted, straight or branched monovalent hydrocarbon group having from 1 to 30 carbons;

(E6) an ester group represented by —$R^{17}$—OCOR$^{18}$, wherein, $R^{17}$ represents a substituted or unsubstituted, straight or branched divalent hydrocarbon group having from 2 to 20 carbons, and $R^{18}$ represents a substituted or unsubstituted, straight or branched monovalent hydrocarbon group having from 1 to 30 carbons;

(E7) an alkyl group substituted with a polysiloxane chain structure and represented by following general formula (6):

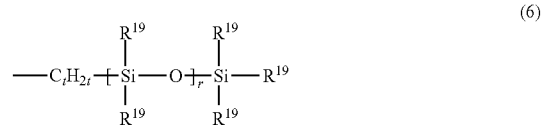
(6)

wherein, $R^{19}$ is each independently a substituted or unsubstituted, straight or branched monovalent hydrocarbon group having from 1 to 30 carbons, a hydroxyl group, or hydrogen atom, at least one of the $R^{19}$ being the monovalent hydrocarbon group; t is a number in a range of 2 to 10, and r is a number in a range of 1 to 100;

(E8) an epoxy group represented by following general formula (7):

(7)

wherein, $R^{20}$ represents a substituted or unsubstituted, straight or branched divalent hydrocarbon group having from 2 to 20 carbons; and (E9) an alicyclic epoxy group represented by following general formula (8):

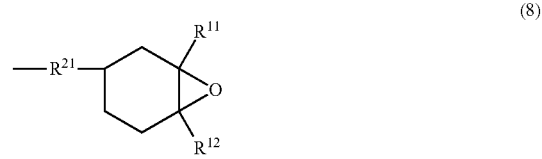
(8)

wherein, $R^{21}$ represents a substituted or unsubstituted, straight or branched divalent hydrocarbon group having from 2 to 20 carbons; and $R^{11}$ and $R^{12}$ are synonymous with those described above.

13. The organopolysiloxane elastomer according to claim 1, wherein the organopolysiloxane elastomer is in a form of a particle.

14. The organopolysiloxane elastomer according to claim 13, wherein the organopolysiloxane elastomer is in the form of a particle having a volume average particle size in a range of 20 to 1,000 μm.

15. The organopolysiloxane elastomer according to claim 1, wherein: the organopolysiloxane elastomer is capable of swelling as a result of including a weight amount of an oil agent that is at least the weight of the organopolysiloxane elastomer itself.

16. A composition comprising the organopolysiloxane elastomer according to claim 1 and at least one oil agent.

17. The composition according to claim 16, wherein the composition is in the form of a paste.

18. The composition according to claim 16, the composition being obtained by using mechanical force to pulverize the organopolysiloxane elastomer, and then mixing the same with at least one oil agent, or by using mechanical force to pulverize a mixture of the organopolysiloxane elastomer and at least one oil agent.

19. An organopolysiloxane elastomer, the organopolysiloxane elastomer or a composition thereof being obtained by treating the organopolysiloxane elastomer according to claim 1 by adding at least one type of acidic substance, and then removing volatile components by heating or reducing pressure.

20. The composition according to claim 16, the composition being in the form of an emulsion.

21. An external use preparation raw material comprising the organopolysiloxane elastomer according to claim 1.

22. An external use preparation raw material according to claim 21, the external use preparation raw material being a gelling agent, a structuring agent, a thickener, a tactile sensation improver, a moisturizing agent, a masking agent, a surfactant, an emulsifier, or a powder dispersion stabilizer.

23. An external use preparation comprising the organopolysiloxane elastomer according to claim 1.

24. An organopolysiloxane elastomer production method comprising a step of causing reactions between at least the following: (A) an organohydrogenpolysiloxane;
(B) a siloxane dendron having one reactive unsaturated group in a molecule; and
(C) at least one organic compound selected from the group consisting of (C1) organic compounds having an average of more than one reactive unsaturated groups in a molecule, and (C2) organic compounds having at least one reactive unsaturated group and at least one epoxy group in a molecule.

25. The organopolysiloxane elastomer production method according to claim 24, wherein some or all of the reactions are performed in the presence of no solvent or in the presence of at least one solvent selected from a group represented by (P-1) to (P-2):
(P-1): an organic compound; and
(P-2): a compound having a silicon atom.

26. The organopolysiloxane elastomer production method according to claim 24, wherein (A) and (B) are reacted first, and then (C) is added and a crosslinking reaction is performed, and wherein an optional component (Q) is reacted with (A) before the (A)-(B) reaction, or is further reacted following the (A)-(B) reaction, or is reacted simultaneous with the (A)-(B) reaction, or is further reacted following crosslinking by (C); where (Q) is a compound having one unsaturated group in a molecule, excluding the compound (C2).

27. The organopolysiloxane elastomer production method according to claim 24, wherein (A) and (C) are reacted first to introduce a crosslinking portion, and then (B) is added and reacted, and wherein an optional component (Q) is reacted with (A) before the (A)-(C) reaction, or is further reacted following the (A)-(C) reaction, or is further reacted following the reaction with (B); where (Q) is a compound having one unsaturated group in a molecule, excluding the compound (C2).

28. An organopolysiloxane elastomer production method comprising a step of causing reactions between at least the following:
(A) an organohydrogenpolysiloxane;
(B) a siloxane dendron having one reactive unsaturated group in a molecule;
(C) at least one organic compound selected from the group consisting of (C1) organic compounds having an average of more than one reactive unsaturated groups in a molecule, and (C2) organic compounds having at least one reactive unsaturated group and at least one epoxy group in a molecule, provided that the (C) is optional in cases where (D) has an average of more than one reactive unsaturated group in a molecule; and
(D) a hydrophilic derivative having a reactive unsaturated group and a hydrophilic group that contains at least one hydrophilic unit selected from the hydrophilic units represented by the structural formulae (3-1) to (3-4).

29. The organopolysiloxane elastomer production method according to claim 28, wherein some or all of the reactions are performed in the presence of no solvent or in the presence of at least one solvent selected from a group represented by (P-1) to (P-2):
(P-1): an organic compound; and
(P-2): a compound having a silicon atom.

30. The organopolysiloxane elastomer production method according to claim 28, wherein (B) and (D) are successively reacted with the (A) in any order, provided that (D) is limited to compounds having one reactive unsaturated group in a molecule, after which, (C) is added and a crosslinking reaction is performed, and wherein the optional component (Q) is reacted with (A) before the (A)-(B) reaction or before the (A)-(D) reaction, or is further reacted following the (A)-(B) reaction or following the (A)-(D) reaction, or is reacted simultaneous with the (A)-(B) reaction or simultaneous with the (A)-(D) reaction, or is further reacted following crosslinking by (C); where
(Q) is a compound having one unsaturated group in a molecule, excluding the compound (C2).

31. The organopolysiloxane elastomer production method according to claim 28, wherein (A) and (C) are reacted first to introduce a crosslinking portion, after which, (B) and (D) are added and successively reacted in any order, provided that (D) is limited to compounds having one reactive unsaturated group in a molecule, and wherein the optional component (Q) is reacted with (A) before the (A)-(C) reaction, or is further reacted following the (A)-(C) reaction, or is further reacted following the reactions with (B) and (D); where (Q) is a compound having one unsaturated group in a molecule, excluding the compound (C2).

* * * * *